United States Patent
Lim et al.

(10) Patent No.: US 11,518,798 B2
(45) Date of Patent: Dec. 6, 2022

(54) VASCULAR ENDOTHELIAL GROWTH FACTOR RECEPTOR TARGETING PEPTIDE-ELASTIN FUSION POLYPEPTIDES

(71) Applicants: INDUSTRY-UNIVERSITY COOPERATION FOUNDATION HANYANG UNIVERSITY ERICA CAMPUS, Ansan-si (KR); INJE UNIVERSITY INDUSTRY-ACADEMIC COOPERATION FOUNDATION, Gimhae-si (KR)

(72) Inventors: Dong Woo Lim, Ansan-si (KR); Min Jung Kang, Bucheon-si (KR); Jae Sang Lee, Ansan-si (KR); Sae-Gwang Park, Busan (KR)

(73) Assignees: Industry-University Cooperation Foundation Hanyang University Erica Campus, Ansan-si (KR); Inje University Industry-Academic Cooperation Foundation, Gimhae-si (KR)

( * ) Notice: Subject to any disclaimer, the term of this patent is extended or adjusted under 35 U.S.C. 154(b) by 367 days.

(21) Appl. No.: 16/853,435

(22) Filed: Apr. 20, 2020

(65) Prior Publication Data

US 2020/0331986 A1 Oct. 22, 2020

Related U.S. Application Data

(62) Division of application No. 15/744,278, filed as application No. PCT/KR2016/011757 on Oct. 19, 2016, now Pat. No. 10,662,236.

(30) Foreign Application Priority Data

Apr. 7, 2016 (KR) .................. 10-2016-0042655
Oct. 19, 2016 (KR) .................. 10-2016-0135510

(51) Int. Cl.
| | | |
|---|---|---|
| C07K 14/78 | (2006.01) | |
| C07K 14/71 | (2006.01) | |
| A61K 38/39 | (2006.01) | |
| A61K 9/14 | (2006.01) | |
| A61K 38/18 | (2006.01) | |
| C07K 16/28 | (2006.01) | |
| B82Y 5/00 | (2011.01) | |
| A61P 43/00 | (2006.01) | |

(52) U.S. Cl.
CPC .............. *C07K 14/78* (2013.01); *A61K 9/141* (2013.01); *A61K 38/1866* (2013.01); *A61K 38/39* (2013.01); *A61P 43/00* (2018.01); *C07K 14/71* (2013.01); *C07K 16/2863* (2013.01); *B82Y 5/00* (2013.01); *C07K 2319/00* (2013.01)

(58) Field of Classification Search
CPC ...... C07K 14/71; C07K 14/78; C07K 2319/00; A61K 38/1866; A61K 38/39
See application file for complete search history.

(56) References Cited

U.S. PATENT DOCUMENTS

2007/0265197 A1 11/2007 Furgeson et al.

FOREIGN PATENT DOCUMENTS

| KR | 10-2012-0094867 A | | 8/2012 | |
| KR | 10-2012-0016142 | * | 8/2021 | .............. A61K 38/08 |

OTHER PUBLICATIONS

Abstract of the Research Papers of "The Polymer Society of Korea Spring Meeting", Apr. 8, 2015-Apr. 10, 2015, pp. 17 and 82, vol. 40, No. 1.
Dan E. Meyer et al., "Protein Purification by Inverse Transition Cycling", Protein-Protein Interactions: A Molecular Cloning Manual, 2002, pp. 329-343, Chapter 18.
Dan W. Urry et al., "Temperature of Polypeptide Inverse Temperature Transition Depends on Mean Residue Hydrophobicity", J. Am. Chem. Soc, 1991, pp. 4346-4348, vol. 113.
D'Andrea et al.—Targeting angiogenesis: Structural characterization and biological properties of a de novo engineered VEGF mimicking peptide. Proc. Natl. Acad Sci., 102, 14215-14220, 2005. (Year: 2005).
Despanie et al. Elastin-like polypeptides: Therapeutic applications for an emerging class of nanomedicines. J. Control Rel., 240, 93-108, 2016—ePub Nov. 11, 2015. (Year: 2015).
Gagner et al., "Designing Protein-based Biomaterials for Medical Applications", Acta Biomaterialia, 2014, pp. 1542-1557, vol. 10.
Kim et al., "Hyaluronate-Flt1 Peptide Conjugate/epirubicin Micelles for Theranostic Application to Liver Cancers", RSC Advances, 2015, pp. 48615-48618, vol. 5.
Kowalczyk et al., "Elastin-like Polypeptides as a Promising Family of Genetically-engineered Protein Based Polymers", World Journal of Microbiology and Biotechnology, 2014, pp. 2141-2152, vol. 30.

* cited by examiner

*Primary Examiner* — Elly-Gerald Stoica
(74) *Attorney, Agent, or Firm* — Rabin & Berdo, P.C.

(57) ABSTRACT

Disclosed is a fusion polypeptide for inhibiting neovascularization, including a peptide specifically binding to vascular endothelial growth factor (VEGF) receptors, and a hydrophilic elastin-based polypeptide (hydrophilic EBP) linked to the peptide.

8 Claims, 14 Drawing Sheets

Specification includes a Sequence Listing.

VASCULAR ENDOTHELIAL GROWTH FACTOR RECEPTOR TARGETING PEPTIDE-ELASTIN FUSION POLYPEPTIDES

CROSS-REFERENCE TO RELATED APPLICATION

This is a divisional application of co-pending U.S. application Ser. No. 15/744,278, filed on Jan. 12, 2018, which was a national stage of PCT application No. PCT/KR2016/011757, filed on Oct. 19, 2016, and claims priority to and the benefit of Korean Patent Applications Nos. 10-2016-0042655 and 10-2016-0135510, filed on Apr. 7, 2016 and Oct. 19, 2016, respectively, the disclosures of which are incorporated herein by reference in its entirety.

SEQUENCE LISTING

This divisional application contains a Sequence Listing submitted via EFS-Web and hereby incorporated by reference in its entirety. The Sequence Listing is named DAH-266NPD1-2A_Sequence_Listing_Revised.txt, created on Jun. 25, 2020, and 66,430 bytes in size.

BACKGROUND

1. Field of the Invention

The present invention relates to a fusion polypeptide and a self-assembled nanostructure for inhibiting neovascularization, and more particularly, to a fusion polypeptide for inhibiting neovascularization including a peptide specifically binding to vascular endothelial growth factor (VEGF) receptors; and a hydrophilic elastin-based polypeptide (hydrophilic EBP) linked to the peptide.

In addition, the present invention relates to a fusion polypeptide for inhibiting neovascularization including a peptide specifically binding to VEGF receptors; a hydrophilic EBP linked to the peptide; and a hydrophobic elastin-based polypeptide (hydrophobic EBP) linked to the hydrophilic EBP, and a self-assembled nanostructure thereof.

2. Discussion of Related Art

Peptides, polypeptides and proteins having specific functions, such as cell penetration, cell attachment, binding affinity to target molecules, therapeutic efficacy, and site-specific conjugation, may be fused together to form a multifunctional artificial chimera or fusion protein suitable for smart drug delivery systems.

Such fusion proteins exhibit high specificity, high activity, long half-lives, low accumulation in certain organs, and low side effects when used in vivo. Recently, multifunctional fusion proteins have been prepared at the genetic level with recombinant DNA technology and the following are precisely regulated: (1) sequence and composition of amino acids, (2) fusion order, (3) monodisperse molecular weight, (4) hydrophilicity and hydrophobicity, (5) environmental responsiveness, (6) biocompatibility and biodegradability, (7) toxicity and immunogenicity, (8) pharmacokinetics and pharmacodynamics.

The fusion proteins are expressed in high yield (0.1 to 0.5 g per liter of culture) in prokaryotic or eukaryotic expression systems, and are purified by column chromatography or inverse transition cycling (ITC) for analyzing unique phase transition behaviors induced by stimuli-responsiveness of the fusion proteins. For example, antimicrobial host-defense peptides were genetically fused with polypeptide F4 to overcome limitations of the host-defense peptides, such as low stability, short half-lives and high production cost. Furthermore, tumor-targeting antibodies were prepared in mice using a hybridoma technology, and antigen-binding variable domains of mouse antibodies were combined with human IgG to reduce immunogenicity in patients. A large number of artificial fusion proteins are in preclinical and clinical development, and technologies using multi-functional artificial chimeric or fusion protein-based therapeutics are growing exponentially.

Elastin-based polypeptides (EBPs) are thermal response biopolymers derived from elastomeric domains. Elastin is a major protein component of the extracellular matrix (ECM). EBPs are modified to have thermal sensitivity based on an elastomeric domain and are composed of a pentapeptide repeat unit, Val-Pro-(Gly or Ala)-$X_{aa}$-Glys[VP (G or A)XG]. EBPs are thermally responsive polypeptides, and transition temperatures thereof are readily controlled to form nanostructures for drug delivery.

$X_{aa}$ is a guest residue and may be any amino acid except proline. Depending on a sequence corresponding to the repeat unit, there are two types of EBPs, one is an elastin-based polypeptide with elasticity (EBPE) with a sequence of Val-Pro-Gly-$X_{aa}$-Gly and the other is an elastin-based polypeptide with plasticity (EBPP) with a sequence of Val-Pro-Ala-$X_{aa}$-Gly.

EBPs exhibit a lower critical solution temperature (LCST) behavior in which a reversible phase transition is observed depending on temperature. The LCST provides the advantage of using an easy purification method such as inverse transition cycling (ITC) and the advantage of being thermally triggered to self-assemble into particles, gels, fibers and other structures.

Diblocks composed of EBP blocks that have different sequences are used to form self-assembled structures. An EBP diblock copolymer is composed of two EBPs, in which the EBPs have different sequences and different transition temperatures ($T_t$) to form a self-assembled micellar structure. When the temperature of an EBP diblock copolymer solution increases above a lower $T_t$, EBPs that have a low $T_t$ become insoluble whereas EBPs that have a high $T_t$ are soluble, and amphiphilic diblock EBPs are self-assembled into micellar structures. EBP diblock copolymers may be fused with other functional peptides, e.g., a cell penetrating peptide capable of penetrating cells, to have functional multivalency as micellar structures.

Soluble EBPs may be used as inert protein-based biomaterials, like poly(ethylene glycol) (PEG), and as drug delivery carriers with drugs or other functional proteins, for advanced drug delivery systems, regenerative medicine, and tissue engineering.

EBPs may be easily purified and have stimuli-triggered phase transitions, allowing for genetic fusion with other functional proteins and exploitation of the advantages of EBPs. For example, EBPs may be fused with an interleukin-1 receptor antagonist (IL-1Ra) to create an injectable drug reservoir for treating osteoarthritis.

In addition, with the advancement of therapeutic EBP fusion proteins, self-assembled micelles of EBP block copolymers are being studied. An EBP diblock copolymer is composed of two different EBP blocks, each of which has a different sequence, configuration and chain length, which allows each EBP block to have a unique transition temperature ($T_t$). When temperature rises, the EBP block with a low $T_t$ becomes insoluble, while another EBP block with a high $T_t$ becomes soluble above the low $T_t$. Due to the amphiphilic properties of the EBP diblock copolymer above the low $T_t$, the EBP diblock copolymer self-assembles into a core-shell micellar nanostructure. In addition, EBP diblock copolymers may be fused with other functional peptides or proteins to become functionally multivalent. Both the core and shell of the EBP micellar nanostructure may be used differently as drug delivery carriers.

Recently, a considerable number of cancer-related diseases have been known to result from abnormal neovascularization in tumors. Physiological neovascularization in organisms is strictly regulated and is only activated under specific conditions. However, excessive formation of blood vessels due to disruption of regulation may lead to diseases such as non-tumor diseases as well as cancers. Under physiological conditions, including development, growth, wound healing, and regeneration, neovascularization is stimulated by vascular endothelial growth factor (VEGF). VEGF binds to two types of VEGF receptors (VEGFRs), including VEGFR1 (fms-like tyrosine kinase-1 or Flt1) and VEGFR2 (kinase insert domain-containing receptor or Flk-1/KDR), present on cell membranes. Selective binding of VEGF to VEGF receptors delivers a growth signal to vascular endothelial cells, which in turn triggers neovascularization.

Therefore, to inhibit neovascularization in various diseases such as tumor growth, cancer metastasis, retinal neovascularization, corneal neovascularization, diabetic retinopathy and asthma, various strategies for anti-neovascularization have been employed. In particular, anti-neovascularization strategies for treatment of ocular neovascularization include initiating a signal that inhibits neovascularization using neovascularization inhibitors such as pigment epithelial-derived factor (PEDF) and caffeic acid (CA), and blocking neovascularization signals by interfering with binding of VEGF to receptors thereof (VEGFRs). In particular, since biomacromolecules and targeting peptides have high affinity for VEGFR1 and competitively bind to VEGFR1 as receptor antagonists, using biomacromolecules or targeting peptides as antibodies may be a challenging strategy related to interfering with binding of VEGF to VEGF receptors.

An anti-Flt1 peptide identified by PS-SPCL (positional scanning-synthetic peptide combinatorial library) screening, one among high throughput screening (HTS) systems, is a hexa-peptide having an amino acid sequence of Gly-Asn-Gln-Trp-Phe-Ile (GNQWFI). The anti-Flt1 peptide, as a VEGFR1-specific antagonist, specifically binds to VEGFR1, which prevents VEGFR1 from interacting with all VEGFR1 ligands, including placental growth factor (PlGF), as well as VEGF. To increase the half-life of the anti-Flt1 peptide in vivo, anti-Flt1 peptide-hyaluronate (HA) conjugates have been studied in connection with the formation of self-assembled micelle structures which encapsulate genistein, dexamethasone or tyrosine-specific protein kinase inhibitors. Although conjugation of the anti-Flt1 peptide with HA polymers increases the half-life of the anti-Flt1 peptide in the body, conjugation efficiency and micellar structures are heterogeneous due to polydisperse HA polymer molecular weights, random distribution, and inconsistency of conjugation efficiency of the anti-Flt1 peptides and the HAs.

The present inventors have continued to study fusion polypeptides for inhibiting neovascularization. As a result, a novel fusion polypeptide in which a peptide targeting vascular endothelial growth factor (VEGF) receptors and an elastin-based polypeptide were fused was developed and the present invention was completed.

SUMMARY OF THE INVENTION

Therefore, the present invention has been made in view of the above problems, and it is an objective of the present invention to provide a novel fusion polypeptide for inhibiting neovascularization.

It is another objective of the present invention to provide a self-assembled nanostructure of the fusion polypeptide.

It is still another objective of the present invention to provide a composition for treating diseases caused by neovascularization.

It is yet another objective of the present invention to provide a method of inhibiting neovascularization in individuals.

According to an aspect of the present invention, there is provided a fusion polypeptide for inhibiting neovascularization, including:

a peptide specifically binding to vascular endothelial growth factor (VEGF) receptors; and a hydrophilic elastin-based polypeptide (hydrophilic EBP) linked to the peptide.

The peptide specifically binding to VEGF receptors may be a peptide that specifically binds to VEGF receptor Flt1 or Flk-1/KDR.

The peptide specifically binding to VEGF receptors may be a peptide that specifically binds to VEGF receptor Flt1 or Flk-1/KDR, and is also called "VEGF receptor-specific peptide" or "VEGF receptor-targeting peptide". The VEGF receptor-specific peptide may be any of anti-Flt1 or anti-Flk-1/KDR (poly)peptides well known in the art. For example, the peptide may be an anti-Flt1 peptide [SEQ ID NO. 38], but is necessarily limited thereto.

The hydrophilic EBP may be composed of an amino acid sequence represented by Formula 1 or 2 below:

```
Formula 1
                                          [SEQ ID NO. 1]
    n; or Formula 2
                                          [SEQ ID NO. 2]
    n, wherein SEQ ID NO. 1 is consisted of
[VPGXG VPGXG VPGXG VPGXG VPGXG VPGXG];

SEQ ID NO. 2 is consisted of
[VPAXG VPAXG VPAXG VPAXG VPAXG VPAXG];
``` n is an integer of 1 or more, and represents the number of repeats of SEQ ID NO. 1 or SEQ ID NO. 2; and X is an amino acid other than proline, is selected from any natural or artificial amino acid when the pentapeptide VPGXG or VPAXG is repeated, and at least one of X is a hydrophilic amino acid.

The hydrophilic EBP may be composed of an amino acid sequence represented by Formula 1 or 2 below:

in Formula 1, n is 1, each X of the pentapeptide repeats is consisted of,

A (Ala), G (Gly), and I (Ile) in a ratio of 1:4:1 [SEQ ID NO. 20];

K (Lys), G (Gly), and I (Ile) in a ratio of 1:4:1 [SEQ ID NO. 22];

D (Asp), G (Gly), and I (Ile) in a ratio of 1:4:1 [SEQ ID NO. 24]; or

E (Glu), G (Gly), and I (Ile) in a ratio of 1:4:1 [SEQ ID NO. 26], or in Formula 2, n is 1, and the pentapeptide repeats in Formula 2, n is 1, and each X of the pentapeptide repeats is consisted of, A (Ala), G (Gly), and I (Ile) in a ratio of 1:4:1 [SEQ ID NO. 21];

K (Lys), G (Gly), and I (Ile) in a ratio of 1:4:1 [SEQ ID NO. 23];

D (Asp), G (Gly), and I (Ile) in a ratio of 1:4:1 [SEQ ID NO. 25]; or

E (Glu), G (Gly), and I (Ile) in a ratio of 1:4:1 [SEQ ID NO. 27].

The hydrophilic EBP may include an amino acid sequence represented by Formula 2 below:

in Formula 2, n is 3, 6, 12 or 24, and the pentapeptide repeats correspond to SEQ ID NO. 41, SEQ ID NO. 42, SEQ ID NO. 43 or SEQ ID NO. 44 and each X of the pentapeptide repeats is composed of A (Ala), G (Gly), and I (Ile) in a ratio of 1:4:1 or in Formula 2, n is 12, and the pentapeptide repeats correspond to [SEQ ID NO. 45] and each X of the pentapeptide repeats is composed of E (Glu), G (Gly), and I (Ile) in a ratio of 1:4:1.

The fusion polypeptide according to the present invention may further include a hydrophobic elastin-based polypeptide (hydrophobic EBP) linked to the hydrophilic EBP.

That is, the fusion polypeptide may include of the following:

a peptide specifically binding to vascular endothelial growth factor (VEGF) receptors;

a hydrophilic elastin-based polypeptide (hydrophilic EBP) linked to the peptide; and a hydrophobic elastin-based polypeptide (hydrophobic EBP) linked to the hydrophilic EBP.

The hydrophobic EBP may include an amino acid sequence represented by Formula 1 or 2 below:

```
Formula 1
                                        [SEQ ID NO. 1]
n; or

Formula 2
                                        [SEQ ID NO. 2]
n, wherein

SEQ ID NO. 1 is consisted of
[VPGXG VPGXG VPGXG VPGXG VPGXG VPGXG];

SEQ ID NO. 2 is consisted of
[VPAXG VPAXG VPAXG VPAXG VPAXG VPAXG];
``` n is an integer of 1 or more, and represents the number of repeats of SEQ ID NO. 1 or SEQ ID NO. 2; and X is an amino acid other than proline, is selected from any natural or artificial amino acid when the pentapeptide VPGXG or VPAXG is repeated, and at least one of X is a hydrophobic or aliphatic amino acid.

The hydrophobic EBP may be consisted of an amino acid sequence represented by Formula 1 or 2 below:

in Formula 1, n is 1, and each X of the pentapeptide repeats is consisted of,

G (Gly), A (Ala), and F (Phe) in a ratio of 1:3:2 [SEQ ID NO. 29];

K (Lys), A (Ala), and F (Phe) in a ratio of 1:3:2 [SEQ ID NO. 30];

D (Asp), A (Ala), and F (Phe) in a ratio of 1:3:2 [SEQ ID NO. 31];

K (Lys) and F (Phe) in a ratio of 3:3 [SEQ ID NO. 32];

D (Asp) and F (Phe) in a ratio of 3:3 [SEQ ID NO. 33];

H (His), A (Ala), and I (Ile) in a ratio of 3:2:1 [SEQ ID NO. 34];

H (His) and G (Gly) in a ratio of 5:1 [SEQ ID NO. 35]; or

G (Gly), C (Cys), and F (Phe) in a ratio of 1:3:2 [SEQ ID NO. 36].

The hydrophobic EBP may include an amino acid sequence represented by Formula 2 below:

in Formula 2, n is 12, and each X of the pentapeptide repeats is consisted of G (Gly), A (Ala), and F (Phe) in a ratio of 1:3:2 [SEQ ID NO. 46], or in Formula 2, n is 24, and each X of the pentapeptide repeats is consisted of G (Gly), A (Ala), and F (Phe) in a ratio of 1:3:2 [SEQ ID NO. 47].

In one embodiment, the fusion polypeptide of the present invention may be composed of an amino acid sequence corresponding to SEQ ID NO. 48, SEQ ID NO. 49, SEQ ID NO. 50 or SEQ ID NO. 51. That is, the fusion polypeptide may be represented as follows:

the fusion polypeptide includes, an anti-Flt1 peptide; and a hydrophilic EBP $[A_1G_4I_1]_3$ linked to the anti-Flt1 peptide, and represented by [SEQ ID NO. 48];

an anti-Flt1 peptide; and a hydrophilic EBP $[A_1G_4I_1]_6$ linked to the anti-Flt1 peptide, and represented by [SEQ ID NO. 49];

an anti-Flt1 peptide; and a hydrophilic EBP $[A_1G_4I_1]_{12}$ linked to the anti-Flt1 peptide, and represented by [SEQ ID NO. 50]; or an anti-Flt1 peptide; and a hydrophilic EBP $[A_1G_4I_1]_{24}$ linked to the anti-Flt1 peptide, and represented by [SEQ ID NO. 51].

In another embodiment, the fusion polypeptide of the present invention may include an amino acid sequence corresponding to SEQ ID NO. 52 or SEQ ID NO. 53. That is, the fusion polypeptide may be represented as follows:

the fusion polypeptide includes, an anti-Flt1 peptide; a hydrophilic EBP $[E_1G_4I_1]_{12}$; and a hydrophobic EBP $[G_1A_3F_2]_{12}$, and represented by [SEQ ID NO. 52]; or an anti-Flt1 peptide; a hydrophilic EBP $[E_1G_4I_1]_{12}$; and a hydrophobic EBP $[G_1A_3F_2]_{24}$, and represented by [SEQ ID NO. 53].

According to the present invention, the fusion polypeptide composed of a VEGF receptor-specific peptide; a hydrophilic EBP; and a hydrophobic EBP may form a self-assembled nanostructure having a core-shell structure, when the hydrophobic EBP forms a core structure and the hydrophilic EBP and the VEGF receptor-specific peptide form a shell structure by a temperature stimulus.

The self-assembled nanostructure may include a multivalent VEGF receptor-specific peptide as a shell.

Specifically, an anti-Flt1 peptide which is a VEGF receptor-specific peptide is exemplified. A fusion polypeptide composed of an anti-Flt1 peptide; a hydrophilic EBP; and a hydrophobic EBP may form a self-assembled nanostructure having a core-shell structure, when the hydrophobic EBP forms a core structure and the hydrophilic EBP and the anti-Flt1 peptide form a shell structure by a temperature stimulus.

The self-assembled nanostructure may include a multivalent anti-Flt1 peptide as a shell, which provides greatly enhanced binding affinity to VEGF receptors.

According to another aspect of the present invention, there is provided a composition for treating diseases caused by neovascularization, including the fusion polypeptide.

According to still another aspect of the present invention, there is provided a method of inhibiting neovascularization in individuals, including a step of administering the therapeutic composition to individuals.

When a fusion polypeptide composed of a VEGF receptor-specific peptide; and a hydrophilic EBP is exemplified, the VEGF receptor-specific peptide of the fusion polypeptide may be non-covalently bound to a VEGF receptor to inhibit neovascularization (FIGS. 5A to 5D).

In addition, an example of a fusion polypeptide composed of a VEGF receptor-specific peptide; a hydrophilic EBP; and a hydrophobic EBP is as follows.

The fusion polypeptide may form a self-assembled nanostructure having a core-shell structure, when the hydrophobic EBP forms a core structure and the hydrophilic EBP and the VEGF receptor-specific peptide form a shell structure by a temperature stimulus, and the self-assembled nanostructure may include a multivalent VEGF receptor-specific peptide as a shell, whereby binding affinity between the self-assembled nanostructure and a VEGF receptor increases, and VEGF fails to bind to the VEGF receptor, thereby inhibiting neovascularization.

The diseases caused by neovascularization may be any one or more selected from the group comprising diabetic retinopathy, retinopathy of prematurity, macular degeneration, choroidal neovascularization, neovascular glaucoma, eye diseases caused by corneal neovascularization, corneal transplant rejection, corneal edema, corneal opacity, cancer, hemangioma, hemangiofibroma, rheumatoid arthritis, and psoriasis, but are necessarily limited thereto.

The term "vascular endothelial growth factor (VEGF)" used in the present invention refers to a factor that stimulates new blood vessel formation. VEGF binds to VEGF receptors to deliver a growth signal to vascular endothelial cells, which in turn triggers neovascularization.

The fusion polypeptide of the present invention functions to prevent VEGF from binding to VEGF receptors.

The term "amino acid" used in the present invention refers to a natural or artificial amino acid, preferably a natural amino acid. For example, the amino acid includes glycine, alanine, serine, valine, leucine, isoleucine, methionine, glutamine, asparagine, cysteine, histidine, phenylalanine, arginine, tyrosine, tryptophan and the like.

The properties of these amino acids are well known in the art. Specifically an amino acid exhibits hydrophilicity (negative or positive charge) or hydrophobicity, and also exhibits aliphatic or aromatic properties.

As used herein, abbreviations such as Gly (G) and Ala (A) are amino acid abbreviations. Gly is an abbreviation for glycine, and Ala is an abbreviation for alanine. In addition, glycine is represented by G and alanine by A. The abbreviations are widely used in the art.

In the present invention, "hydrophilic amino acid" is an amino acid exhibiting hydrophilic properties, and includes lysine, arginine and the like.

In addition, "hydrophobic amino acid" is an amino acid exhibiting hydrophobic properties, and includes phenylalanine, leucine and the like.

The term "polypeptide" used herein refers to any polymer chain composed of amino acids. The terms "peptide" and "protein" may be used interchangeably with the term polypeptide, and also refer to a polymer chain composed of amino acids. The term "polypeptide" includes natural or synthetic proteins, protein fragments and polypeptide analogs having protein sequences. A polypeptide may be a monomer or polymer.

The term "phase transition" refers to a change in the state of a material, such as when water turns into water vapor or ice turns into water.

The polypeptide according to the present invention is basically an elastin-based polypeptide (EBP) with stimuli-responsiveness. The "elastin-based polypeptide" is also called "elastin-like polypeptide (ELP)". The term is widely used in the technical field of the present invention.

In the present specification, $X_{aa}$ (or X) refers to a "guest residue". Various types of EBPs according to the present invention may be prepared by variously introducing $X_{aa}$.

EBP undergoes a reversible phase transition at a lower critical solution temperature (LCST), also referred to as a transition temperature ($T_t$). EBPs are highly water-soluble below $T_t$, but become insoluble when temperature exceeds $T_t$.

In the present invention, the physicochemical properties of EBPs are mainly controlled by combination of a pentapeptide repeat unit Val-Pro-(Gly or Ala)-$X_{aa}$-Gly. Specifically, the third amino acid of the repeat unit is responsible for determining the relative mechanical properties of the EBPs. For example, according to the present invention, the third amino acid Gly is responsible for determining elasticity, or Ala is responsible for determining plasticity. Elasticity and plasticity are properties that appear after a phase transition occurs.

In addition, the hydrophobicity of a guest residue $X_{aa}$, the fourth amino acid, and multimerization of a pentapeptide repeat unit all affect $T_t$.

The EBP according to the present invention may be a polypeptide composed of pentapeptide repeats, and a polypeptide block, i.e., an EBP block, may be formed when the polypeptide is repeated. Specifically, a hydrophilic or hydrophobic EBP block may be formed. The hydrophilic or hydrophobic properties of an EBP block according to the present invention are closely related to the transition temperature of the EBP.

The transition temperature of the EBP is also determined by the amino acid sequence of the EBP and the molecular weight thereof. A number of studies on the relationship between an EBP sequence and $T_t$ have been conducted by Urry et al (see Urry D. W., Luan C.-H., Parker T. M., Gowda D. C., Parasad K. U., Reid M. C., and Safavy A. 1991. TEMPERATURE OF POLYPEPTIDE INVERSE TEMPERATURE TRANSITION DEPENDS ON MEAN RESIDUE HYDROPHOBICITY. J. Am. Chem. Soc. 113: 4346-4348.). According to the above reference, when, in a pentapeptide of Val-Pro-Gly-Val-Gly, the fourth amino acid, a "guest residue", is replaced with a residue that is more hydrophilic than Val, $T_t$ is increased compared to the original sequence. On the other hand, when the guest residue is replaced with a residue that is more hydrophobic than Val, $T_t$ is decreased compared to the original sequence. That is, it was found that a hydrophilic EBP has a high $T_t$ and a hydrophobic EBP has a relatively low $T_t$. Based on these findings, it has become possible to prepare an EBP having a specific $T_t$ by determining which amino acid is used as the guest residue of an EBP sequence and changing the composition ratio of the guest residue (see PROTEIN-PROTEIN INTERACTIONS: A MOLECULAR CLONING MANUAL, 2002, Cold Spring Harbor Laboratory Press, Chapter 18. pp. 329-343).

As described above, an EBP exhibits hydrophilicity when the EBP has a high $T_t$, and hydrophobicity when the EBP has a low $T_t$. Similarly, in the case of the EBP block according to the present invention, it is also possible to increase or decrease $T_t$ by changing an amino acid sequence including guest residues and a molecular weight thereof. Thus, a hydrophilic or hydrophobic EBP block may be prepared.

For reference, an EBP having $T_t$ lower than a body temperature may be used as a hydrophobic block, whereas an EBP having $T_t$ higher than a body temperature may be used as a hydrophilic block. Due to this property of EBPs, the hydrophilic and hydrophobic properties of EBPs may be relatively defined when EBPs are applied to biotechnology.

Taking EBP sequences according to the present invention as an example, when a plastic polypeptide block in which a plastic pentapeptide of Val-Pro-Ala-$X_{aa}$-Gly is repeated is compared with an elastic polypeptide block in which an elastic pentapeptide of Val-Pro-Gly-$X_{aa}$-Gly is repeated, the third amino acid, Gly, has higher hydrophilicity than Ala. Accordingly, the plastic polypeptide block (elastin-based polypeptide with plasticity: EBPP) exhibits a lower $T_t$ than the elastic polypeptide block (elastin-based polypeptide with elasticity: EBPE).

EBPs according to the present invention, as described above, may exhibit hydrophilic or hydrophobic properties by adjusting $T_t$ and may be charged using charged amino acids.

Fusion polypeptides according to the present invention is schematically shown in FIGS. 5b and 5c. According to the present invention, an EBP was fused to an anti-Flt1 peptide that specifically binds to VEGF receptors (VEGFRs). Using the fusion polypeptide of the present invention, VEGF does not bind to VEGFRs, and thus neovascularization may be inhibited.

The term "EBP diblock" used herein refers to a block composed of "hydrophilic EBP-hydrophobic EBP", and is also called "EBP diblock copolymer", "EBP diblock block", "diblock EBP" "diblock EBPs" or "diblock EBPPs".

The present invention relates to a new class of genetically encoded "stimuli-responsive VEGFR-targeting fusion polypeptides".

In one embodiment, specifically, the fusion polypeptide is composed of an anti-Flt1 peptide acting as a receptor antagonist targeting VEGFR1 and a hydrophilic EBP block as a soluble unimer.

In another embodiment, the fusion polypeptide is composed of an anti-Flt1 peptide acting as a receptor antagonist targeting VEGFR1; a hydrophilic EBP block; and a hydrophobic EBP block. The EBP diblock of the hydrophilic EBP block and the hydrophobic EBP block contributes to the formation of a temperature-triggered core-shell micellar structure.

When using a fusion polypeptide composed of an anti-Flt1 peptide and a hydrophilic EBP block, a strong non-covalent interaction between VEGFR1 and the anti-Flt1 peptide domain of the fusion polypeptide occurs.

In addition, a fusion polypeptide composed of an anti-Flt1 peptide; a hydrophilic EBP block; and a hydrophobic EBP block may form a temperature-triggered core-shell micellar structure with a multivalent anti-Flt1 peptide under physiological conditions, which may increase the binding affinity of the fusion polypeptide for VEGFR1.

Therefore, the fusion polypeptide of the present invention may be presented as a polypeptide drug for treating neovascularization-related diseases.

The fusion polypeptide of the present invention may overcome the following limitations that arise when conventional peptide drugs and peptide-polymer conjugates are applied to in vivo treatment: (1) rapid clearance by proteases; (2) time consuming and costly conjugation and purification; (3) random distribution and (appearing upon polymerization of various polymers and peptide drugs) inconsistent conjugation efficiency; and (4) heterogeneous micellar structures due to polydisperse molecular weights thereof.

The present invention provides a VEGFR-targeting fusion polypeptide composed of thermally responsive elastin-based polypeptides (EBPs) and a vascular endothelial growth factor receptor (VEGFR)-targeting peptide. The fusion polypeptide of the present invention was genetically engineered, expressed and purified, and the physicochemical properties thereof were analyzed. The EBPs were introduced as non-chromatographic purification tags and were also introduced as a stabilizer, like a poly(ethylene glycol) conjugate, for minimizing rapid in vivo degradation of VEGFR1-targeting peptides. In addition, the VEGFR-targeting peptide was introduced to function as a receptor antagonist by specifically binding to VEGFRs. A fusion polypeptide composed of a VEGFR-targeting peptide-hydrophilic EBP block exhibited a soluble unimer form. On the other hand, a fusion polypeptide composed of VEGFR-targeting peptide-hydrophilic EBP block-hydrophobic EBP block exhibited a temperature-triggered core-shell micellar structure with a multivalent VGFR-targeting peptide under physiological conditions. As analyzed by enzyme-linked immunosorbent assay (ELISA), these structures increased the binding affinity of a fusion polypeptide for VEGF receptors (see Examples below). Depending on the spatial display of a VEGFR-targeting peptide, the binding affinity of the VEGFR-targeting peptide to VEGFRs was greatly regulated. The present invention shows how the binding affinity of a VEGFR-targeting peptide can be regulated based on multivalency.

A therapeutic composition including a fusion polypeptide for inhibiting neovascularization according to the present invention is a pharmaceutical composition. The pharmaceutical composition may include the fusion polypeptide and other materials that do not interfere with the function of the composition used in vivo for inhibiting neovascularization. Such other materials are not limited and may include diluents, excipients, carriers and/or other inhibitors of neovascularization.

In some embodiments, the fusion polypeptides for inhibiting neovascularization of the present invention are formulated for conventional human administration, for example, by formulating the fusion polypeptides with a suitable diluent, including sterile water and normal saline.

Administration or delivery of a therapeutic composition according to the present invention may be performed through any route so long as target tissues can be reached through that route. For example, the administration may be performed by direct injection into a target tissue (e.g., cardiac tissue) such as topical or intradermal, subcutaneous, intramuscular, intraperitoneal, intraarterial, intracoronary, intrathymic or intravenous injection, or intravitreal injection. The stability and/or potency of the fusion polypeptide disclosed in the present invention allow for convenient administration routes including subcutaneous, intradermal, intravenous and intramuscular routes.

The present invention provides a method of delivering a fusion polypeptide (e.g., as a part of a composition or formulation described herein) into cells, and a method of treating, alleviating, or preventing progression of a disease in a subject. The term "subject" or "patient" used in the present invention refers to any vertebrate animals, including, without being limited to, humans and other primates (e.g., chimpanzees and other apes and monkey species), farm animals (e.g., cows, sheep, pigs, goats and horses), domestic mammals (e.g., dogs and cats), laboratory animals (e.g., rodents such as mice, rats and guinea pigs) and birds (e.g., domestic, wild and game birds such as chickens, turkeys and poultry, ducks, geese, and the like). In some embodiments, the subject is a mammal.

In another embodiment, the mammal is a human.

A fusion polypeptide or pharmaceutical composition of the present invention may contact a target cell (e.g., a mammalian cell) in vitro or in vivo.

According to yet another aspect of the present invention, there is provided a method of treating or preventing diseases caused by neovascularization, the method including a step of administering a therapeutic composition according to the present invention to individuals.

For clinical use, the fusion polypeptide of the present invention may be administered alone via any suitable route of administration effective to achieve a desired therapeutic result or may be formulated into a pharmaceutical composition. The administration "route" of the oligonucleotides of the present invention may include enteral, parenteral and topical administration or inhalation. Among the administration routes of the fusion polypeptide of the present invention, enteral includes oral, gastrointestinal, intestinal, and rectal. Parenteral routes include ocular injection, intravenous, intraperitoneal, intramuscular, intraspinal, subcutaneous, topical, vaginal, topical, nasal, mucosal and pulmonary administration. The topical route of administration of the fusion polypeptides of the present invention refers to external application of the oligonucleotides into the epidermis, mouth and ears, eyes and nose.

The therapeutic composition may be administered by parenteral, oral, transdermal, sustained release, controlled release, delayed release, suppository, catheter or sublingual administration.

When the fusion polypeptide included in the therapeutic composition is administered in combination with other drugs, the fusion polypeptide may be administered in an amount of 15 µg/kg or less when injected intravenously, and may be administered in an amount of 2.5 µg or less when injected intravitreally.

The present invention is further illustrated by the following additional examples which should not be construed as limiting. It should be understood by those of ordinary skill in the art that various changes to the specific embodiments disclosed may be made without departing from the spirit and scope of the invention in the light of the present invention and that equivalent or similar results may be obtained.

Unless otherwise defined, all technical and scientific terms used herein have the same meaning as commonly understood by those of ordinary skill in the art to which this invention belongs. In general, the nomenclature used herein is well known and commonly used in the art.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 4A shows the profiles of EBPE$[A_1G_4I_1]_n$, FIG. 4B shows the profiles of EBPP $[A_1G_4I_1]_n$, FIG. 4C shows the profiles of EBPE$[K_1G_4I_1]_n$, FIG. 4D shows the profiles of EBPP$[K_1G_4I_1]_n$, FIG. 4E shows the profiles of EBPP$[D_1G_4I_1]_n$, and FIG. 4F shows the profiles of EBPP$[G_1A_3F_2]_n$. To obtain thermal profiles, 25 µM EBP solutions were prepared in PBS buffer or PBS buffer supplemented with 1 to 3 M sodium chloride, and the optical absorbance of the EBP solution was measured at 350 nm while heating the solution at a heating rate of 1° C./min;

In FIG. 5A genes encoding EBPP diblocks were constructed, and a gene encoding an anti-Flt1 peptide was cloned into a plasmid including a gene encoding an EBP diblock. In FIG. 5B fusion polypeptides composed of anti-Flt1 peptide-hydrophilic EBP; and anti-Flt1 peptide-hydrophilic EBP-hydrophobic EBP. In FIG. 5C fusion polypeptides composed of anti-Flt1 peptide-hydrophilic EBP-hydrophobic EBP were able to form a micellar structure by a temperature stimulus. In FIG. 5D (i) fusion polypeptides composed of anti-Flt1 peptide-hydrophilic EBP were able to bind to VEGFRs, and were able to inhibit interactions between VEGFR1 and VEGF. (ii) The micellar structures of fusion polypeptides composed of anti-Flt1 peptide-hydrophilic EBP-hydrophobic EBP were able to bind to VEGFRs, and was able to inhibit interactions between VEGFRs and VEGF with increased affinity due to the multivalency of the anti-Flt1 peptide;

DETAILED DESCRIPTION OF EXEMPLARY EMBODIMENTS

Example 1: Materials

Figure 1:
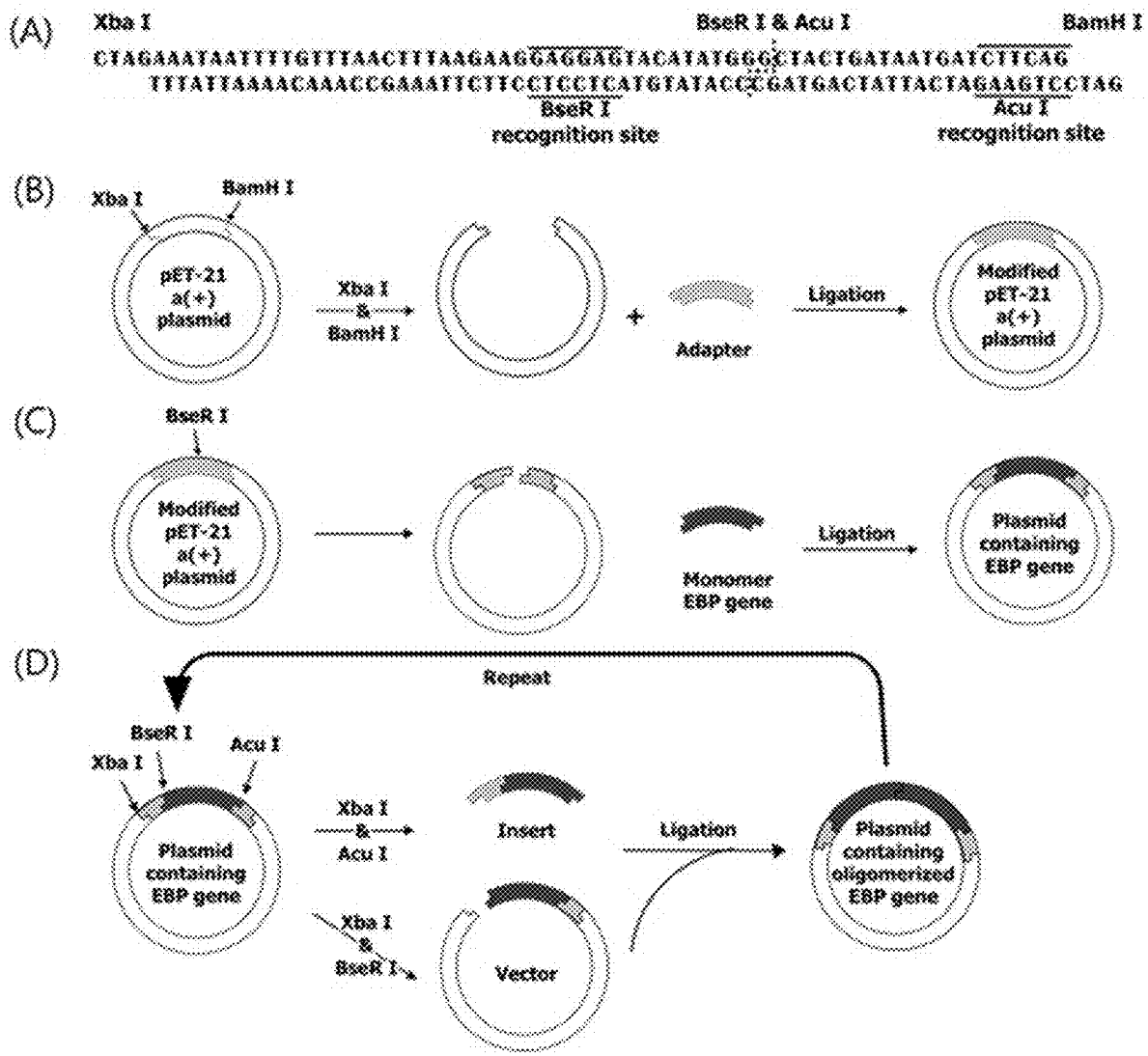
FIG. 1 illustrates a schematic diagram and an adapter sequence for construction of plasmids encoding EBP gene libraries with different DNA sizes. (A) an adapter sequence for modification of a pET-21a plasmid, (B) a scheme for modification of a pET-21a plasmid for seamless gene cloning, (C) a scheme for inserting a monomer EBP gene into a modified pET-21a vector, and (D) a scheme for construction of plasmids encoding EBP gene libraries with different DNA sizes.

A pET-21a (+) vector and BL21 (DE3) E. Coli cells were obtained from Novagen Inc. (Madison, Wis., U.S.). Top10 competent cells and calcein-AM were purchased from Invitrogen (Carlsbad, Calif., U.S.) and HUVECs were purchased from American Type Culture Collection (ATCC) (Virginia, U.S.). All customized oligonucleotides were synthesized by Cosmo GeneTech (Seoul, South Korea) and recombinant human VEGF-165 (rhVEGF$_{165}$) was obtained from Sino Biological Inc. (Beijing, China). Calf intestinal alkaline phosphatase (CIP), BamHI and XbaI were obtained from Fermentas (Ontario, Canada). AcuI and BseRI were purchased from New England Biolabs (Ipswich, Mass., U.S.). T4 DNA ligase was obtained from Elpis Bio-tech (Taejeon, South Korea). DNA miniprep, gel extraction, and PCR purification kits were obtained from Geneall Biotechnology (Seoul, South Korea). "Dyne Agarose High" was obtained from DYNE BIO, Inc. (Seongnam, South Korea). Top10 cells were grown in "TB DRY" media obtained from MO BIO Laboratories, Inc. (Carlsbad. Calif., U.S.). BL21 (DE3) cells were grown in "CircleGrow" media obtained from MP Biomedicals (Solon, Ohio, U.S.). "Ready Gels, Tris-HCl 2-20% precast gels" were from Bio-Rad (Hercules, Calif., U.S.). Phosphate buffered saline (PBS, pH 7.4), kanamycin, polyethyleneamine (PEI), FITC-dextran, formalin and bovine serum albumin (BSA) were obtained from Sigma-Aldrich (St Louis, Mo., U.S.). Matrigel was purchased from BD Biosciences (San Diego, Calif., U.S.). Avastin, also known as bevacizumab was purchased from Roche Pharma Ltd. (Reinach, Switzerland). Ketamine was obtained from Huons (Seongnam, South Korea). Xylazine was purchased from BAYER (Leverkusen, Germany). Tropicamide was purchased from Santen Pharmaceutical Co. Ltd (Kita-ku, Osaka, Japan). A stereomicroscope was obtained from Leica (Wetzlar, Germany). Recombinant human VEGF$_{165}$ protein and recombinant human VEGF R1/Flt-1 F$_c$ were purchased from R&D System (Minneapolis, Minn., U.S.). Rabbit anti-human IgG F$_c$-HRP chimeric protein and 3,3',5,5'-tetramethylbenzidine (TMB) was obtained from ThermoFisher (Massachusetts, U.S.).

Example 2: Notation for Different EBP Blocks and Block Polypeptides Thereof

Different EBPs having a pentapeptide repeat unit of Val-Pro-(Gly or Ala)-X$_{aa}$-Gly[VP (G or A)XG] are named as follows. X$_{aa}$ may be any amino acid except Pro. First, pentapeptide repeats of Val-Pro-Ala-X$_{aa}$-Gly (VPAXG) with plasticity are defined as an elastin-based polypeptide with plasticity (EBPP). On the other hand, pentapeptide repeats of Val-Pro-Gly-X$_{aa}$-Gly (VPGXG) are called elastin-based polypeptides with elasticity (EBPEs). Second, in [X$_i$Y$_j$Z$_k$]$_n$, the capital letters in the parentheses represent the single letter amino acid codes of guest residues, i.e., amino acids at the fourth position ($X_{aa}$ or X) of an EBP pentapeptide, and subscripts corresponding to the capital letters indicate the ratio of the guest residues in an EBP monomer gene as a repeat unit. The subscript number n of $[X_iY_jZ_k]_n$ represents the total number of repeats of an EBP corresponding to SEQ ID NO. 1 [VPGXG VPGXG VPGXG VPGXG VPGXG VPGXG] or SEQ ID NO. 2[VPAXG VPAXG VPAXG VPAXG VPAXG VPAXG] according to the present invention. For example, EBPP[$G_1A_3F_2]_{12}$ is an EBPP block including 12 repeats of a pentapeptide unit, SEQ ID NO. 2 [VPAXG VPAXG VPAXG VPAXG VPAXG VPAXG], in which a ratio of Gly, Ala, and Phe at the fourth guest residue position ($X_{aa}$) is 1:3:2. Finally, EBP-EBP diblock polypeptides are named according to the composition of each block in brackets with a hyphen between blocks as in EBPP [$E_1G_4I_1]_{12}$-EBPP[$G_1A_3F_2]_{12}$.

Example 3: Preparation of Modified pET-21a Vector for Cloning Seamless Gene

4 μg of a pET-21a vector was digested and dephosphorylated with 50 U of XbaI, 50 U of BamHI and 10 U of a thermosensitive alkaline phosphatase in FastDigest buffer for 20 minutes at 37° C. The digested plasmid DNA was purified using a PCR purification kit, and then was eluted in 40 μl of distilled and deionized water. Two oligonucleotides with XbaI and BamHI compatible sticky ends were designed, i.e., SEQ ID NO. 39 (5'-ctagaaataattttgtttaactt-taagaaggaggagtacatatgggctactgataatgatcttcag-3') and SEQ ID NO. 40 (5'-gatcctgaagatcattatcagtagcccatatgtactcctccttct-taaagttaaacaaaattattt-3'). To anneal the two types of oligonucleotides, each oligonucleotide was prepared at a concentration of 2 μM in 50 μl of T4 DNA ligase buffer, heat treated at 95° C. for 2 minutes and then slowly cooled to room temperature over 3 hours. To ligate the annealed dsDNA, i.e., a DNA insert, into multiple cloning sites within the linearized pET-21a vector, 20 pmol of the annealed dsDNA and 0.1 pmol of the linearized pET-21a vector were incubated in T4 DNA ligase buffer containing 1 U of T4 DNA ligase for 30 minutes at 37° C. The modified pET-21a (mpET-21a) vector for cloning and expressing a seamless gene was transformed into Top10 competent cells, followed by plating the Top10 competent cells on a super optimal broth with catabolite repression (SOC) plate supplemented with 50 μg/ml ampicillin. The DNA sequence of the mpET-21a vector was then verified by fluorescent dye terminator DNA sequencing (Applied Biosystems Automatic DNA Sequencer ABI3730).

Example 4: Synthesis of EBP Monomer Gene and Oligomerization Thereof

EBP sequences having a pentapeptide repeat unit, Val-Pro-(Gly or Ala)-$X_{aa}$-Gly, in which the fourth residues were varied in different molar ratios, were designed at the DNA level to optimize $T_t$ below a physiological temperature. The DNA and amino acid sequences of EBPs with various pentapeptide repeat units for 17 EBP libraries are shown in Tables 1 and 2, respectively.

TABLE 1

Gene sequences corresponding to EBP libraries. Both EBPs with plasticity (EBPPs) having a pentapeptide repeat of Val-Pro-Ala-$X_{aa}$-Gly, and EBPs with elasticity (EBPEs) having a pentapeptide repeat of Val-Pro-Gly-$X_{aa}$-Gly were cloned to have the same guest residue composition and ratio.

| EBP | Gene Sequence | SEQ ID NO. |
|---|---|---|
| EBPE[$A_1G_4I_1$] | GTC CCA GGT GGA GGT GTA CCC GGC GCG GGT GTC CCA GGT GGA GGT<br>GTA CCT GGG GGT GGG GTC CCT GGT ATT GGC GTA CCT GGA GGC GGC | 3 |
| EBPP[$A_1G_4I_1$] | GTT CCA GCT GGC GGT GTA CCT GCT GCT GCT GTT CCG GCC GGT GGT<br>GTT CCG GCG GGC GGC GTG CCT GCA ATA GGA GTT CCC GCT GGT GGC | 4 |
| EBPE[$K_1G_4I_1$] | GTT CCG GGT GGT GGT GTT CCG GGT AAA GGT GTT CCG GGT GGT GGT<br>GTT CCG GGT GGT GGT GGT GTT CCG GGT ATC GGT GTT CCG GGT GGC | 5 |
| EBPP[$K_1G_4I_1$] | GTT CCG GCG GGT GGT GTT CCG GCG AAA GGT GTT CCG GCG GGT GGT<br>GTT CCG GCG GGT GGT GTT CCG GCG ATC GGT GTT CCG GCG GGT GGC | 6 |
| EBPE[$D_1G_4I_1$] | GTT CCG GGT GGT GGT GTT CCG GGT GAT GGT GTT CCG GGT GGT GGT<br>GTT CCG GGT GGT GGT GGT GTT CCG GGT ATC GGT GTT CCG GGT GGC | 7 |
| EBPP[$D_1G_4I_1$] | GTT CCG GCG GGT GGT GTT CCG GCG GAT GGT GTT CCG GCG GGT GGT<br>GTT CCG GCG GGT GGT GTT CCG GCG ATC GGT GTT CCG GCG GGT GGC | 8 |
| EBPE[$E_1G_4I_1$] | GTT CCG GGT GGT GGT GTT CCG GGT GAA GGT GTT CCG GGT GGT GGT<br>GTT CCG GGT GGT GGT GGT GTT CCG GGT ATC GGT GTT CCG GGT GGC | 9 |
| EBPP[$E_1G_4I_1$] | GTT CCG GCG GGT GGT GTT CCG GCG GAA GGT GTT CCG GCG GGT GGT<br>GTT CCG GCG GGT GGT GTT CCG GCG ATC GGT GTT CCG GCG GGT GGC | 10 |
| EBPE[$G_1A_3F_2$] | GTC CCG GGT GCG GGC GTG CCG GGA TTT GGA GTT CCG GGT GCG GGT<br>GTT CCA GGC GGT GGT GTT CCG GGC GCG GGC GTG CCG GGC TTT GGC | 11 |
| EBPP[$G_1A_3F_2$] | GTG CCG GCG GCG GGC GTT CCA GCC TTT GGT GTG CCA GCG GCG GGA<br>GTT CCG GCC GGT GGC GTG CCG GCA GCG GGC GTG CCG GCT TTT GGC | 12 |
| EBPP[$K_1A_3F_2$] | GTG CCG GCG GCG GGC GTT CCA GCC TTT GGT GTG CCA GCG GCG GGA<br>GTT CCG GCC AAA GGC GTG CCG GCA GCG GGC GTG CCG GCT TTT GGC | 13 |

TABLE 1-continued

Gene sequences corresponding to EBP libraries. Both EBPs with plasticity (EBPPs) having a pentapeptide repeat of Val-Pro-Ala-$X_{aa}$-Gly, and EBPs with elasticity (EBPEs) having a pentapeptide repeat of Val-Pro-Gly-$X_{aa}$-Gly were cloned to have the same quest residue composition and ratio.

| EBP | Gene Sequence | SEQ ID NO. |
|---|---|---|
| EBPP[$D_1A_3F_2$] | GTG CCG GCG GCG GGC GTT CCA GCC TTT GGT GTG CCA GCG GCG GGA<br>GTT CCG GCC GAT GGC GTG CCG GCA GCG GGC GTG CCG GCT TTT GGC | 14 |
| EBPP[$K_3F_3$] | GTT CCA GCG TTT GGC GTG CCA GCG AAA GGT GTT CCG GCG TTT GGG<br>GTT CCC GCG AAA GGT GTG CCG GCC TTT GGT GTG CCG GCC AAA GGC | 15 |
| EBPP[$D_3F_3$] | GTT CCA GCG TTT GGC GTG CCA GCG GAT GGT GTT CCG GCG TTT GGG<br>GTT CCC GCG GAT GGT GTG CCG GCC TTT GGT GTG CCG GCC GAT GGC | 16 |
| EBPP[$H_3A_3I_1$] | GTG CCG GCG CAT GGA GTT CCT GCC GCC GGT GTT CCT GCG CAT GGT<br>GTA CCG GCA ATT GGC GTT CCG GCA CAT GGT GTG CCG GCC GCC GGC | 17 |
| EBPP[$H_5G_1$] | GTT CCG GCC GGA GGT GTA CCG GCG CAT GGT GTT CCG GCA CAT GGT<br>GTG CCG GCT CAC GGT GTG CCT GCG CAT GGC GTT CCT GCG CAT GGC | 18 |
| EBPP[$G_1C_3F_2$] | GTG CCG GCG TGC GGC GTT CCA GCC TTT GGT GTG CCA GCG TGC GGA<br>GTT CCG GCC GGT GGC GTG CCG GCA TGC GGC GTG CCG GCT TTT GGC | 19 |

TABLE 2

Amino acid sequences corresponding to EBP libraries

| EBP | Amino acid Sequence | SEQ ID NO. |
|---|---|---|
| EBPE[$A_1G_4I_1$] | VPGGG VPGAG VPGGG VPGGG VPGIG VPGGG | 20 |
| EBPP[$A_1G_4I_1$] | VPAGG VPAAG VPAGG VPAGG VPAIG VPAGG | 21 |
| EBPE[$K_1G_4I_1$] | VPGGG VPGKG VPGGG VPGGG VPGIG VPGGG | 22 |
| EBPP[$K_1G_4I_1$] | VPAGG VPAKG VPAGG VPAGG VPAIG VPAGG | 23 |
| EBPE[$D_1G_4I_1$] | VPGGG VPGDG VPGGG VPGGG VPGIG VPGGG | 24 |
| EBPP[$D_1G_4I_1$] | VPAGG VPADG VPAGG VPAGG VPAIG VPAGG | 25 |
| EBPE[$E_1G_4I_1$] | VPGGG VPGEG VPGGG VPGGG VPGIG VPGGG | 26 |
| EBPP[$E_1G_4I_1$] | VPAGG VPAEG VPAGG VPAGG VPAIG VPAGG | 27 |
| EBPE[$G_1A_3F_2$] | VPGAG VPGFG VPGAG VPGGG VPGAG VPGFG | 28 |
| EBPP[$G_1A_3F_2$] | VPAAG VPAFG VPAAG VPAGG VPAAG VPAFG | 29 |
| EBPP[$K_1A_3F_2$] | VPAAG VPAFG VPAAG VPAGG VPAAG VPAFG | 30 |
| EBPP[$D_1A_3F_2$] | VPAAG VPAFG VPAAG VPAGG VPAAG VPAFG | 31 |
| EBPP[$K_3F_3$] | VPAFG VPAKG VPAFG VPAKG VPAFG VPAKG | 32 |
| EBPP[$D_3F_3$] | VPAFG VPADG VPAFG VPADG VPAFG VPADG | 33 |
| EBPP[$H_3A_3I_1$] | VPAHG VPAAG VPAHG VPAIG VPAHG VPAAG | 34 |
| EBPP[$H_5G_1$] | VPAGG VPAHG VPAHG VPAHG VPAHG VPAHG | 35 |
| EBPP[$G_1C_3F_2$] | VPACG VPAFG VPACG VPAGG VPACG VPAFG | 36 |

In Table 1, SEQ ID NO. 3 to 10 may be classified as gene sequences for hydrophilic EBP blocks, and SEQ ID NO. 11 to 19 may be classified as gene sequences for hydrophobic EBP blocks, in which Phe and His are incorporated. In Table 2, amino acid SEQ ID NO. 20 to 27 may be classified as hydrophilic EBP blocks, and amino acid SEQ ID NO. 28 to 36, in which Phe and His are incorporated, may be classified as hydrophobic EBP blocks. In particular, in Table 2, SEQ ID NO. 22 and 23 are classified as positively charged hydrophilic EBP blocks, and SEQ ID NO. 24 to 27 are classified as negatively charged hydrophilic EBP blocks. That is, as described above, when the LCST of an EBP is lower than the body temperature, the EBP exhibits hydrophobicity, and when the LCST of an EBP is higher than the body temperature, the EBP exhibits hydrophilicity. Due to this nature of EBPs, the hydrophilic and hydrophobic properties of EBPs may be relatively defined when EBPs are applied to biotechnology.

Different EBPs having a pentapeptide repeat unit, Val-Pro-(Gly or Ala)-$X_{aa}$-Gly [where $X_{aa}$ may be any amino acid except Pro], which are capable of responding to unique stimuli including temperature and pH, were designed at the DNA level. EBPs with plasticity (EBPPs) having a pentapeptide repeat unit of Val-Pro-Ala-$X_{aa}$-Gly and EBPs with elasticity (EBPEs) having a pentapeptide repeat unit of Val-Pro-Gly-$X_{aa}$-Gly were all cloned to have the same guest residue composition and ratio. Tables 1 and 2 represent the gene and amino acid sequences of different EBPs having respective pentapeptide units. For example, EBPE[$G_1A_3F_2$]$_{12}$ and EBPP[$G_1A_3F_2$]$_{12}$ not only show almost the same molar mass, but also the fourth residues of these EBP pentapeptide units represent the same combination. In addition, these EBP blocks have different mechanical properties because the third amino acid residues (Ala or Gly) of the pentapeptide units are different. Positively and negatively charged EBPs were prepared by introducing charged amino acids such as Lys, Asp, Glu, and His as guest residues.

To anneal each pair of oligonucleotides encoding various EBPs, each oligonucleotide was prepared at a concentration of 2 µM in 50 µl of T4 DNA ligase buffer, heat treated at 95° C. for 2 minutes and then slowly cooled to room temperature over 3 hours. 4 µg of a modified pET-21a vector was digested and dephosphorylated with 15 U of BseRI and 10 U of FastAP thermosensitive alkaline phosphatase for 30 minutes at 37° C. The digested plasmid DNA was purified using a PCR purification kit, and then was eluted in 40 µl of distilled and deionized water. To ligate the annealed dsDNA, i.e., a DNA insert, into multiple cloning sites within the linearized mpET-21a vector, 90 pmol of the annealed dsDNA and 30 pmol of the linearized mpET-21a vector were incubated in T4 DNA ligase buffer containing 1 U of T4 DNA ligase for 30 minutes at 16° C. The ligated plasmid was transformed into Top10 chemically competent cells, followed by plating the Top10 competent cells on an SOC plate supplemented with 50 µg/ml ampicillin. DNA sequences were then confirmed by DNA sequencing. After all EBP monomer genes were constructed, each EBP gene was synthesized by ligating each of 36 types of repetitive genes (as an insert) into the corresponding vector containing each of the same 36 types of repetitive genes, as follows. A cloning procedure for EBP libraries and fusions thereof are illustrated in FIG. 1. Vectors harboring gene copies corresponding to EBP monomers were digested and dephosphorylated with 10 U of XbaI, 15 U of BseRI and 10 U of FastAP thermosensitive alkaline phosphatase in CutSmart buffer for 30 minutes at 37° C. The digested plasmid DNA was purified using a PCR purification kit, and then was eluted in 40 µl of distilled and deionized water. For preparation of an insert part, a total of 4 µg of an EBP monomer gene was digested with 10 U of XbaI and 15 U of AcuI in CutSmart buffer for 30 minutes at 37° C. After digestion, the reaction product was separated by agarose gel electrophoresis and the insert was purified using a gel extraction kit. Ligation was performed by incubating 90 pmol of the purified insert with 30 pmol of the linearized vector in T4 DNA ligase buffer containing 1 U of T4 DNA ligase for 30 minutes at 16° C. The product was transformed into Top10 chemically competent cells, and then the cells were plated on an SOC plate supplemented with 50 µg/ml ampicillin Transformants were initially screened by diagnostic restriction digestion on an agarose gel and further confirmed by DNA sequencing as described above.

Figure 2:
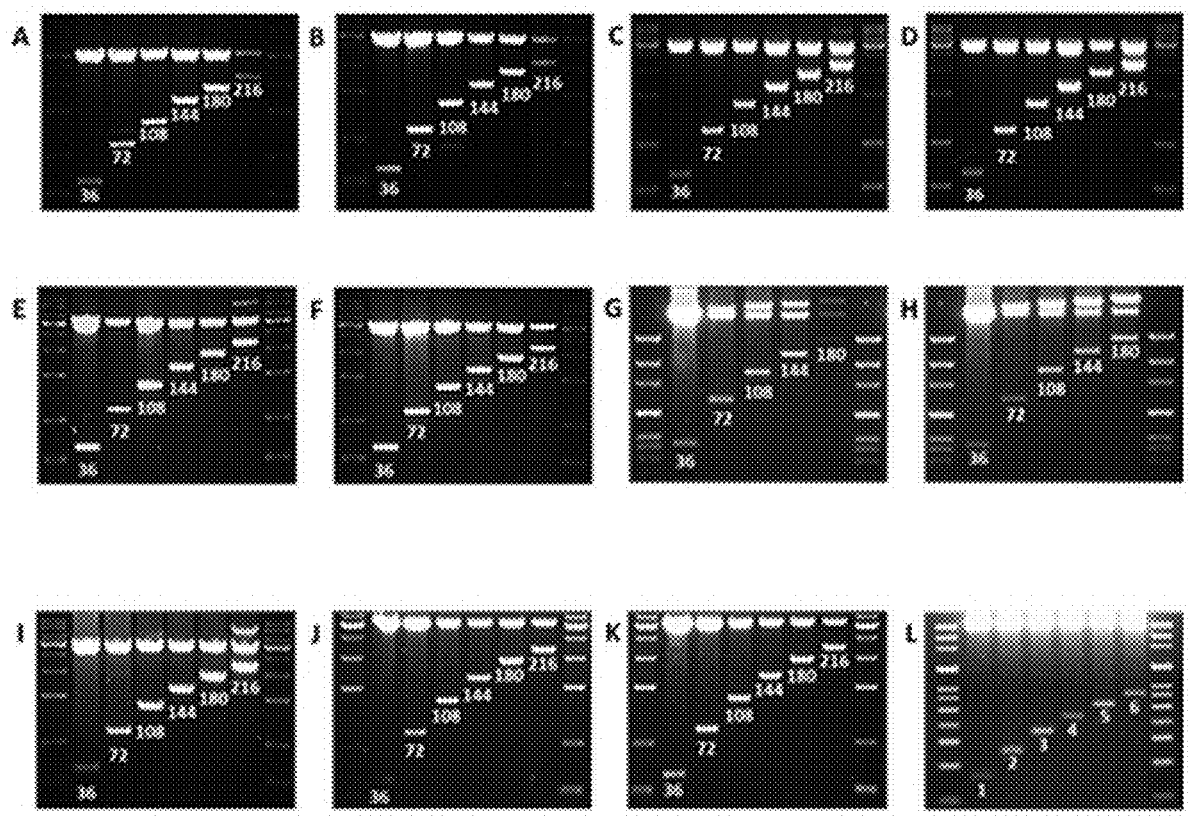
FIG. 2 shows the agarose gel electrophoresis images of EBP gene libraries used in the present invention. (A) EBPE $[A_1G_4I_1]$, (B) EBPP$[A_1G_4I_1]$, (C) EBPE$[K_1G_4I_1]$, (D) EBPP$[K_1G_4I_1]$, (E) EBPE$[D_1G_4I_1]$, (F) EBPP$[D_1G_4I_1]$, (G) EBPE$[E_1G_4I_1]$, (H) EBPP$[E_1G_4I_1]$, (I) EBPP$[G_1A_3F_2]$, (J) EBPP$[K_1A_3F_2]$, (K) EBPP$[D_1A_3F_2]$, and (L) EBPP $[H_3A_2I_1]$. The number of EBP repeat units was indicated below each DNA band. Two side-lanes on all agarose gels represent different DNA size markers (0.1, 0.2, 0.3, 0.4, 0.5, 0.6, 0.7, 1.0, 1.5, 2.0, and 3.0 kbp, from bottom to top)

As described above, EBP gene libraries having different DNA sizes were synthesized using the designed plasmid vector and three different restriction endonucleases. FIG. 1 illustrates a recursive directional ligation (RDL) method, in which EBP monomer genes are ligated to form oligomerized EBP genes. For example, a gene construct encoding EBPP $[G_1A_3F_2]_{12}$ was prepared by ligation, wherein a plasmid backbone and an insert derived from a plasmid-borne gene vector harboring a gene encoding EBPP$[G_1A_3F_2]_6$ were used. The plasmid-borne gene vector harboring a gene encoding EBPP$[G_1A_3F_2]_6$ was double-digested by XbaI and AcuI to obtain an insert, i.e., a gene fragment encoding EBPP$[G_1A_3F_2]_6$. On the other hand, the plasmid-borne gene vector for EBPP$[G_1A_3F_2]_6$ was double-digested by XbaI and BseRI to obtain a plasmid backbone and then the plasmid backbone was dephosphorylated by treatment with an alkaline phosphatase. The RDL method using two different double restriction enzymes has several advantages. First, due to the different shapes of the protrusions of both an insert and a digested vector, self-ligation of the digested vector did not occur, and the insert and the digested vector were efficiently linked in a head-tail orientation. Second, due to the mechanism of type III restriction endonuclease, an additional DNA sequence encoding each linker between blocks is not required. Each EBP gene was oligomerized to generate 36, 72, 108, 144, 180, and 216 EBP pentapeptide repeats. Using two restriction endonucleases XbaI and BamHI, oligomerized genes with sizes of 540, 1080, 1620, 2160, 2700, and 3240 base pairs (bps) were confirmed. As characterized by agarose gel electrophoresis, FIG. 2 depicts the digested DNA bands of EBP libraries with DNA size markers on both end lanes. For example, EBPE$[A_1G_4I_1]$ in FIG. 2(A) clearly shows a digested DNA band corresponding to a DNA region encoding an oligomerized pentapeptide sequence containing Ala, Gly, Ile in a ratio of 1:4:1 as a guest residue. All digested DNA bands are shown as corresponding lengths as compared to the molecular size markers.

Figure 3:
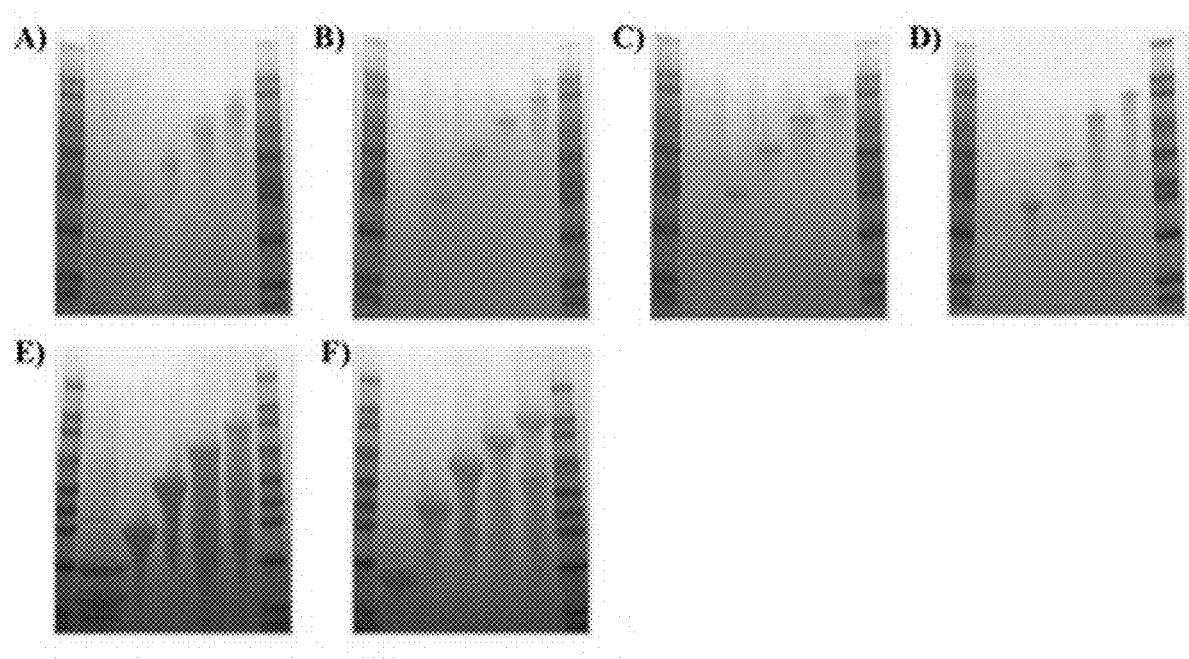
FIG. 3 shows the copper-stained SDS-PAGE gel (4 to 20% gradient) images of EBPs used in the present invention. (A) EBPE$[A_1G_4I_1]$, (B) EBPP$[A_1G_4I_1]$, (C) EBPE$[K_1G_4I_1]$, (D) EBPP$[K_1G_4I_1]$, (E) EBPE$[D_1G_4I_1]$ and (F) EBPP $[D_1G_4I_1]$. Two side-lanes on SDS-PAGE gels contain standard protein size markers (7, 15, 24, 35, 40, 50, 65, 90, 110, and 150 kDa, from bottom to top)

EBP genes and block co-polypeptides thereof were overexpressed in E. coli having a T7 promoter and purified by multiple cycles of inverse transition cycling (ITC). FIG. 3 shows copper-stained SDS-PAGE gel images of the purified EBPs. EBPs shifted at least 20% more than theoretically calculated molecular weights. Two side-lanes on SDS-PAGE gels contain standard protein size markers (7, 15, 24, 35, 40, 50, 65, 90, 110, and 150 kDa, from bottom to top). In FIGS. 3(A) and 3(B), EBPE$[A_1G_4I_1]$ and EBPP$[A_1G_4I_1]$ represent a series of corresponding proteins with a molecular weight greater than a theoretical molecular weight (for EBPE$[A_1G_4I_1]$, 14.0, 27.7, 41.3, 55.0, and 68.6 kDa, from left to right). In general, as shown in FIGS. 3(C) and 3(D), positively charged EBP libraries, including EBPE$[K_1G_4I_1]$ and EBPP$[K_1G_4I_1]$, showed higher molecular weights than nonpolar EBP libraries, including EBPE$[A_1G_4I_1]$ and EBPP$[A_1G_4I_1]$. In addition, as shown in FIGS. 3(E) and 3(F), negatively charged EBP libraries, including EBPE$[D_1G_4I_1]$ and EBPP$[D_1G_4I_1]$, have differently charged characteristics, and thus exhibited higher molecular weights than positively charged EBP libraries.

Figure 4A:
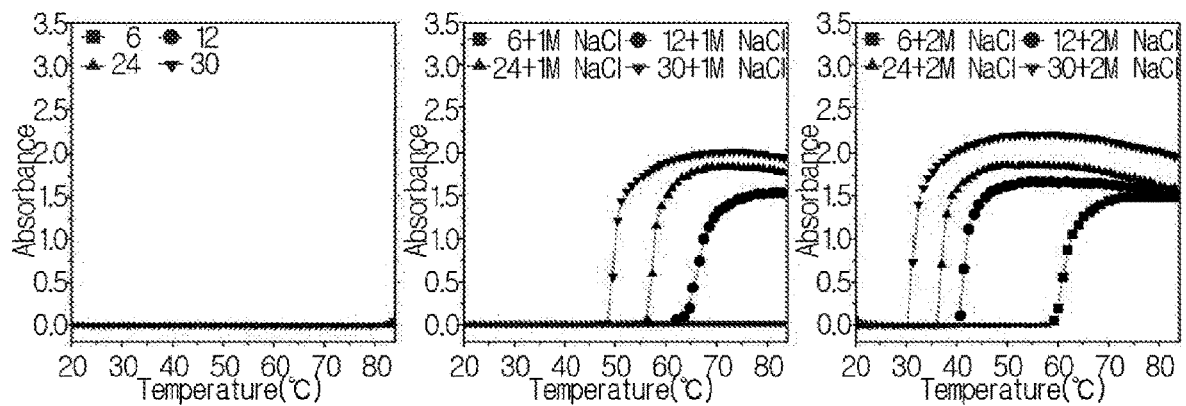
FIGS. 4A to 4F show the thermal profiles of EBPs used in the present invention.
Figure 4B:
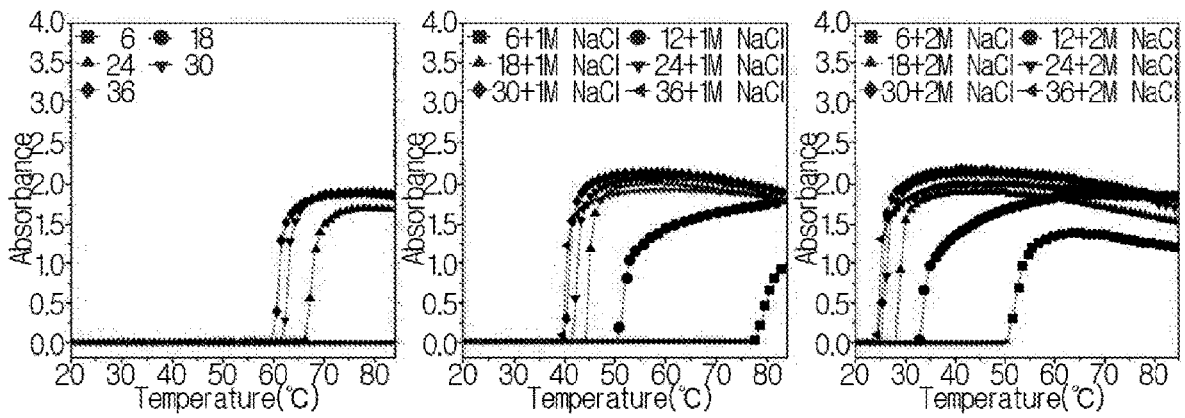
Figure 4C:
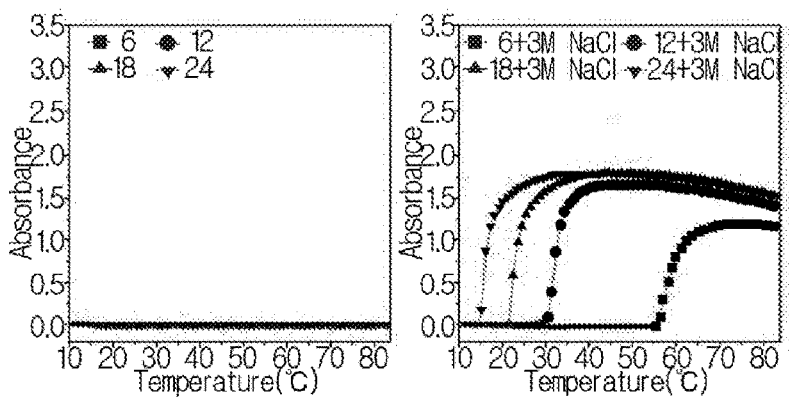
Figure 4D:
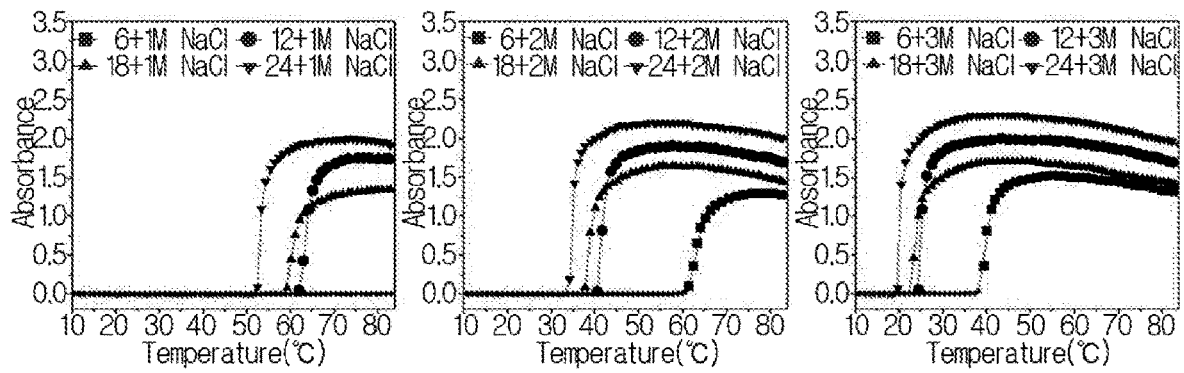
Figure 4E:
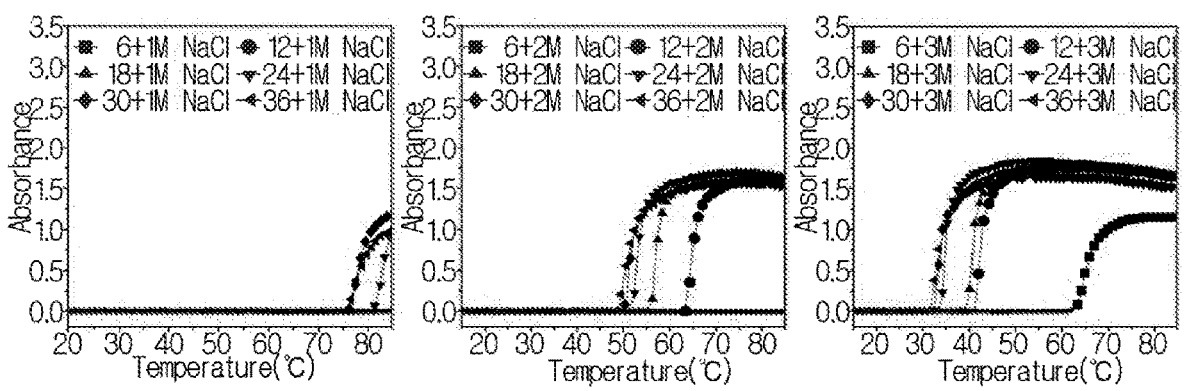
Figure 4F:
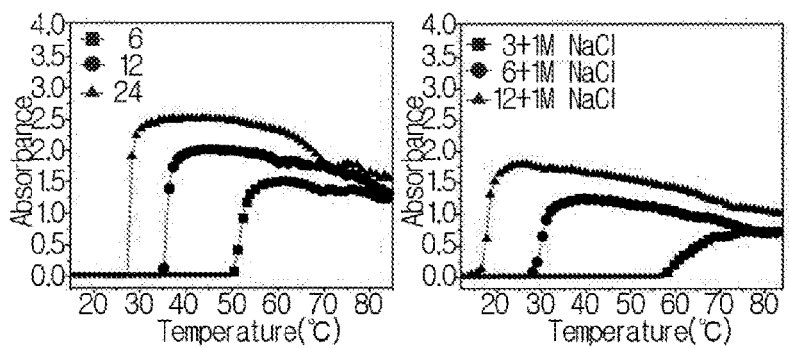

EBP libraries were characterized. FIGS. 4A to 4F show thermal transition behaviors of EBPs determined by measuring optical absorbance at 350 nm (absorbance$_{350}$) at a heating rate of 1° C./min Inverse transition temperature $(T_t)$ is defined as a temperature at which the first derivative (d $(OD_{350})$/dT) of turbidity, which is a function of temperature, was the maximum. Based on environmental conditions such as a salt concentration and pH and the different third and fourth amino acids of an EBP pentapeptide repeat unit, the $T_t$ of an EBP was finely controlled in PBS and PBS was supplemented with 1 to 3 M sodium chloride. For example, EBPE$[A_1G_4I_1]_{12}$ (FIG. 4A) with Gly at the third amino acid of an EBP pentapeptide repeat exhibited a $T_t$ about 15° C. higher than that of EBPP$[A_1G_4I_1]_{12}$ (FIG. 4B) with Ala at the third amino acid of an EBP pentapeptide repeat in PBS containing 1 M sodium chloride, because Gly at the third amino acid of an EBP pentapeptide repeat has a higher hydrophilicity than Ala. In general, charged EBP libraries have a higher $T_t$ than nonpolar EBP libraries because charged residues are introduced into the fourth amino acid of the EBP pentapeptide repeat of the charged EBPs. Negatively charged EBP libraries, such as EBPP$[D_1G_4I_1]$ (FIG. 4E), have different $pK_a$ values for Asp and Lys at the fourth amino acid of an EBP pentapeptide repeat, and thus have a higher $T_t$ than positively charged EBP libraries, such as EBPE$[K_1G_4I_1]$ (FIG. 4C) and EBPP$[K_1G_4I_1]$ (FIG. 4D). For reference, FIGS. 4A, 4B, 4C, 4D and 4E exhibit hydrophilicity, and FIG. 4F exhibits EBPP$[G_1A_3F_2]_{12}$ and EBPP $[G_1A_3F_2]_{24}$ exhibit hydrophobicity.

Example 5: Gene Construction of Anti-Flt1-EBPP $[A_1G_4I_1]$n and Anti-Flt1-EBP Diblock Block (Co-polypeptides)

A pair of oligonucleotides encoding an anti-Flt1 peptide acting as a VEGFR1 antagonist were chemically synthesized by Cosmo Genetech (Seoul, Korea), and linked to an oligonucleotide cassette with cohesive ends including restriction sites recognized by AcuI and BseRI. An oligonucleotide cassette encoding the anti-Flt1 peptide was rationally designed to have no restriction sites recognized by BseRI, XbaI, AcuI and BamHI for seamless gene cloning, as shown in Table 3.

TABLE 3

Gene and amino acid sequences of CPPs

| SEQ ID NO. | Sequence Type | Sequence |
|---|---|---|
| 37 | Gene Sequence | GGC AAT CAG TGG TTT ATT |
| 38 | Amino acid Sequence | G N Q W F I |

In Table 4, the sequences, gene lengths and molecular weights of fusion polypeptides with a hydrophilic EBP block or an EBP diblock of hydrophilic EBP block-hydrophobic EBP block are shown.

TABLE 4

Sequences, gene lengths and molecular weights of fusion polypeptides

| Fusion protein (SEQ ID NO.) | Nucleotide length (bp) | M.W (kDa) |
|---|---|---|
| Anti-Flt1-EBPP[$A_1G_4I_1$]$_3$ (SEQ ID NO. 48) | 288 | 8.19 |
| Anti-Flt1-EBPP[$A_1G_4I_1$]$_6$ (SEQ ID NO. 49) | 558 | 15.27 |
| Anti-Flt1-EBPP[$A_1G_4I_1$]$_{12}$ (SEQ ID NO. 50) | 1098 | 29.42 |
| Anti-Flt1-EBPP[$A_1G_4I_1$]$_{24}$ (SEQ ID NO. 51) | 2178 | 57.72 |
| Anti-Flt1-EBPP[$E_1G_4I_1$]$_{12}$-EBPP[$G_1A_3F_2$]$_{12}$ (SEQ ID NO. 52) | 2178 | 59.90 |
| Anti-Flt1-EBPP[$E_1G_4I_1$]$_{12}$-EBPP[$G_1A_3F_2$]$_{24}$ (SEQ ID NO. 53) | 3258 | 90.00 |

Each plasmid containing an EBP with restriction sites recognized by BseRI, XbaI, AcuI and BamHI, and the oligonucleotide cassette were used to create genes for the fusion polypeptide libraries of anti-Flt1-EBPP[$A_1G_4I_1$]$_3$ and anti-Flt1-EBP diblock blocks. First, to anneal a pair of oligonucleotides encoding an anti-Flt1 peptide, each oligonucleotide was prepared at a concentration of 2 μM in 50 μl of T4 DNA ligase buffer, heat treated at 95° C. for 2 minutes and then the reaction solution was slowly cooled to room temperature over 3 hours. To clone the anti-Flt1-EBPP [$A_1G_4I_1$]$_{3n}$, a plasmid vector encoding EBPP[$A_1G_4I_1$]$_{3n}$ was digested with 15 U of BseRI in CutSmart buffer for 30 minutes at 37° C. The digested plasmid DNA was purified using a PCR purification kit, and then dephosphorylated with 10 U of FastAP as a thermosensitive alkaline phosphatase in CutSmart buffer for 1 hour at 37° C. The digested and dephosphorylated plasmid DNA was purified using a PCR purification kit, and then eluted in 40 μl of distilled and deionized water. Ligation was performed by incubating 90 pmol of the purified insert and 30 pmol of the linearized vector in T4 DNA ligase buffer containing 1 U of T4 DNA ligase at 16° C. for 30 minutes. The product was transformed into Top10 chemically competent cells and the cells were plated on SOC plates supplemented with 50 μg/ml ampicillin Transformants were initially screened by diagnostic restriction digestion on an agarose gel and further confirmed by DNA sequencing as described above.

Similarly, to clone anti-Flt1-EBP diblock blocks with hydrophobic blocks of different lengths, plasmid vectors encoding EBPP[$G_1A_3F_2$]$_n$ were digested with 10 U of XbaI and 15 U of BseRI in CutSmart buffer for 30 minutes at 37° C. The digested plasmid DNA was purified using a PCR purification kit, and then dephosphorylated with 10 U of FastAP as a thermosensitive alkaline phosphatase in CutSmart buffer for 1 hour at 37° C. The digested and dephosphorylated plasmid DNA was purified using a PCR purification kit, and then eluted in 40 μl of distilled and deionized water. 4 μg of EBPP[$E_1G_4I_1$]$_n$ genes were digested with 10 U of XbaI and 15 U of AcuI in CutSmart buffer for 30 minutes at 37° C. After digestion, the reaction product was separated by agarose gel electrophoresis and an insert was purified using a gel extraction kit. Ligation was performed by incubating 90 pmol of the purified insert and 30 pmol of the linearized vector in T4 DNA ligase buffer containing 1 U of T4 DNA ligase at 16° C. for 30 minutes. The product was transformed into Top10 chemically competent cells and the cells were plated on SOC plates supplemented with 50 μg/ml ampicillin Transformants were initially screened by diagnostic restriction digestion on an agarose gel and further confirmed by DNA sequencing. Plasmid vectors encoding anti-Flt1-EBP diblock blocks were prepared using BseRI, and ligation and confirmation of ligation were performed as described above.

Example 6: Expression of Genes Encoding EBPs, Anti-Flt1-EBPP[$A_1G_4I_1$]$_{3n}$ and Anti-Flt1-EBP Diblock Block and Purification of Gene Expression Products E. coli strain BL21 (DE3) cells were transformed with each vector containing an EBP, anti-Flt1-EBPP[$A_1G_4I_1$]$_{3n}$ or an anti-Flt1-EBP diblock block, and then inoculated in 50 ml of CircleGrow media supplemented with 50 μg/ml ampicillin Preculture was performed in a shaking incubator at 200 rpm overnight at 37° C. 500 ml of CircleGrow media with 50 μg/ml ampicillin was then inoculated with 50 ml of the precultured CircleGrow media and incubated in a shaking incubator at 200 rpm for 16 hours at 37° C. When optical density at 600 nm ($OD_{600}$) reached 1.0, overexpression of an EBP gene or a block polypeptide gene thereof was induced by addition of IPTG at a final concentration of 1 mM. The cells were centrifuged at 4500 rpm for 10 minutes at 4° C. The expressed EBPs and block polypeptides thereof were purified by inverse transition cycling (ITC) as reported previously. The cell pellet was resuspended in 30 ml of HEPES buffer, and the cells were lysed by sonication for 10 s in 20 s intervals (VC-505, Sonics & Materials, Inc, Danbury, Conn.) on ice. The cell lysate was centrifuged in a 50 ml centrifuge tube at 13,000 rpm for 15 min at 4° C. to precipitate the insoluble debris of the cell lysate. Supernatant containing soluble EBPs was then transferred to a new 50 ml centrifuge tube and centrifuged with 0.5% w/v of PEI at 13,000 rpm for 15 minutes at 4° C. to precipitate nucleic acid contaminants. The inverse phase transition of the EBPs were triggered by adding sodium chloride at a final concentration of 4 M, and aggregated EBPs were separated from the lysate solution by centrifugation at 13,000 rpm for 15 minutes at 4° C. The aggregated EBPs were resuspended in cold PBS buffer, and the EBP solutions were centrifuged at 13,000 rpm for 15 minutes at 4° C. to remove any aggregated protein contaminants. These aggregation and resuspension processes were repeated 5 to 10 times until EBP purity reached about 95%, and the purity was determined by SDS-polyacrylamide gel electrophoresis (SDS-PAGE).

Figure 5A:
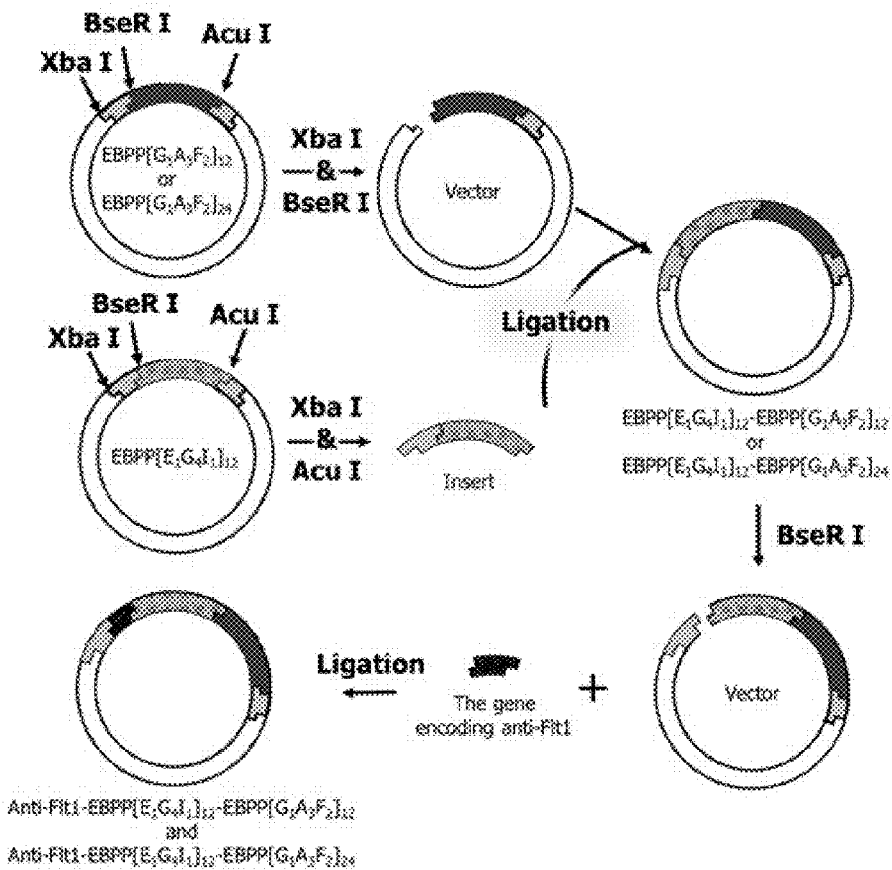
FIGS. 5A to 5D are schematic diagrams of cloning, molecular structures, and functions of fusion polypeptides composed of EBPPs and an anti-Flt1 peptide.
Figure 5B:
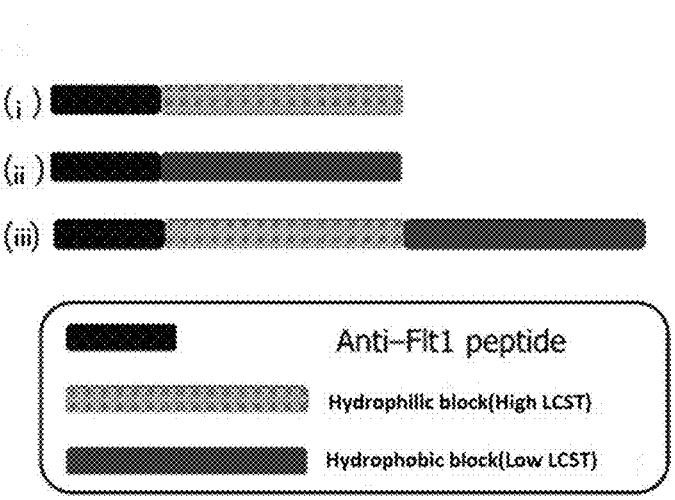
Figure 5C:
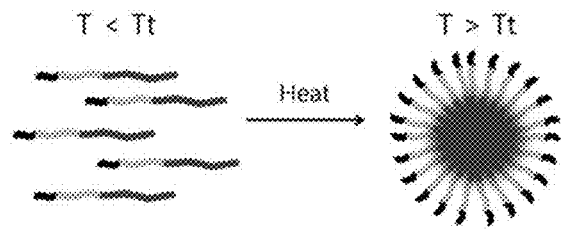

FIG. 5A to 5D show a schematic diagram of molecular design, cloning and the anti-neovascularization function of fusion polypeptides according to the present invention. As shown in FIG. 5C, a fusion polypeptide corresponding to VEGFR-targeting peptide (anti-Flt1 peptide)-hydrophilic EBP-hydrophobic EBP forms a temperature-triggered core-shell micellar structure with a multivalent VEGFR-targeting peptide under physiological conditions.

Figure 5D:
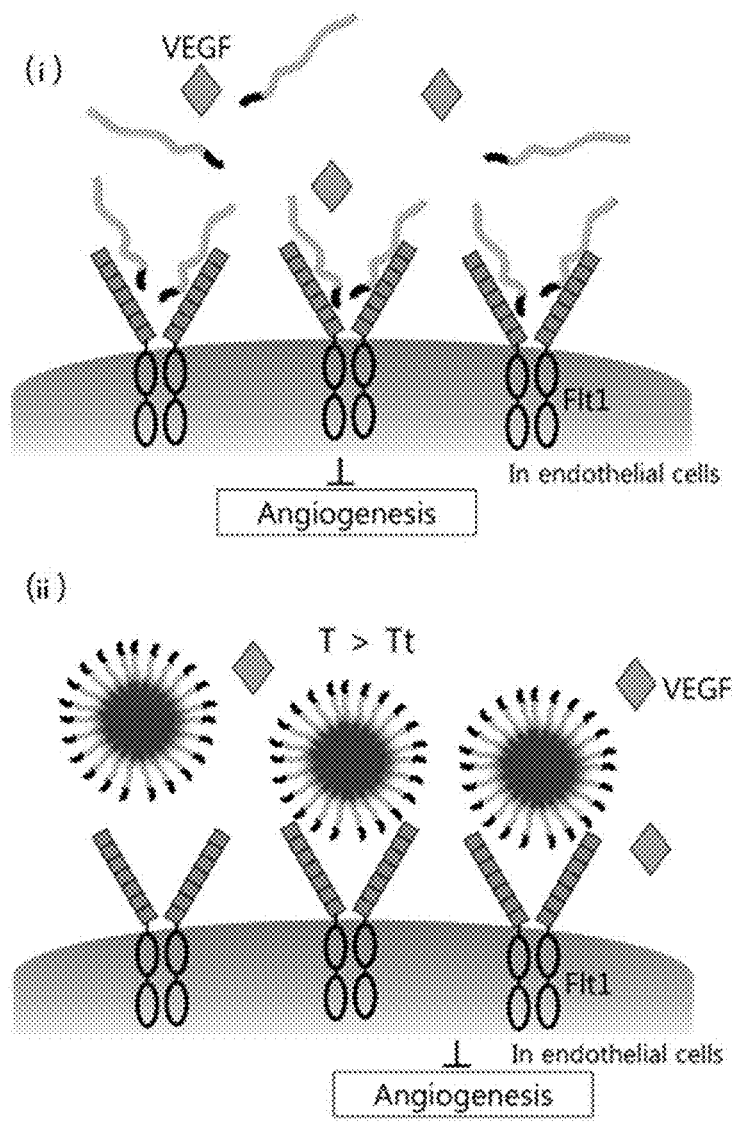

As shown in FIG. 5D (i), a fusion polypeptide corresponding to VEGFR-targeting peptide (anti-Flt1 peptide)-hydrophilic EBP may act as a therapeutic polypeptide due to strong non-covalent interactions between VEGFRs (in particular, VEGFR1) and the anti-Flt1 peptide. As shown in FIG. 5D (ii), a fusion polypeptide corresponding to VEGFR-targeting peptide (anti-Flt1 peptide)-hydrophilic EBP-hydrophobic EBP forms a micelle with a multivalent anti-Flt1 peptide, which increases the binding affinity of the fusion polypeptide for VEGFRs. Thus, use of the fusion polypeptide may enhance therapeutic efficacy for diseases associated with neovascularization. To minimize rapid degradation of anti-Flt1 peptides and to present anti-Flt1 peptides, as in vivo receptor antagonists, EBPs were introduced to an anti-Flt1 peptide as non-chromatographic purification polypeptide tags and as stabilizers.

Modified pET-21a (mpET-21a) plasmids harboring EBPP $[A_1G_4I_1]_n$, EBPP$[E_1G_4I_1]_n$ or EBPP$[G_1A_3F_2]_n$ (where the subscript number n of $[X_iY_jZ_k]_n$ is 6, 12, 18, 24, 30 or 36) were seamlessly cloned using standard molecular biology methodology. In particular, multimerization and fusion of EBPP genes were executed using recursive directional ligation (RDL) to construct genes encoding EBPPs with different molecular weights and EBPP block copolymers. FIG. 5A shows one method of gene cloning, by which genes for two different EBPPs and genes for an oligonucleotide cassette encoding an anti-Flt1 peptide were combined to prepare a gene for anti-Flt1-EBPP$[E_1G_4I_1]_{12}$-$[G_1A_3F_2]_{24}$. An mpET-21a plasmid harboring EBPP$[G_1A_3F_2]_{24}$ was double-digested with XbaI and BseRI and dephosphorylated to prepare a linearized vector, whereas an mpET-21a plasmid harboring EBPP$[E_1G_4I_1]_{12}$ was double-digested with XbaI and BseRI to prepare an insert. After ligation, a gene for a EBPP diblock of EBPP$[E_1G_4I_1]_{12}$-$[G_1A_3F_2]_{24}$ was prepared. The cloned gene was digested with BseRI, dephosphorylated, and fused with an oligonucleotide cassette encoding an anti-Fil1 peptide to prepare anti-Flt1-EBPP $[E_1G_4I_1]_{12}$-$[G_1A_3F_2]_{24}$. Similarly, a series of genes for anti-Flt1-EBPP$[A_1G_4I_1]_{3, 6, 12, 24}$ and anti-Flt1-EBPP$[E_1G_4I_1]_{12}$-$[G_1A_3F_2]_{12, 24}$ were cloned, and fusion polypeptides thereof were synthesized from plasmid-borne genes in E. coli, as shown in FIG. 1 (B).

In VEGFR-targeting peptide (anti-Flt1 peptide)-hydrophilic EBP-fusion polypeptide, anti-Flt1-EBPP$[A_1G_4I_1]_{3, 6, 12, 24}$ is soluble under physiological conditions and acts as a VEGFR antagonist to compete with VEGF, thereby inhibiting delivery of neovascularization signals to cells (FIG. 5D(i)). In an embodiment of the present invention, EBPP $[A_1G_4I_1]_n$ was selected because EBPP$[A_1G_4I_1]_n$ of all lengths is hydrophilic at body temperature without any charged amino acid residues, and because EBPP$[A_1G_4I_1]_n$ helps to provide an understanding of the correlation between EBPP length and binding affinity of an anti-Flt1 peptide according to EBPP blocks of four different lengths of anti-Flt1-EBPP$[A_1G_4I_1]_{3, 6, 12, 24}$. Furthermore, as shown in FIGS. 5c and 5d (ii), a fusion polypeptide[anti-Flt1-EBPP $[E_1G_4I_1]_{12}$-$[G_1A_3F_2]_{12, 24}$] of VEGFR-targeting peptide (anti-Flt1 peptide)-hydrophilic EBP-hydrophobic EBP may form a temperature-triggered core-shell micellar structure with a multivalent VEGFR1-targeting peptide because of amphiphilic properties of hydrophilic EBPP$[E_1G_4I_1]_{12}$ and hydrophobic EBPP$[G_1A_3F_2]_{12, 24}$ under physiological conditions. In addition, these properties enhance the binding affinity of the fusion peptides to VEGFRs and allow the fusion peptides to have high adhesion. In particular, hydrophobic EBPP$[G_1A_3F_2]_{12, 24}$ of two different lengths was used for micelle size control, and was used to study the effects of micelle size on the binding affinity of anti-Flt1-EBPP$[E_1G_4I_1]_{12}$-$[G_1A_3F_2]_{12, 24}$ to VEGFRs.

Example 7: Characterization of EBPs, Anti-Flt1-EBPP$[A_1G_4I_1]_{3n}$ and Anti-Flt1-EBP Diblock Block The purity of EBPs, anti-Flt1-EBPP$[A_1G_4I_1]_{3n}$ and anti-Flt1-EBP diblock blocks was determined by SDS-PAGE, and gel permeation chromatography (GPC) with a high-performance liquid chromatography (HPLC) 1260 series instrument (Agilent Technologies, Palo Alto, Calif., U.S.) using a Shodex GPC OHpak SB-804 HQ column (Showa Denko Co., Tokyo, Japan). Deionized water at 20° C. was used as an eluent at a flow rate of 1 ml/min and the GPC column was maintained at 20° C. Low dispersity pullulan in a range of 5,900 to 200,000 g/mol was used as a standard. A series of EBPs, anti-Flt1-EBPP$[A_1G_4I_1]_{3n}$ and anti-Flt1-EBP diblock blocks were analyzed using a refractive index detector (RID) and variable wavelength detector (VWD) at 280 nm. An effect of temperature on the inverse phase transition of various EBPs, anti-Flt1-EBPP$[A_1G_4I_1]_{3n}$ and anti-Flt1-EBP diblock blocks at 25 µM concentration in PBS was determined by measuring $OD_{350}$ using a Cary 100 Bio UV/Vis spectrophotometer equipped with a multi-cell thermoelectric temperature controller (Varian Instruments, Walnut Creek, Calif.) between 10 to 85° C. at a heating rate of 1° C./min Self-assembly behaviors of anti-Flt1-EBPP $[E_1G_4I_1]_{12}$-$[G_1A_3F_2]_{12}$ and anti-Flt1-EBPP $[E_1G_4I_1]_{12}$-$[G_1A_3F_2]_{24}$ from soluble unimers into micelles were characterized using a temperature-controlled Nano ZS90 (ZEN3690) dynamic light scattering (DLS) instrument (Malvern instruments, Worcestershire, UK), and the hydrodynamic radius ($R_H$) thereof at 25 µM in PBS was measured in 11 successive runs at each temperature in a temperature range from 18 to 50° C. at a heating rate of 1° C./min. In addition, $T_t$ thereof is defined as the onset temperature for phase transition, and calculated from each DLS plot.

Figure 6:
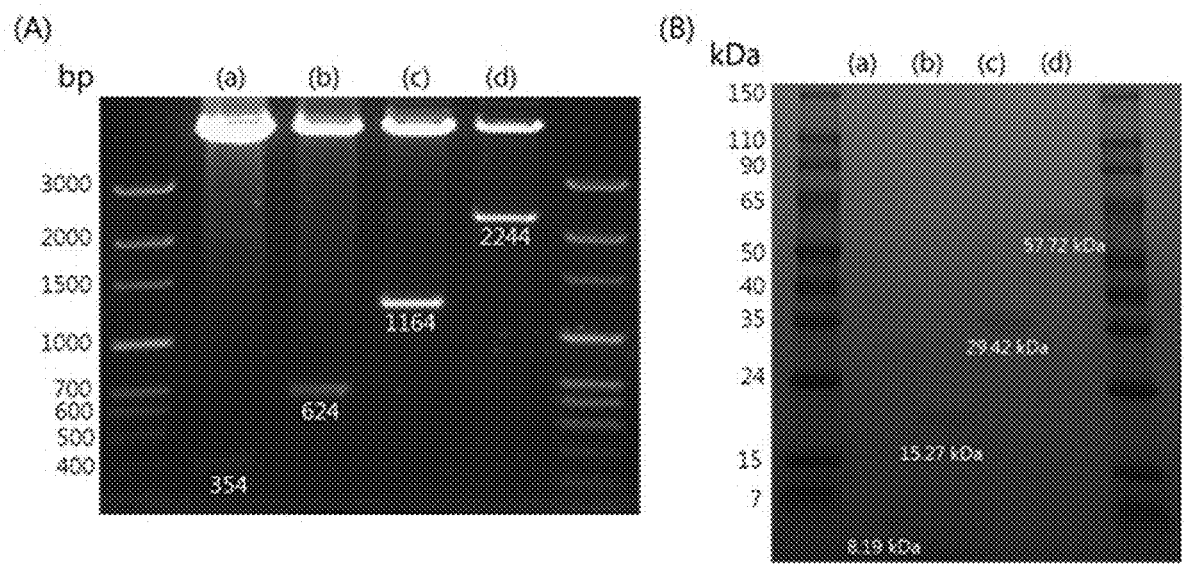
FIG. 6 shows (A) agarose gel (1%) images and (B) SDS-PAGE (4 to 20% gradient) gel images. (a) anti-Flt1-EBPP$[A_1G_4I_1]_3$, (b) anti-Flt1-EBPP$[A_1G_4I_1]_6$, (c) anti-Flt1-EBPP$[A_1G_4I_1]_{12}$ and (d) anti-Flt1-EBPP$[A_1G_4I_1]_{24}$.

Genes for fusion polypeptides composed of an anti-Flt1 peptide and hydrophilic EBP blocks with different lengths were constructed by molecular cloning and the lengths of those genes digested with XbaI and BseRI were confirmed by agarose gel electrophoresis as shown in FIG. 6(A). The DNA length of each gene encoding anti-Flt1-EBPP $[A_1G_4I_1]_3$, anti-Flt1-EBPP$[A_1G_4I_1]_6$, anti-Flt1-EBPP $[A_1G_4I_1]_{12}$ or anti-Flt1-EBPP$[A_1G_4I_1]_{24}$ (354, 624, 1164 or 2244 bp, from left to right) is indicated below the respective gene fragments. Since DNA sequences digested by XbaI and BseRI are located outside genes encoding the fusion polypeptides, the DNA lengths of the genes are 66 base pairs longer than original gene lengths shown in Table 4. The fusion polypeptides composed of an anti-Flt1 peptide and EBP blocks with different chain lengths were expressed in $E.$ $coli$ and purified by ITC, as previously reported for the temperature-responsive EBPs. A copper-stained SDS-PAGE gel (4 to 20% gradient) shown in FIG. 6(B) shows the following: Anti-Flt1-EBPP$[A_1G_4I_1]_n$ (subscript n is 3, 6, 12, or 24) was purified to have a homogeneity of at least 95% by an average of five rounds of ITC as characterized by HPLC. Compared to a standard protein migration distance, each fusion polypeptide shifted about 20% more than theoretical molecular weights shown in Table 4, which is in good agreement with previous studies. The expected molecular weights of the fusion polypeptides are indicated below each band (8.19, 15.27, 29.42 and 57.72 kDa, from left to right), and lanes at both ends of the SDS-PAGE gel represent standard protein size markers (7, 15, 24, 35, 40, 50, 65, 90, 110, and 150 kDa, from bottom to top).

Figure 7:
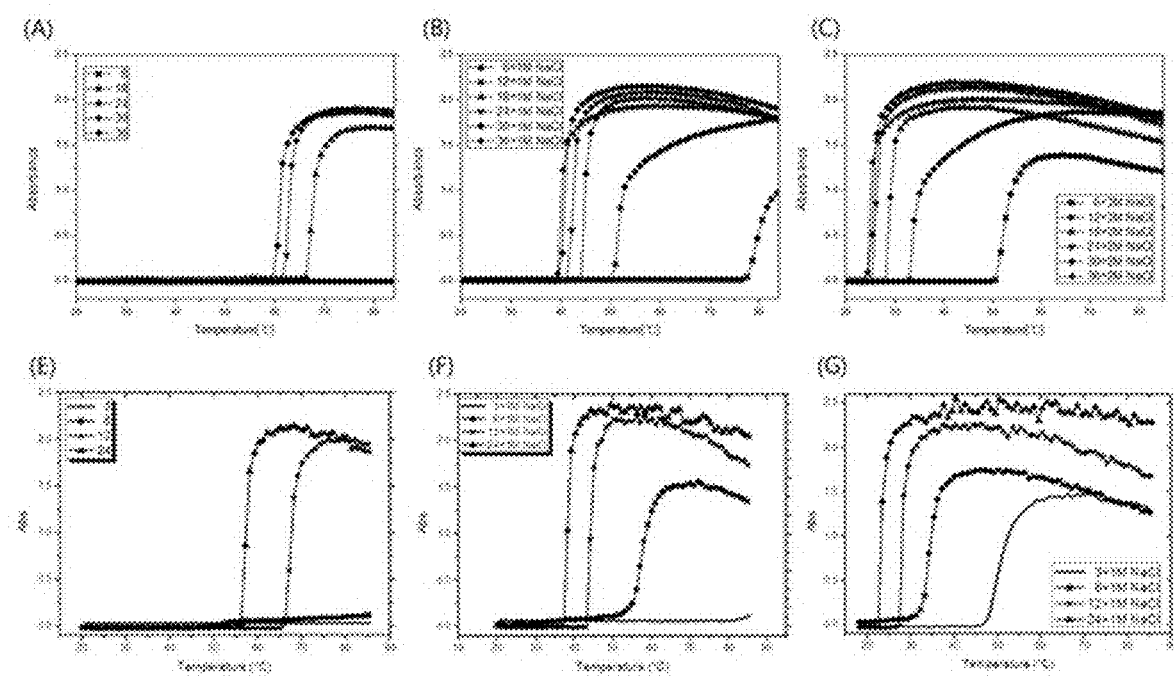
FIG. 7 shows the LCST of EBPP$[A_1G_4I_1]_{3n}$ (n: integer) and anti-Flt1-EBPP$[A_1G_4I_1]_{3n}$ (n: integer) as turbidity profiles. Turbidity profiles were determined by measuring the absorbance of (A to C) 25 µM EBPP$[A_1G_4I_1]_{3n}$ (n: integer) and (D to F) 25 µM anti-Flt1-EBPP$[A_1G_4I_1]_{3n}$ (n: integer). The absorbance was measured at 350 nm in 10 mM PBS (A and D), 10 mM PBS supplemented with 1 M sodium chloride (B and E), and 10 mM PBS supplemented with 2 M sodium chloride (C and F), while heating samples at a heating rate of 1° C./min.

FIG. 7 shows the thermal transition behaviors of EBP blocks and the thermal transition behaviors of fusion polypeptides composed of an anti-Flt1 peptide and EBP blocks with different chain lengths. Based on the thermal transition behaviors, the effect of EBP block length, sodium chloride concentration and anti-Flt1 peptide fusion on transition temperature ($T_t$) may be investigated. Turbidity profiles in FIG. 7 were obtained by measuring the absorbance of (A to C) 25 μM EBPP$[A_1G_4I_1]_{3n}$ (n: integer) and (D to F) 25 μM anti-Flt1-EBPP$[A_1G_4I]_{3n}$ (n: integer) in 10 mM PBS (A and D) and in 10 mM PBS supplemented with 1 M sodium chloride (B and E) or 2 M sodium chloride (C and F) at 350 nm while heating samples at a rate of 1° C./min. $T_t$ is defined as the inflection point of each thermal plot in FIG. 7 and summarized in Table 5.

TABLE 5

|  | (a) | (b) | (c) | (d) | (e) | (f) | (g) | (h) |
|---|---|---|---|---|---|---|---|---|
| 0M NaCl | N/A | N/A | N/A | 68 | N/A | N/A | 67 | 57 |
| 1M NaCl | N/A | 80 | 52 | 42 | N/A | 57 | 45 | 39 |
| 2M NaCl | N/A | 53 | 34 | 28 | 49 | 34 | 28 | 23 |

$T_t$ of (a) EBPP$[A_1G_4I_1]_3$, (b) EBPP$[A_1G_4I_1]_6$, (c) EBPP$[A_1G_4I_1]_{12}$, (d) EBPP$[A_1G_4I_1]_{24}$, (e) anti-Flt1-EBPP$[A_1G_4I_1]_3$, (f) anti-Flt1-EBPP$[A_1G_4I_1]_6$, (g) anti-Flt1-EBPP$[A_1G_4I_1]_{12}$ and (h) anti-Flt1-EBPP$[A_1G_4I_1]_{24}$ $T_t$ values in Table 5 are determined by measuring the inflection points of thermal profiles in FIG. 7. Transition temperature was changed depending on EBPP$[A_1G_4I_1]$ block length and sodium chloride concentration.

In general, EBPP$[A_1G_4I_1]_{3n}$ and anti-Flt1-EBPP $[A_1G_4I_1]_{3n}$ without polar amino acid residues exhibit $T_t$ higher than 37° C. under physiological conditions because Ala, Gly and Ile were introduced to the EBPPs as the guest residue of the repetitive pentapeptide unit of the EBPPs in a ratio of 1:4:1. Anti-Flt1-EBPP$[A_1G_4I_1]_{3n}$ was hydrophilic and VEGFR binding-fusion polypeptides thereof were soluble under physiological conditions, which allowed the polypeptides to specifically bind to VEGFRs without any steric hindrance. Thus, the fusion polypeptides of the present invention may act as VEGFR antagonists against VEGF. Furthermore, when the effect of EBPP block length and ionic strength on thermal responsiveness was analyzed, as the EBP block length of EBPP$[A_1G_4I_1]_{3n}$ and anti-Flt1-EBPP $[A_1G_4I_1]_{3n}$, and sodium chloride concentration in PBS increased, $T_t$ thereof decreased. In particular, the $T_t$ of anti-Flt1-EBPP$[A_1G_4I_1]_{3n}$ was much lower than that of EBPP$[A_1G_4I_1]_{3n}$ because Gly-Asn-Gln-Trp-Phe-Ile (GNQWFI) of an anti-Flt1 peptide sequence for targeting VEGFRs was hydrophobic, resulting in a decrease in the $T_t$ of anti-Flt1-EBPP$[A_1G_4I_1]_{3n}$. For example, the $T_t$ of anti-Flt1-EBPP$[A_1G_4I_1]_{12}$ and the $T_t$ of anti-Flt1-EBPP $[A_1G_4I_1]_{24}$ were about 18 and 11° C. lower than those of EBPP$[A_1G_4I_1]_{12}$ and EBPP$[A_1G_4I_1]_{24}$ in PBS, respectively. A $T_t$ difference (D$T_t$) between EBPP$[A_1G_4I_1]_3$ and anti-Flt1-EBPP$[A_1G_4I_1]_3$ was more than 36° C. in PBS with 2 M sodium chloride, whereas D$T_t$ between EBPP$[A_1G_4I_1]_3$ and anti-Flt1-EBPP$[A_1G_4I_1]_3$ was 23° C. in PBS with 1 M sodium chloride. Therefore, as EBPP$[A_1G_4I_1]$ block length became shorter, the $T_t$ of anti-Flt1-EBPP$[A_1G_4I_1]_{3n}$ was greatly decreased irrespective of various concentrations of sodium chloride. This data indicates that the effect of hydrophobicity of the anti-Flt1 peptide on the thermal transition of the EBPP$[A_1G_4I_1]$ block is potentially greater.

Figure 8:
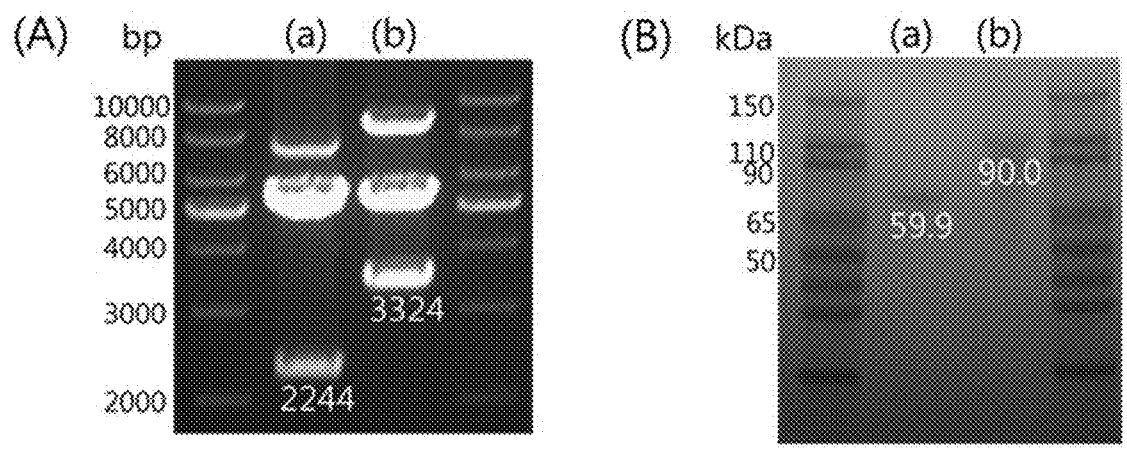
FIG. 8 shows the (A) agarose gel (1%) images and the (B) SDS-PAGE (4 to 20% gradient) gel images of fusion polypeptides. (A) A modified pET21-a (+) plasmid encoding anti-Flt1-EBPP[$E_1G_4I_1$]$_{12}$-[$G_1A_3F_2$]$_{12}$ or anti-Flt1-EBPP[$E_1G_4I_1$]$_{12}$-[$G_1A_3F_2$]$_{24}$ was digested by XbaI and BseRI. (B) The fusion polypeptides were expressed in E. coli and purified by ITC. 4 to 20% gradient gels were visualized with copper stain. An expected molecular weight was indicated below the band.

Next, the properties of fusion polypeptides composed of VEGFR-targeting peptide (anti-Flt1 peptide)-hydrophilic EBP-hydrophobic EBP are described. Two different genes, which encode a fusion polypeptide composed of "anti-Flt1 peptide" and "amphiphilic EBP diblock" of hydrophilic EBP-hydrophobic EBP having hydrophobic EBP blocks with various chain lengths, were constructed using RDL, a seamless molecular cloning method. The full lengths of those genes digested by XbaI and BseRI were confirmed by agarose gel electrophoresis as shown in FIG. 8(A). The DNA length of each gene encoding (a) anti-Flt1-EBPP $[E_1G_4I_1]_{12}$-$[G_1A_3F_2]_{12}$ or (b) anti-Flt1-EBPP$[E_1G_4I_1]_{12}$-$[G_1A_3F_2]_{24}$ (2244 and 3324 bp, from left to right) is indicated below each gene fragment. Since DNA sequences digested by XbaI and BseRI are located outside genes encoding the fusion polypeptides, the lengths of these genes are 66 base pairs longer than the original gene lengths of the fusion polypeptides the shown in Table 4. Two different anti-Flt1-EBP diblock copolypeptides including (a) anti-Flt1-EBPP$[E_1G_4I_1]_{12}$-$[G_1A_3F_2]_{12}$ and (b) anti-Flt1-EBPP $[E_1G_4I_1]_{12}$-$[G_1A_3F_2]_{24}$ were expressed in $E.$ $coli$ and purified by one among non-chromatographic purification methods, ITC as described above for purification of a series of temperature-responsive anti-Flt1-EBPP$[A_1G_4I_1]_{3n}$. The image of a copper-stained SDS-PAGE gel (4 to 20% gradient) in FIG. 8(B) shows the following: Both anti-Flt1-EBPP $[E_1G_4I_1]_{12}$-$[G_1A_3F_2]_{12}$ and anti-Flt1-EBPP$[E_1G_4I_1]_{12}$- $[G_1A_3F_2]_{24}$ were purified by an average of five rounds of ITC, each with one major polypeptide band. Compared to a standard protein migration distance, each fusion polypeptide shifted about 20% more than theoretical molecular weights shown in Table 4. In addition, as characterized by HPLC, after an average of five rounds of ITC runs, each polypeptide had a homogeneity of at least 95%. The expected molecular weights of the polypeptides are indicated below each band (59.9 and 90.0 kDa, from left to right), and lanes at both ends of the SDS-PAGE gel represent standard protein size markers (7, 15, 24, 35, 40, 50, 65, 90, 110, and 150 kDa, from bottom to top).

Figure 9:
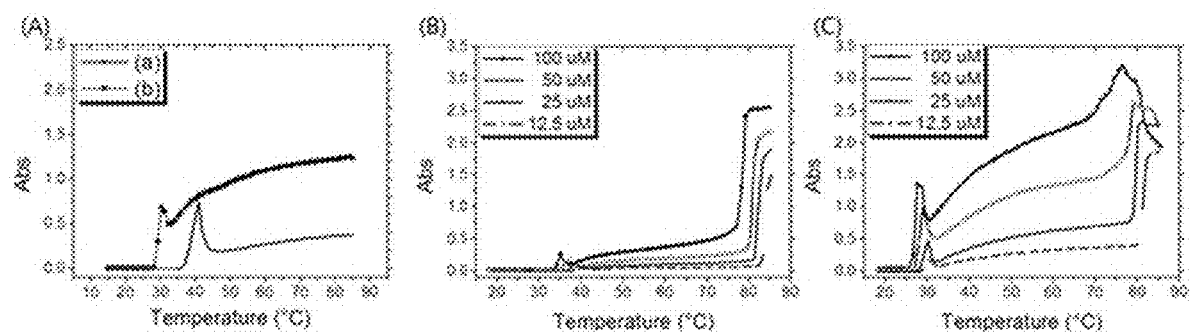
FIG. 9 shows the turbidity profiles of EBPP diblocks depending on the presence or absence of an anti-Flt1 peptide. (A) The turbidity profiles of (a) 25 μM EBPP [$E_1G_4I_1$]$_{12}$-EBPP[$G_1A_3F_2$]$_{12}$ and (b) 25 μM EBPP [$E_1G_4I_1$]$_{12}$-EBPP[$G_1A_3F_2$]$_{24}$. (B) The turbidity profiles of anti-Flt1-EBPP[$E_1G_4I_1$]$_{12}$-EBPP[$G_1A_3F_2$]$_{12}$ and (C) the turbidity profiles of anti-Flt1-EBPP[$E_1G_4I_1$]$_{12}$-EBPP [$G_1A_3F_2$]$_{24}$ were obtained for concentrations of 12.5, 25, 50 and 100 μM in 10 mM PBS. Absorbance was measured at 350 nm while heating the samples at a rate of 1° C./min. A phase transition occurred twice. The first phase transition occurred as a result of hydrophobic block aggregation, the second phase transition was affected by polar EBPP [$E_1G_4I_1$]$_{12}$. As EBPP diblock concentration increased, the first and second $T_t$ values thereof were lowered.
Figure 10:
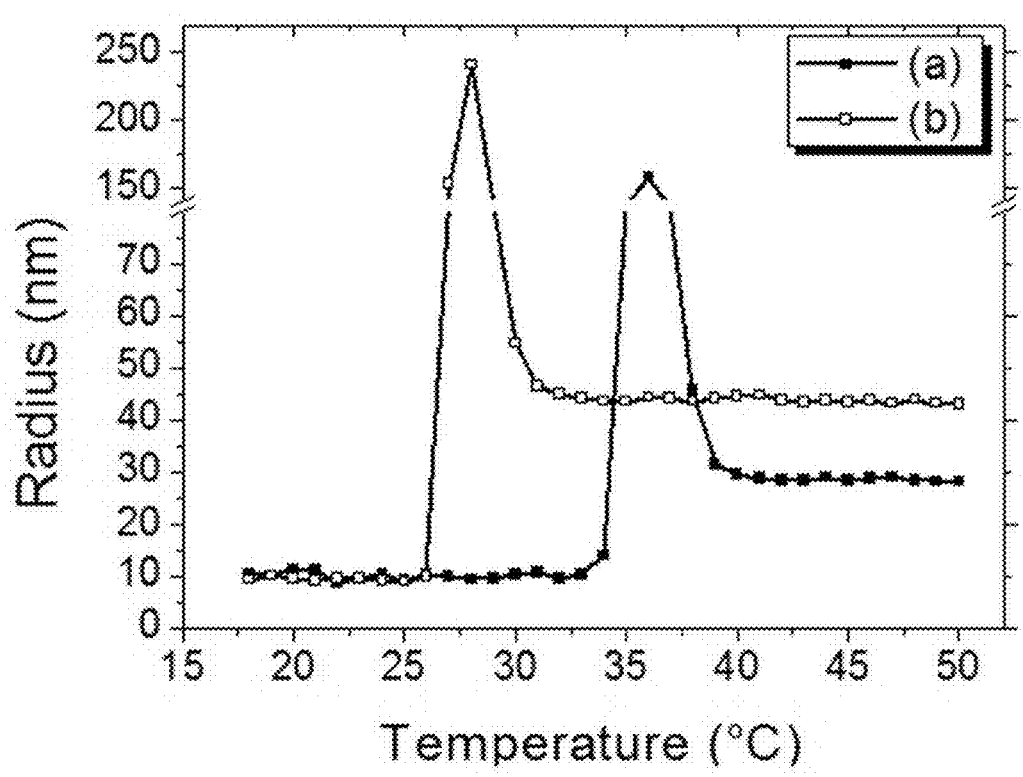
FIG. 10 shows the hydrodynamic radius of (a) anti-Flt1-EBPP[$E_1G_4I_1$]$_{12}$-EBPP[$G_1A_3F_2$]$_{12}$ and (b) anti-Flt1-EBPP [$E_1G_4I_1$]$_{12}$-EBPP[$G_1A_3F_2$]$_{24}$, and the hydrodynamic radius was measured by a DLS instrument. The hydrodynamic radius of EBPP diblock polypeptides was measured at 25 μM in 10 mM PBS. The hydrodynamic radius of EBPP diblock polypeptides prior to the first phase transition is less than 10 nm, indicating that the polypeptides are present in a soluble unimer form.

FIG. 9 shows the thermal transition behaviors of anti-Flt1-EBP diblock copolypeptides of anti-Flt1-EBPP $[E_1G_4I_1]_{12}$-$[G_1A_3F_2]_{12}$ and anti-Flt1-EBPP$[E_1G_4I_1]_{12}$- $[G_1A_3F_2]_{24}$ depending on the length and concentration of a hydrophobic EBPP[$G_1A_3F_2$] block. Turbidity profiles were obtained by measuring absorbance at 350 nm at four different concentrations (12.5, 25, 50 and 100 μM) in 10 mM PBS at a heating rate of 1° C./min. As described above, $T_t$ was measured as the inflection point of each thermal plot in FIG. 9 and summarized in Table 6 below.

created a unique metastable micelle phase right above the first $T_t$ thereof, which indicated that the thermally-triggered amphiphilic anti-Flt1-EBP diblock copolypeptides self-assembled into a metastable micelle. At this time, the metastable micelle continued to develop as a stable micelle in a temperature range from the first $T_t$ to the second $T_t$. This is

TABLE 6

|  | (a) | (b) | (c) | (d) | | | | | | |
|---|---|---|---|---|---|---|---|---|---|---|
| Conc. (uM) | 25 | 25 | 12.5 | 25 | 50 | 100 | 12.5 | 25 | 50 | 100 |
| First $T_t$ (° C.) | 39.02 | 29.12 | 34.2 | 36.2 | 37.4 | 39.5 | 26.7 | 28.0 | 29.1 | 29.2 |
| Second $T_t$ (° C.) | N/A | N/A | 78.2 | 81.2 | 82.3 | 84.4 | 74.6 | 78.0 | 79.2 | 81.2 |

$T_t$ of (a) EBPP[$E_1G_4I_1$]$_{12}$-EBPP[$G_1A_3F_2$]$_{12}$, (b) EBPP[$E_1G_4I_1$]$_{12}$-EBPP[$G_1A_3F_2$]$_{24}$, (c) anti-Flt1-EBPP[$E_1G_4I_1$]$_{12}$-EBPP[$G_1A_3F_2$]$_{12}$ and (d) anti-Flt1-EBPP[$E_1G_4I_1$]$_{12}$-EBPP[$G_1A_3F_2$]$_{24}$ $T_t$ values in Table 6 are determined by measuring the inflection points of thermal profiles in FIG. 7. The first phase transition occurred as a result of h block at the core of the micellar structure thereof. Furthermore, to determine the critical micelle concentrations (CMCs) of the anti-Flt1-EBP diblock copolypeptides, the micelle sizes thereof at various concentrations in a range of 0.1 to 25 µM were measured at 20° C. below $T_t$ and 37° C. above $T_t$. Under environmental conditions of 0.5 µM and 37° C., the anti-Flt1-EBPP[$E_1G_4I_1$]$_{12}$-[$G_1A_3F_2$]$_{12}$ still formed a metastable micelle with a $R_H$ of ~125 nm and the anti-Flt1-EBPP[$E_1G_4I_1$]$_{12}$-EBPP[$G_1A_3F_2$]$_{24}$ formed a stabilized micelle with a $R_H$ of ~44 nm. However, no micelle formation was observed for the two anti-Flt1-EBP diblock copolypeptides at 0.1 µM and 37° C., indicating that the 0.1 µM concentration was lower than CMCs thereof, and the CMCs were in a range of 0.1 to 0.5 µM. Therefore, the anti-Flt1-EBP diblock copolypeptides formed temperature-triggered core-corona micellar structures with multivalent anti-Flt1 peptides for targeting Flt1 under physiological conditions because of the amphiphilic properties of hydrophilic EBPP [$E_1G_4I_1$] and hydrophobic EBPP[$G_1A_3F_2$]. In particular, in the anti-Flt1-EBP diblock copolypeptides, different block lengths of hydrophobic EBPP[$G_1A_3F_2$] finely controlled micellar size, which affected the binding affinity thereof to Flt1, resulting in high adhesion.

Example 8: Determination of Specific Binding of Anti-Flt1-EBPP[$A_1G_4I_1$]$_{3n}$ and Anti-Flt1-EBP Diblock Block to Flt1

Specific binding of anti-Flt1-EBPP[$A_1G_4I_1$]$_{3n}$ (n: 1, 2, 4, and 8) and anti-Flt1-EBP diblock copolypeptides to Flt1 was determined by enzyme-linked immunosorbent assay (ELISA). First, to coat a 96 well plate with recombinant human VEGF165 protein (rhVEGF$_{165}$) (M.W. 38.4 kDa) present in a disulfide-linked homodimer, 50 µl of a solution containing the rhVEGF$_{165}$ at a concentration of 0.5 µg/ml was added to the 96 well plate, and the plated was incubated at 4° C. overnight. The wells of the 96 well plate coated with the rhVEGF$_{165}$ were washed with PBS containing 0.05% Tween-20 to completely remove unattached rhVEGF$_{165}$, and then the wells were incubated with PBS containing 3 wt % BSA at room temperature for 2 hours to block the surface of each well, which was not coated with the rhVEGF$_{165}$. After incubation, the wells were washed with PBS containing 0.05% Tween-20 to remove unbound BSA. Next, to impart specific binding affinity between an anti-Flt1 peptide and Flt1 (VEGFR1), a recombinant human Flt1-$F_c$ chimeric protein (M.W. 200.0 kDa) present in a disulfide-linked homodimer at a concentration of 0.5 µg/ml was pre-incubated with (1) anti-Flt1-EBPP[$A_1G_4I_1$]$_{3n}$ (n: 1, 2, 4, and 8) in PBS containing 1 wt % BSA or with (2) anti-Flt1-EBP diblock copolypeptides (anti-Flt1-EBPP[$E_1G_4I_1$]$_{12}$-EBPP [$G_1A_3F_2$] 12 and anti-Flt1-EBPP[$E_1G_4I_1$]$_{12}$-EBPP [$G_1A_3F_2$]$_{24}$) with hydrophobic blocks of different lengths. In this case, the pre-incubation was carried out at room temperature for 2 hours at different concentrations within a range of 0.5 to 500 µM. Thereafter, the mixed solution was added to rhVEGF$_{165}$-coated wells, followed by additional incubation at room temperature for 2 hours. The EBPP [$A_1G_4I_1$]$_{12}$ and EBP diblock copolypeptide (EBPP [$E_1G_4I_1$]$_{12}$-EBPP[$G_1A_3F_2$]$_{12}$ and anti-Flt1-EBPP [$E_1G_4I_1$]$_{12}$-EBPP[$G_1A_3F_2$]$_{24}$) with hydrophobic blocks (having the same concentration) of different lengths were used as a standard. Each well was washed with PBS supplemented with 0.05% Tween-20 to remove Flt1-$F_c$ protein that was not bound to rhVEGF$_{165}$ on the surface of the well. Whether human Flt1-$F_c$ protein was specifically bound to the rhVEGF$_{165}$-coated well was determined by measuring the absorbance of oxidized chromogenic substrates upon protein-antibody binding at 450 nm using rabbit anti-human IgG $F_c$-horseradish peroxidase (HRP) conjugates as a secondary antibody. PBS (containing 0.3 w % BSA) diluted with anti-human IgG $F_c$-HRP was added to each well and incubated for 1 hour at room temperature, followed by washing 8 times with PBS containing 0.05 Tween-20. 3,3', 5,5'-tetramethylbenzidine (TMB) was added to each well to indirectly determine the degree of specific binding of Flt1-$F_c$ protein to VEGF by measuring the specific interaction between the Flt1-$F_c$ protein and the anti-human IgG $F_c$-HRP protein, and HRP-catalyzed oxidation of the TMB. The color intensity of the oxidized TMB was measured at 450 nm. Each ELISA experiment was performed three times for reproducibility.

Figure 11:
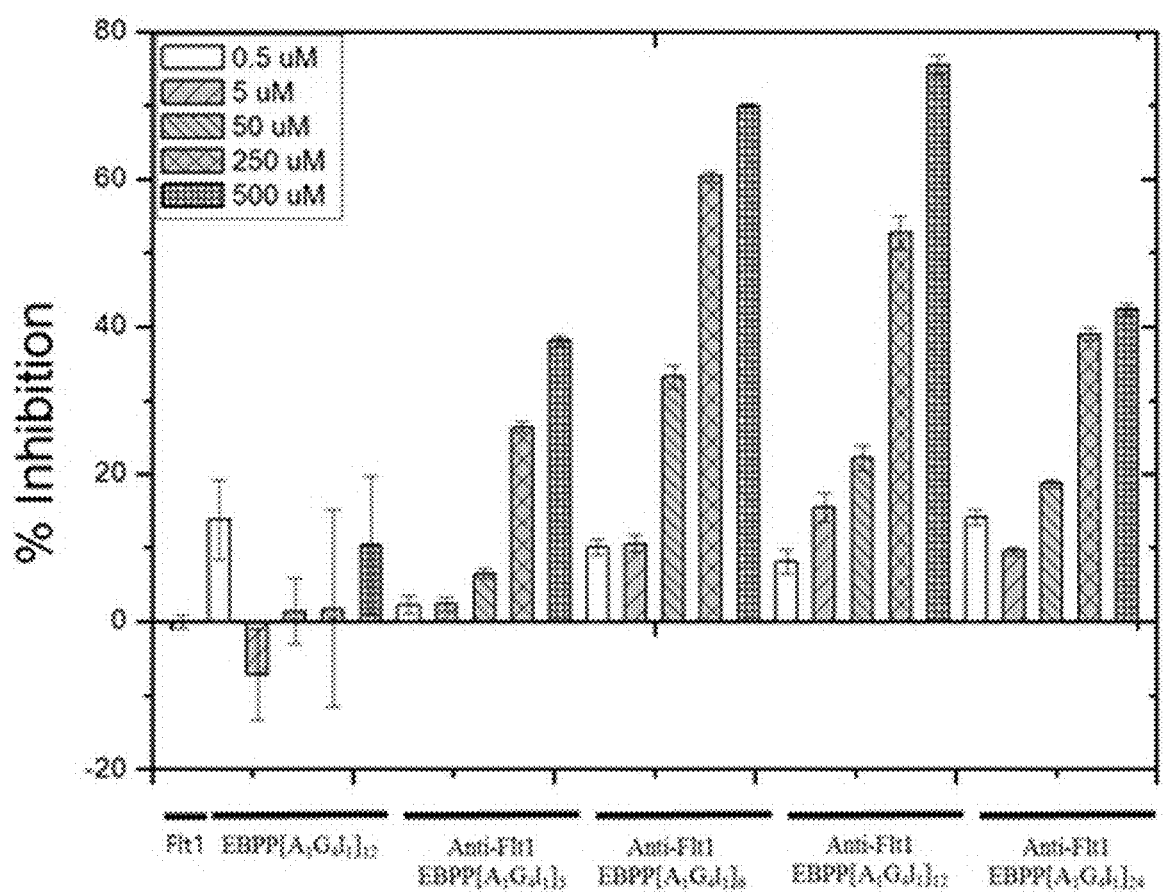
FIG. 11 shows the in vitro biological activities of EBPP [$A_1G_4I_1$]$_{12}$, anti-Flt1-EBPP[$A_1G_4I_1$]$_3$, anti-Flt1-EBPP [$A_1G_4I_1$]$_6$, anti-Flt1-EBPP[$A_1G_4I_1$]$_{12}$ and anti-Flt1-EBPP [$A_1G_4I_1$]$_{24}$, which inhibit VEGFR1 binding to coated VEGF.
Figure 12:
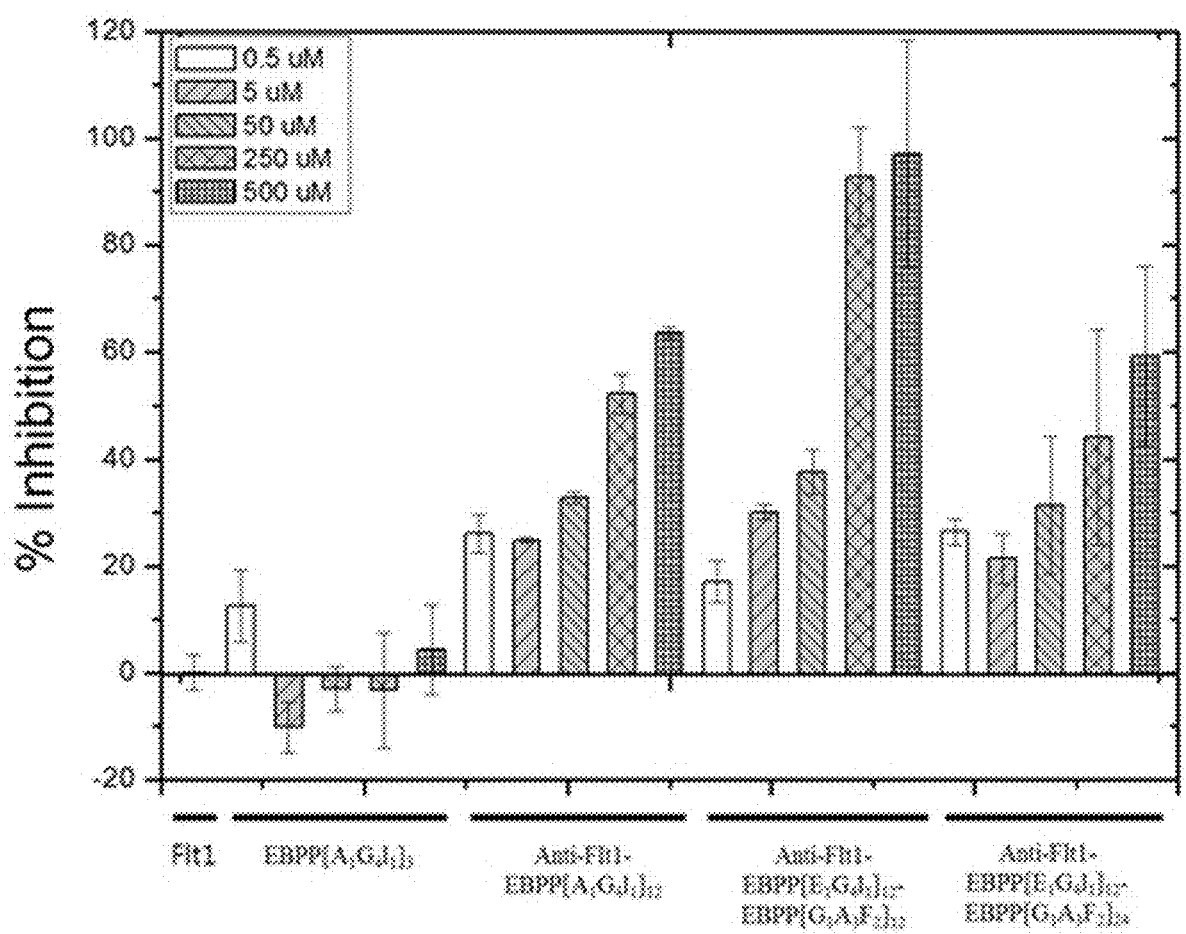
FIG. 12 shows the in vitro biological activities of EBPP [$A_1G_4I_1$]$_{12}$, anti-Flt1-EBPP[$A_1G_4I_1$]$_{12}$, anti-Flt1-EBPP [$E_1G_4I_1$]$_{12}$-EBPP[$G_1A_3F_2$]$_{12}$ and anti-Flt1-EBPP [$E_1G_4I_1$]$_{12}$-EBPP[$G_1A_3F_2$]$_{24}$, which inhibit VEGFR binding to coated VEGF. EBPP[$A_1G_4I_1$]$_{12}$ and anti-Flt1-EBPP [$A_1G_4I_1$]$_{12}$ were unimers at 37° C. On the other hand, anti-Flt1-EBPP[$E_1G_4I_1$]$_{12}$-EBPP[$G_1A_3F_2$]$_{12}$ formed metastable micelles at 37° C., and anti-Flt1-EBPP[$E_1G_4I_1$]$_{12}$-EBPP[$G_1A_3F_2$]$_{24}$ formed stable micelles.
Figure 13:
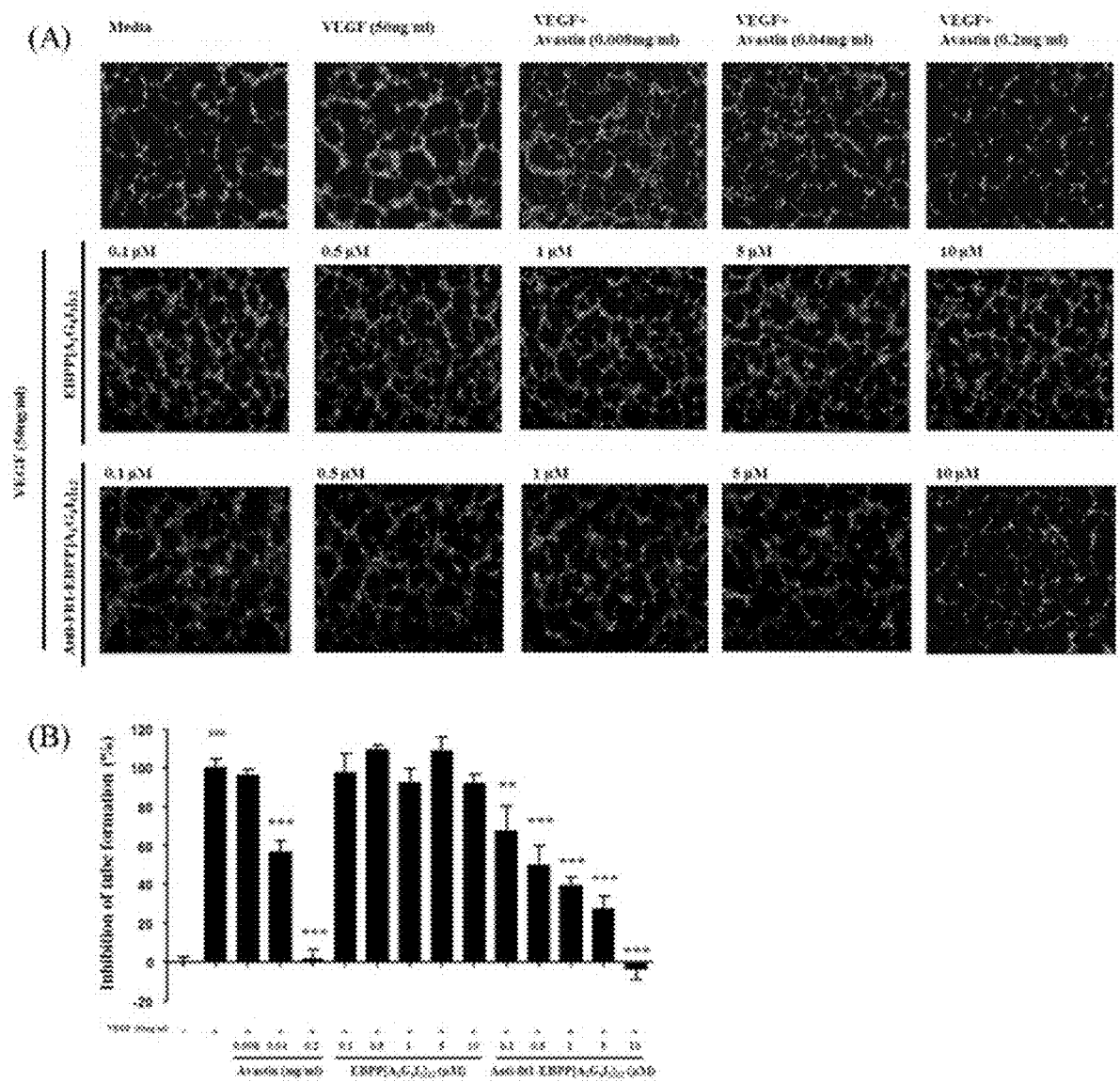
FIG. 13 shows the results of the in vitro tube formation assay of anti-Flt1-EBPP[$A_1G_4I_1$]$_{12}$. (A) the fluorescence microscope images of calcein-AM-labeled HUVECs and (B) the degree of inhibition of tube formation. The degree of inhibition of tube formation was quantified from the images of (A). The tube length of HUVECs treated with anti-Flt1-EBPP[$A_1G_4I_1$]$_{12}$ decreased with increasing the concentration of anti-Flt1-EBPP[$A_1G_4I_1$]. The anti-Flt1-EBPP [$A_1G_4I_1$]$_{12}$ inhibited migration and tube formation of HUVECs. Tubing lengths are average values±SE. *P≤0.05 by a t test.

The specific binding properties of a fusion polypeptide of VEGFR-targeting peptide (anti-Flt1 peptide)-hydrophilic EBP are examined. As shown in FIG. 11, the specific binding of anti-Flt1-EBPP[$A_1G_4I_1$]$_{3n}$ (n: integer) fusion polypeptides was characterized by enzyme-linked immunosorbent assay (ELISA). First, 38.4 kDa recombinant human VEGF$_{165}$ protein present in a disulfide-linked homodimer was coated on wells, and then the wells were blocked by bovine serum albumin (BSA). A 200.0 kDa recombinant human Flt1-$F_c$ chimeric protein present in a disulfide-linked homodimer was incubated with anti-Flt1-EBPP[$A_1G_4I_1$]$_{3n}$ (n: 1, 2, 4, and 8) at different concentrations within a range of 0.5 to 500 µM to induce specific binding between each other, and then the mixed solution was added to the VEGF-coated wells, followed by incubation for 2 hours at room temperature. Human Flt1-$F_c$ chimeric protein was specifically bound to the VEGF-coated wells was determined by measuring the absorbance of oxidized chromogenic substrates upon protein-antibody binding at 450 nm using rabbit anti-human IgG $F_c$-horseradish peroxidase (HRP) conjugates as a secondary antibody. Regardless of different concentrations, EBPP[$A_1G_4I_1$]$_{12}$ did not significantly inhibit specific binding between the Flt1-$F_c$ chimeric protein and VEGF. Contrary to the minimal inhibitory effect of EBPP [$A_1G_4I_1$]$_{12}$ with respect to the specific binding, anti-Flt1-EBPP[$A_1G_4I_1$]$_{3n}$ copolypeptides significantly inhibited an interaction between Flt1-$F_c$ and VEGF in a dose-dependent manner independent of EBPP[$A_1G_4I_1$] block length. These results indicate that anti-Flt1-EBPP[$A_1G_4I_1$]$_{3n}$ has a high specific binding capacity to a human Flt1-$F_c$ chimeric protein, which may prevent the human Flt1-$F_c$ chimeric protein from binding to VEGF. In particular, anti-Flt1-EBPP [$A_1G_4I_1$]$_{12}$ showed a maximum inhibitory effect of about 75% at 500 µM, whereas anti-Flt1-EBPP [$A_1G_4I_1$]$_{24}$ had a lower inhibitory effect than anti-Flt1-EBPP[$A_1G_4I_1$]$_{12}$, which might be the consequence of steric hindrance caused by an extended EBPP[$A_1G_4I_1$] chain length. Although hydrophilic EBPP[$A_1G_4I_1$]$_3$ blocks with different chain lengths were introduced to anti-Flt1 peptides as VEGFR1-specific antagonists, anti-Flt1-EBPP[$A_1G_4I_1$]$_{3n}$ copolypeptides retained high specificity of the anti-Flt1 peptide for Flt1, due to the inert nature of EBPs. In contrast to conventional peptide-polymer conjugates such as anti-Flt1 peptide-hyaluronate (HA) conjugates, the anti-Flt1-EBPP[$A_1G_4I_1$]$_{3n}$ copolypeptides were prepared at the gene level, and imparted the monodisperse molecular weight and enhanced stabilization of an anti-Flt1 peptide due to the inert nature of EBPs acting like PEG This monodisperse molecular weight and stability might increase the half-life of the anti-Flt1 peptide in vivo.

Next, the binding properties of fusion polypeptides of VEGFR-targeting peptide (anti-Flt1 peptide)-hydrophilic EBP-hydrophobic EBP are examined With specific binding of soluble anti-Flt1-EBPP[$A_1G_4I_1$]$_{3n}$ to a human Flt1-$F_c$ chimeric protein, anti-Flt1-EBP diblock blocks (anti-Flt1-EBPP [$E_1G_4I_1$]$_{12}$-EBPP[$G_1A_3F_2$]$_{12}$ and anti-Flt1-EBPP [$E_1G_4I_1$]$_{12}$-EBPP [$G_1A_3F_2$]$_{24}$) with hydrophobic blocks of different lengths formed temperature-triggered core-shell micellar structures with multivalent anti-Flt1 peptides under physiological conditions. Multivalent anti-Flt1 located on the outer shell of the formed self-assembled micelles increased the binding affinity of the fusion polypeptides to human Flt1 (VEGFR1). As measured by enzyme-linked immunosorbent assay (ELISA) in FIG. 12, as the concentrations of fusion polypeptides of anti-Flt1 peptide-hydrophilic EBP-hydrophobic EBP increased, specific binding between Flt1-$F_c$ and VEGF was significantly inhibited by the fusion polypeptides, which is in good agreement with the results of the example for soluble anti-Flt1-EBPP $[A_1G_4I_1]_{3n}$. Unlike the degree of inhibition of anti-Flt1-EBPP$[A_1G_4I_1]_{3n}$ fusion polypeptides with respect to specific binding between Flt1-$F_c$ and VEGF, anti-Flt1-EBPP $[E_1G_4I_1]_{12}$-EBPP$[G_1A_3F_2]_{12}$ micelles with a $R_H$ of ~125 nm in a metastable state showed a dramatically enhanced inhibitory effect (~95%) on specific binding between Flt1-$F_c$ and VEGF depending on the spatial multivalent display of Flt1-targeting peptides on the micelles. On the other hand, anti-Flt1-EBPP$[E_1G_4I_1]_{12}$-EBPP$[G_1A_3F_2]_{24}$ micelles with a $R_H$ of ~44 nm in a stable state exhibited a similar inhibition degree compared with the degree of inhibition of soluble anti-Flt1-EBPP$[A_1G_4I_1]_{3n}$ blocks. Although the two anti-Flt1-EBP diblock copolypeptides formed micelles in a concentration range from 0.5 to 500 μM at 37° C. under physiological conditions, the peptides showed a much different degree of inhibition with respect to specific binding between Flt1-$F_c$ and VEGF based on the stability of micelles thereof, potentially due to different binding affinities between the Flt1-$F_c$ and the controlled spatial display of the multivalent anti-Flt1 peptides of the micellar nanostructures. Importantly, anti-Flt1-EBPP$[E_1G_4I_1]_{12}$-EBPP$[G_1A_3F_2]_{12}$ micelles at 250 μM had a greater inhibitory effect than anti-Flt1-EBPP$[A_1G_4I_1]_3$ fusion polypeptides at 500 μM, which suggested that a lower dose of the anti-Flt1-EBPP $[E_1G_4I_1]_{12}$-EBPP$[G_1A_3F_2]_{12}$ might have a higher binding affinity to the human Flt1 protein in vivo for anti-neovascularization.

Example 9: In Vitro Tubing Assay of HUVECs Using Anti-Flt1-EBPP$[A_1G_4I_1]_{12}$ In vitro tubing assay of HUVECs using soluble anti-Flt1-EBPP$[A_1G_4I_1]_{12}$ was performed to evaluate effects of the soluble anti-Flt1-EBPP$[A_1G_4I_1]_{12}$ copolypeptides on proliferation, migration and tube formation of endothelial cells. For Matrigel coating, 200 μl of 8.7 mg/ml Matrigel was added to a 48 well plate and incubated at 37° C. for 1 hour to become solidified. To label HUVECs with fluorescence, HUVECs were incubated with 10 μM calcein-AM at 37° C. for 15 minutes and washed with PBS several times. The calcein-labeled HUVECs at $2\times10^4$ cells/well were grown on the Matrigel-coated wells, and incubated at 37° C. for 4 hours with 50 ng/ml recombinant human rhVEGF$_{165}$ and anti-Flt1-EBPP$[A_1G_4I_1]_{12}$ as a Flt1-specific antagonist at different concentrations. After incubation, it was determined whether proliferation, migration and tube formation of endothelial cells were stimulated. To clarify to what extent anti-Flt1-EBPP$[A_1G_4I_1]_{12}$ could inhibit tube formation of HUVECs, the same concentration of EBPP$[A_1G_4I_1]_{12}$ was assessed as a control. In addition, Avastin, a recombinant humanized monoclonal antibody (mAb) against VEGF, was used as another control to compare therapeutic efficacy for anti-neovascularization based on the therapeutic efficacy of anti-Flt1-EBPP$[A_1G_4I_1]_{12}$, as a Flt1-specific antagonist. The tube formation of HUVECs was photographed with Micromanipulator (Olympus, Tokyo, Japan), and quantified by measuring whole tube lengths in three random fields per well with Image lab software (Bio-Rad Laboratories, Hercules, Calif., USA). When the tubing assay was performed, the tube formation of HUVECs incubated in PBS for 4 hours was used as a control. The experiment was repeated three times.

As shown in FIG. 11, based on enzyme-linked immunosorbent assay (ELISA) results, it was confirmed that anti-Flt1-EBPP$[A_1G_4I_1]_{3n}$ (n: integer) fusion polypeptides had a high specific binding capacity to the human Flt1-$F_c$ chimeric protein, and 29.4 kDa anti-Flt1-EBPP$[A_1G_4I_1]_{12}$ showed a maximum degree of inhibition compared with soluble anti-Flt1-EBPP$[A_1G_4I_1]_{3n}$ fusion polypeptides with different EBP chain lengths. Accordingly, the effects of soluble anti-Flt1-EBPP$[A_1G_4I_1]_{12}$ fusion polypeptides on proliferation, migration and tube formation of endothelial cells were assessed in HUVECs in vitro. Calcein-labeled HUVECs at $2\times10^4$ cells/well were grown on a 48 well plate pre-coated with Matrigel, 50 ng/ml recombinant human rhVEGF$_{165}$ was treated to stimulate proliferation, migration and tube formation of endothelial cells, and anti-Flt1-EBPP $[A_1G_4I_1]_{12}$ acting as a Flt1 (VEGFR1)-specific antagonist was treated at different concentrations, followed by incubation. The same concentration of EBPP$[A_1G_4I_1]_{12}$ was used as a control to clearly show to what extent anti-Flt1-EBPP $[A_1G_4I_1]_{12}$ could inhibit the tube formation of HUVECs. In addition, Avastin (also named bevacizumab), a recombinant humanized monoclonal antibody (mAb) against VEGF, was used as a control to compare therapeutic efficacy for anti-neovascularization. Avastin has been widely used to treat various neovascular eye diseases, such as age-related macular degeneration (AMD) and diabetic retinopathy, based on specific binding between Avastin and VEGF. Based on specific binding of anti-Flt1-EBPP$[A_1G_4I_1]_3$ to the human Flt1 protein in the membrane of HUVECs, it was assumed that the inhibitory effects of anti-Flt1-EBPP$[A_1G_4I_1]_{3n}$ and Avastin on the tube formation of HUVECs were caused by specific protein-protein interactions, while Avastin bound to rhVEGF$_{165}$ and minimized rhVEGF$_{165}$-triggered cellular signaling for the tube formation and neovascularization of HUVECs. As characterized by in vitro tubing assay of anti-Flt1-EBPP$[A_1G_4I_1]_{12}$, fluorescence images of calcein-AM labeled HUVECs and the degree of inhibition of tube formation based on the normalized tube length of HUVECs in the images were shown in FIG. 13. The tube length of HUVECs was measured by tracking the fluorescence signal of HUVECs, averaged under each condition, and the tube length of HUVECs incubated in PBS for 4 hours was used as a baseline. A tube length when HUVECs were treated with rhVEGF$_{165}$ for 4 hours was set at 100%, and tube length at each concentration was normalized. The tube length of HUVECs incubated with EBPP$[A_1G_4I_1]_{12}$ as a control was similar to that of HUVECs treated with rhVEGF$_{165}$, indicating that EBPP$[A_1G_4I_1]_{12}$ had no significant effect on the tube formation of HUVECs. On the other hand, in the case of anti-Flt1-EBPP$[A_1G_4I_1]_{12}$ as a Flt1-specific antagonist, as the concentration of the anti-Flt1-EBPP$[A_1G_4I_1]_{12}$ increased in a range of 0.1 to 10 μM, the tube length of HUVECs gradually decreased. In accordance with decrease of the tube length of HUVECs when incubated with anti-Flt1-EBPP$[A_1G_4I_1]_{12}$, fluorescence images clearly show that the degree of inhibition of migration and tube formation of HUVECs became evident as the concentration of anti-Flt1-EBPP[$A_1G_4I_1$]$_{12}$ increased. These results indicate that anti-Flt-EBPP[$A_1G_4I_1$]$_{12}$ inhibits the tube formation of HUVECs and the degree of inhibition is greatly controlled by the concentration of anti-Flt1-EBPP [$A_1G_4I_1$]$_{12}$. In particular, HUVECs incubated with 10 μM anti-Flt1-EBPP[$A_1G_4I_1$]$_{12}$ showed no significant migration and tube formation even in the presence of rhVEGF$_{165}$, which was similar to use of Avastin at 0.2 mg/ml. Therefore, as validated by ELISA, the anti-Flt1-EBPP[$A_1G_4I_1$]$_{12}$ fusion polypeptides still retained high specificity of an anti-Flt1 peptide against Flt1.

Example 10: In Vivo Anti-Neovascularization Using Anti-Flt1-EBPP[$A_1G_4I_1$]$_{12}$ in Laser-Induced Choroidal Neovascularization Model 6- to 8-week-old female C57BL-6 mice were anesthetized with intraperitoneal injection of ketamine at 100 mg/kg and xylazine at 10 mg/kg, and the pupils were dilated with 5 mg/ml tropicamide, and 532 nm laser diode (150 to 210 mW, 0.1 sec, 50 to 100 μM) was applied to each fundus to induce choroidal neovascularization in vivo. Multiple burns were performed in the 6, 9, 12, and 3 o'clock positions of the posterior pole of the eye with a slit-lamp delivery system. Production of bubbles at the time of laser, which indicates Bruch's membrane rupturing, is an important factor in obtaining the CNV model. To evaluate an effect of anti-Flt1-EBPP[$A_1G_4I_1$]$_{3n}$ copolypeptides on anti-neovascularization in a laser-induced choroidal neovascularization model in vivo, the CNV model mice were injected in an intravitreal manner with PBS as a vehicle, EBPP[$A_1G_4I_1$]$_{12}$ or various concentrations of anti-Flt1-EBPP[$A_1G_4I_1$]$_{12}$ once a day for 5 days and anesthetized after 14 days with an intraperitoneal injection of ketamine at 100 mg/kg and xylazine at 10 mg/kg. The mice were treated with retro-orbital injection of 100 μl ultrapure water containing 25 mg/ml FITC-dextran. Enucleated eyes were then fixed in 10% formalin for 30 minutes at room temperature. The cornea, iris, lens, and vitreous humor were gently removed under a stereomicroscope (Leica, Wetzlar, Germany). Four radial incisions were made in the dissected retina, which was then flattened with a coverslip. Each in vivo anti-neovascularization experiment was performed with three replicates.

Figure 14:
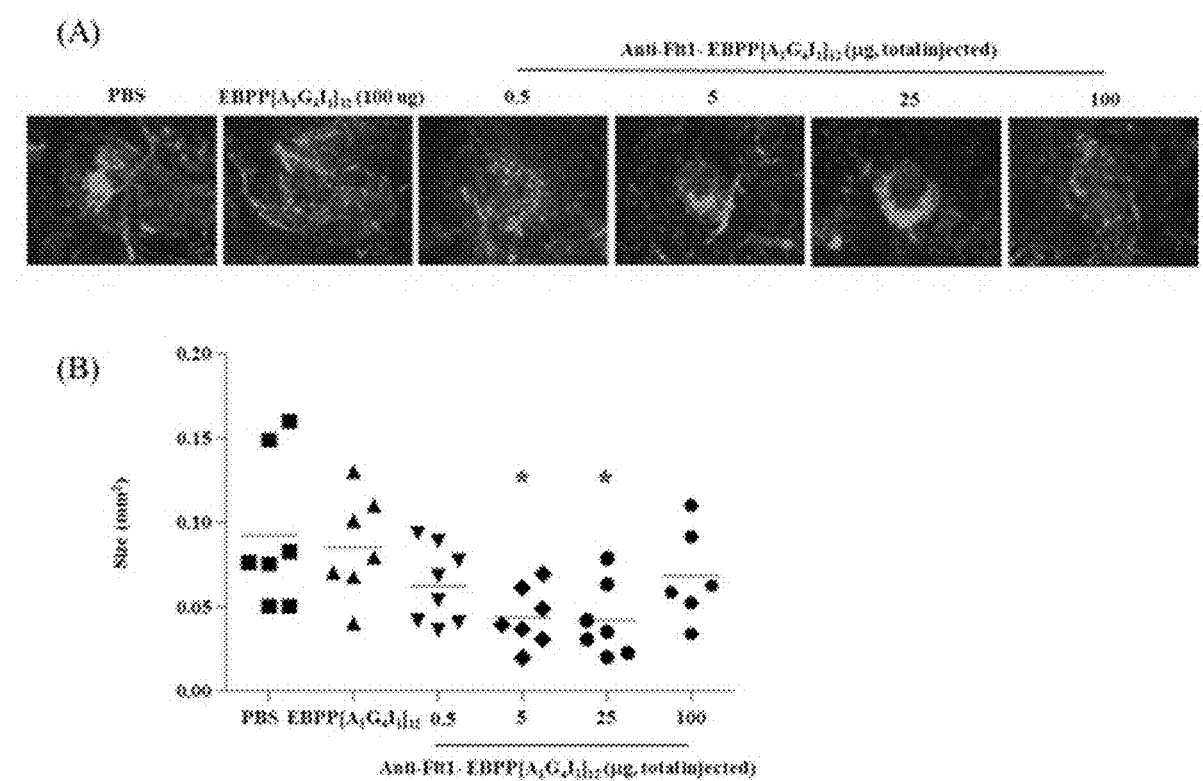
FIG. 14 shows an in vivo inhibition effect of anti-Flt1-EBPP[$A_1G_4I_1$]$_{12}$ in a laser-induced choroidal neovascularization model. C57BL6 mice (n=3 per group) were treated with a vehicle (PBS), EBPP[$A_1G_4I_1$]$_{12}$ (20 μg) or anti-Flt1-EBPP[$A_1G_4I_1$]$_{12}$ (0.1, 1, 5 and 20 μg) after laser-induced injury, and the treatment was continued for 5 days. At day 14 after laser injury, mice were euthanized and fluorescein isothiocyanate (FITC)-dextran perfused whole choroidal flat-mounts were prepared. The CNV lesion size was quantified by Nano-Zoomer and FISH. (A) representative flat mount fluorescence microscopic images. (B) a graph of the CNV size of each treated group. Each point corresponds to a CNV lesion, and a horizontal bar corresponds to the average value of each group. *P≤0.05 by an unpaired t test. The data represents two independent experiments.

By ELISA and HUVEC tubing assay, it was demonstrated that anti-Flt1-EBPP[A $G_4I_1$]$_{3n}$ fusion polypeptides retained anti-neovascularization activity as an antagonist against VEGFR1. The present inventors hypothesized that anti-Flt1-EBPP[$A_1G_4I_1$]$_{3n}$ fusion polypeptides might show a therapeutic activity with respect to neovascularization-related eye diseases (in particular, retinal neovascular disease, age-related macular degeneration (AMD)). Intravitreal injection of anti-Flt1-EBPP[$A_1G_4I_1$]$_{12}$ was evaluated for the suppression of laser-induced choroidal neovascularization (CNV), which was an animal model for AMD, in C57BL-6 mice. Daily injection of protein solutions started immediately after laser injury and maintained for 5 days. Injection of a vehicle (PBS) or EBPP[$A_1G_4I_1$]$_{12}$ was used as a negative control. CNV lesion volumes were imagined and evaluated with fluorescein isothiocyanate (FITC)-dextran perfused whole choroidal flat-mounts at day 14 after laser injury (FIG. 14A). Quantitative analysis showed that doses of 0.1, 1, 5 and 20 μg of anti-Flt1-EBPP[$A_1G_4I_1$]$_{12}$ per day for 5 days (in total 0.5, 5, 25 and 100 μg) suppressed CNV lesion size by 32%, 52.3% (P<0.05), 54.4% (P<0.05), and 25.9%, respectively, as compared with PBS control mice (FIG. 14B). The CNV lesion sizes of an EBPP[$A_1G_4I_1$]$_{12}$-treated animal had values similar to those of a PBS-treated animal. The suppressive effect of EBPP[$A_1G_4I_1$]$_{12}$ on a CNV lesion showed a dose dependent manner in a range from 0.5 to 25 μg in total. However, 100 μg anti-Flt1-EBPP[$A_1G_4I_1$]$_{12}$ showed a reduced effect on suppression of the CNV lesion, potentially due to an excessive dose of anti-Flt1-EBPP[$A_1G_4I_1$]$_{12}$.

Binding affinity of a targeting ligand against a growth factor receptor (GFR) in cells is important for various diseases associated with cell growth such as neovascularization, because the binding affinity determines whether intracellular signaling will proceed. In the present invention, VEGFR-targeting fusion polypeptides, which are composed of thermally responsive elastin-based polypeptides (EBPs) and vascular endothelial growth factor receptor (VEGFR)-targeting peptides, were genetically manipulated, expressed, and purified and the physicochemical properties thereof were analyzed. The EBPs were introduced as non-chromatographic purification tags and also introduced as a stabilizer, like a poly(ethylene glycol) conjugate, for minimizing rapid in vivo degradation of VEGFR-targeting peptides. In addition, the VEGFR-targeting peptide was introduced to function as a receptor antagonist by specifically binding to VEGFRs.

A fusion polypeptide composed of VEGFR-targeting peptide (anti-Flt1 peptide)-hydrophilic EBP exhibited a soluble unimer form. On the other hand, a fusion polypeptide composed of VEGFR-targeting peptide (anti-Flt1 peptide)-hydrophilic EBP-hydrophobic EBP exhibited a temperature-triggered core-shell micellar structure with a multivalent VGFR-targeting peptide under physiological conditions. As analyzed by enzyme-linked immunosorbent assay (ELISA), this structure greatly increased the binding affinity of the fusion polypeptide for VEGF receptors. Depending on the spatial display of a VEGFR-targeting peptide, the binding affinity of the fusion polypeptides to VEGFRs was greatly regulated.

An anti-Flt1-EBPP[$A_1G_4I_1$]$_{3n}$ fusion polypeptide (anti-Flt1 peptide-hydrophilic EBP), which existed as a soluble unimer form below a transition temperature, showed a high anti-neovascularization effect in a CNV model as compared with a EBPP block as a control. In addition, an anti-Flt1-EBP diblock fusion polypeptide (anti-Flt1 peptide-hydrophilic EBP-hydrophobic EBP) formed a temperature-triggered, self-assembled multivalent micellar nanostructure under physiological conditions, resulting in a great difference in the degree of inhibition with respect to specific binding between Flt1-$F_c$ and VEGF depending on the stability of the micellar nanostructure thereof. In the tube formation assay of HUVECs in vitro, anti-Flt1-EBPP [$A_1G_4I_1$]$_{12}$ greatly reduced tube formation, whereas EBPP [$A_1G_4I_1$]$_{12}$ had no significant effect on tube formation, which was due to specific interactions between the anti-Flt1-EBPP[$A_1G_4I_1$]$_{12}$ and Flt1 (VEGFR1) on the HUVEC membrane. Finally, in the laser-induced CNV model of mice, anti-Flt1-EBPP[$A_1G_4I_1$]$_{12}$ showed a high anti-neovascularization effect. Therefore, this fusion polypeptide and the self-assembled multivalent micellar nanostructure thereof with an anti-Flt1 may be used as a therapeutic polypeptide targeting neovascularization, such as treatment of retinal, corneal, choroidal neovascularization, tumor growth, cancer metastasis, diabetic retinopathy, and asthma.

A fusion polypeptide for inhibiting neovascularization of the present invention can provide a new direction for a drug delivery system for anti-neovascularization, such as treatment of retinal, corneal, choroidal neovascularization, tumor growth, cancer metastasis, diabetic retinopathy, and asthma.

What is claimed is:

1. A fusion polypeptide for inhibiting neovascularization, comprising:
   a peptide of SEQ ID NO: 38 specifically binding to vascular endothelial growth factor (VEGF) receptors; and
   a hydrophilic elastin-based polypeptide (hydrophilic EBP) linked to the peptide,
   wherein the fusion polypeptide further comprises a hydrophobic elastin-based polypeptide (hydrophobic EBP) linked to the hydrophilic EBP, and
   the hydrophobic EBP is consisting of an amino acid sequence represented by Formula 1 or 2 below:

Formula 1
   [SEQ ID NO: 1]
   n; or

Formula 2
   [SEQ ID NO: 2]
   n, wherein

SEQ ID NO: 1 is consisting of
   [VPGXG VPGXG VPGXG VPGXG VPGXG VPGXG];

SEQ ID NO: 2 is consisting of
   [VPAXG VPAXG VPAXG VPAXG VPAXG VPAXG];

n is an integer of 1 or more, and represents the number of repeats of SEQ ID NO: 1 or SEQ ID NO: 2; and
   X is an amino acid other than proline, is selected from any natural or artificial amino acids when the pentapeptide VPGXG or VPAXG is repeated, and at least one of X is a hydrophobic or aliphatic amino acid.

2. The fusion polypeptide according to claim 1, wherein the hydrophobic EBP is consisting of an amino acid sequence represented by Formula 1 or 2:
   in Formula 1, n is 1, and each X of the pentapeptide repeats is consisting of G (Gly), A (Ala), and F (Phe) in a ratio of 1:3:2 [SEQ ID NO: 28],
   or
   in Formula 2, n is 1, and each X of the pentapeptide repeats is consisting of,
   G (Gly), A (Ala), and F (Phe) in a ratio of 1:3:2 [SEQ ID NO: 29];
   K (Lys), A (Ala), and F (Phe) in a ratio of 1:3:2 [SEQ ID NO: 30];
   D (Asp), A (Ala), and F (Phe) in a ratio of 1:3:2 [SEQ ID NO: 31];
   K (Lys) and F (Phe) in a ratio of 3:3 [SEQ ID NO: 32];
   D (Asp) and F (Phe) in a ratio of 3:3 [SEQ ID NO: 33];
   H (His), A (Ala), and I (Ile) in a ratio of 3:2:1 [SEQ ID NO: 34];
   H (His) and G (Gly) in a ratio of 5:1 [SEQ ID NO. 35]; or
   G (Gly), C (Cys), and F (Phe) in a ratio of 1:3:2 [SEQ ID NO: 36].

3. The fusion polypeptide according to claim 1, wherein the hydrophobic EBP is consisting of an amino acid sequence represented by Formula 2:
   in Formula 2, n is 12, and each X of the pentapeptide repeats is consisting of G (Gly), A (Ala), and F (Phe) in a ratio of 1:3:2 [SEQ ID NO: 46], or
   in Formula 2, n is 24, and each X of the pentapeptide repeats is consisting of
   G (Gly), A (Ala), and F (Phe) in a ratio of 1:3:2 [SEQ ID NO: 47].

4. The fusion polypeptide according to claim 1, wherein the fusion polypeptide is consisting of an amino acid sequence corresponding to SEQ ID NO: 52 or SEQ ID NO: 53.

5. The fusion polypeptide according to claim 1, wherein the fusion polypeptide forms a self-assembled nanostructure having a core-shell structure, when the hydrophobic EBP forms a core structure and the hydrophilic EBP and the VEGF receptor-specific peptide form a shell structure by a temperature stimulus ranging from 18 to 50° C.

6. The fusion polypeptide according to claim 5, wherein the self-assembled nanostructure comprises a multivalent VEGF receptor-specific peptide as a shell.

7. A composition for treating diseases caused by neovascularization, comprising the fusion polypeptide of claim 1, wherein
   the fusion polypeptide forms a self-assembled nanostructure having a core-shell structure, when a hydrophobic EBP forms a core structure and a hydrophilic EBP and a VEGF receptor-specific peptide form a shell structure by a temperature stimulus ranging from 18 to 50° C., and
   the self-assembled nanostructure comprises a multivalent VEGF receptor-specific peptide as a shell, whereby binding affinity between the self-assembled nanostructure and a VEGF receptor increases, and VEGF fails to bind to the VEGF receptor, thereby inhibiting neovascularization.

8. The composition according to claim 7, wherein the diseases caused by neovascularization is any one or more selected from the group comprising diabetic retinopathy, retinopathy of prematurity, macular degeneration, choroidal neovascularization, neovascular glaucoma, eye diseases caused by corneal neovascularization, corneal transplant rejection, corneal edema, corneal opacity, cancer, hemangioma, hemangiofibroma, rheumatoid arthritis, and psoriasis.

\* \* \* \* \*

SEQUENCE LISTING

<160> NUMBER OF SEQ ID NOS: 53

<210> SEQ ID NO 1
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 1

Val Pro Gly Xaa Gly Val Pro Gly Xaa Gly Val Pro Gly Xaa Gly Val
1               5                   10                  15

Pro Gly Xaa Gly Val Pro Gly Xaa Gly Val Pro Gly Xaa Gly
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Elastin-based peptide, Xaa can be any amino
      acid, natural or non-natural
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 2

Val Pro Ala Xaa Gly Val Pro Ala Xaa Gly Val Pro Ala Xaa Gly Val

```
1               5                   10                  15
Pro Ala Xaa Gly Val Pro Ala Xaa Gly Val Pro Ala Xaa Gly
            20                  25                  30
```

<210> SEQ ID NO 3
<211> LENGTH: 90
<212> TYPE: DNA
<213> ORGANISM: Artificial Sequence
<220> FEATURE:
<223> OTHER INFORMATION: EBP

<400> SEQUENCE: 3
gtcccaggtg gaggtgtacc cggcgcgggt gtcccaggtg gaggtgtacc tgggggtggg    60
gtccctggta ttggcgtacc tggaggcggc                                    90

<210> SEQ ID NO 4
<211> LENGTH: 90
<212> TYPE: DNA
<213> ORGANISM: Artificial Sequence
<220> FEATURE:
<223> OTHER INFORMATION: EBP

<400> SEQUENCE: 4
gttccagctg gcggtgtacc tgctgctgct gttccggccg gtggtgttcc ggcgggcggc    60
gtgcctgcaa taggagttcc cgctggtggc                                    90

<210> SEQ ID NO 5
<211> LENGTH: 90
<212> TYPE: DNA
<213> ORGANISM: Artificial Sequence
<220> FEATURE:
<223> OTHER INFORMATION: EBP

<400> SEQUENCE: 5
gttccgggtg gtggtgttcc gggtaaaggt gttccgggtg gtggtgttcc gggtggtggt    60
ggtgttccgg gtatcggtgt tccgggtggc                                    90

<210> SEQ ID NO 6
<211> LENGTH: 90
<212> TYPE: DNA
<213> ORGANISM: Artificial Sequence
<220> FEATURE:
<223> OTHER INFORMATION: EBP

<400> SEQUENCE: 6
gttccggcgg gtggtgttcc ggcgaaaggt gttccggcgg gtggtgttcc ggcgggtggt    60
gttccggcga tcggtgttcc ggcgggtggc                                    90

<210> SEQ ID NO 7
<211> LENGTH: 90
<212> TYPE: DNA
<213> ORGANISM: Artificial Sequence
<220> FEATURE:
<223> OTHER INFORMATION: EBP

<400> SEQUENCE: 7
gttccgggtg gtggtgttcc gggtgatggt gttccgggtg gtggtgttcc gggtggtggt    60
ggtgttccgg gtatcggtgt tccgggtggc                                    90

<210> SEQ ID NO 8
<211> LENGTH: 90
<212> TYPE: DNA

<213> ORGANISM: Artificial Sequence
<220> FEATURE:
<223> OTHER INFORMATION: EBP

<400> SEQUENCE: 8

```
gttccggcgg gtggtgttcc ggcggatggt gttccggcgg gtggtgttcc ggcgggtggt        60
gttccggcga tcggtgttcc ggcgggtggc                                         90
```

<210> SEQ ID NO 9
<211> LENGTH: 90
<212> TYPE: DNA
<213> ORGANISM: Artificial Sequence
<220> FEATURE:
<223> OTHER INFORMATION: EBP

<400> SEQUENCE: 9

```
gttccgggtg gtggtgttcc gggtgaaggt gttccgggtg gtggtgttcc gggtggtggt        60
ggtgttccgg gtatcggtgt tccgggtggc                                         90
```

<210> SEQ ID NO 10
<211> LENGTH: 90
<212> TYPE: DNA
<213> ORGANISM: Artificial Sequence
<220> FEATURE:
<223> OTHER INFORMATION: EBP

<400> SEQUENCE: 10

```
gttccggcgg gtggtgttcc ggcggaaggt gttccggcgg gtggtgttcc ggcgggtggt        60
gttccggcga tcggtgttcc ggcgggtggc                                         90
```

<210> SEQ ID NO 11
<211> LENGTH: 90
<212> TYPE: DNA
<213> ORGANISM: Artificial Sequence
<220> FEATURE:
<223> OTHER INFORMATION: EBP

<400> SEQUENCE: 11

```
gtcccgggtg cgggcgtgcc gggatttgga gttccgggtg cgggtgttcc aggcggtggt        60 gttccggggcg cgggcgtgcc gggctttggc                                        90
```

<210> SEQ ID NO 12
<211> LENGTH: 90
<212> TYPE: DNA
<213> ORGANISM: Artificial Sequence
<220> FEATURE:
<223> OTHER INFORMATION: EBP

<400> SEQUENCE: 12

```
gtgccggcgg cgggcgttcc agcctttggt gtgccagcgg cgggagttcc ggccggtggc        60
gtgccggcag cgggcgtgcc ggcttttggc                                         90
```

<210> SEQ ID NO 13
<211> LENGTH: 90
<212> TYPE: DNA
<213> ORGANISM: Artificial Sequence
<220> FEATURE:
<223> OTHER INFORMATION: EBP

<400> SEQUENCE: 13

```
gtgccggcgg cgggcgttcc agcctttggt gtgccagcgg cgggagttcc ggccaaaggc        60
gtgccggcag cgggcgtgcc ggcttttggc                                         90
```

<210> SEQ ID NO 14
<211> LENGTH: 90
<212> TYPE: DNA
<213> ORGANISM: Artificial Sequence
<220> FEATURE:
<223> OTHER INFORMATION: EBP

<400> SEQUENCE: 14
gtgccggcgg cgggcgttcc agcctttggt gtgccagcgg cgggagttcc ggccgatggc    60
gtgccggcag cgggcgtgcc ggcttttggc                                    90

<210> SEQ ID NO 15
<211> LENGTH: 90
<212> TYPE: DNA
<213> ORGANISM: Artificial Sequence
<220> FEATURE:
<223> OTHER INFORMATION: EBP

<400> SEQUENCE: 15
gttccagcgt ttggcgtgcc agcgaaaggt gttccggcgt ttggggttcc cgcgaaaggt    60
gtgccggcct ttggtgtgcc ggccaaaggc                                    90

<210> SEQ ID NO 16
<211> LENGTH: 90
<212> TYPE: DNA
<213> ORGANISM: Artificial Sequence
<220> FEATURE:
<223> OTHER INFORMATION: EBP

<400> SEQUENCE: 16
gttccagcgt ttggcgtgcc agcggatggt gttccggcgt ttggggttcc cgcggatggt    60
gtgccggcct ttggtgtgcc ggccgatggc                                    90

<210> SEQ ID NO 17
<211> LENGTH: 90
<212> TYPE: DNA
<213> ORGANISM: Artificial Sequence
<220> FEATURE:
<223> OTHER INFORMATION: EBP

<400> SEQUENCE: 17
gtgccggcgc atggagttcc tgccgccggt gttcctgcgc atggtgtacc ggcaattggc    60
gttccggcac atggtgtgcc ggccgccggc                                    90

<210> SEQ ID NO 18
<211> LENGTH: 90
<212> TYPE: DNA
<213> ORGANISM: Artificial Sequence
<220> FEATURE:
<223> OTHER INFORMATION: EBP

<400> SEQUENCE: 18
gttccggccg gaggtgtacc ggcgcatggt gttccggcac atggtgtgcc ggctcacggt    60
gtgcctgcgc atggcgttcc tgcgcatggc                                    90

<210> SEQ ID NO 19
<211> LENGTH: 90
<212> TYPE: DNA
<213> ORGANISM: Artificial Sequence
<220> FEATURE:
<223> OTHER INFORMATION: EBP -continued

```
<400> SEQUENCE: 19
gtgccggcgt gcggcgttcc agcctttggt gtgccagcgt gcggagttcc ggccggtggc    60
gtgccggcat gcggcgtgcc ggcttttggc                                     90
```

```
<210> SEQ ID NO 20
<211> LENGTH: 30
<212> TYPE: PRT
<213> ORGANISM: Artificial Sequence
<220> FEATURE:
<223> OTHER INFORMATION: EBP

<400> SEQUENCE: 20

Val Pro Gly Gly Gly Val Pro Gly Ala Gly Val Pro Gly Gly Gly Val
1               5                   10                  15
Pro Gly Gly Gly Val Pro Gly Ile Gly Val Pro Gly Gly Gly
            20                  25                  30
```

```
<210> SEQ ID NO 21
<211> LENGTH: 30
<212> TYPE: PRT
<213> ORGANISM: Artificial Sequence
<220> FEATURE:
<223> OTHER INFORMATION: EBP

<400> SEQUENCE: 21

Val Pro Ala Gly Gly Val Pro Ala Ala Gly Val Pro Ala Gly Gly Val
1               5                   10                  15
Pro Ala Gly Gly Val Pro Ala Ile Gly Val Pro Ala Gly Gly
            20                  25                  30
```

```
<210> SEQ ID NO 22
<211> LENGTH: 30
<212> TYPE: PRT
<213> ORGANISM: Artificial Sequence
<220> FEATURE:
<223> OTHER INFORMATION: EBP

<400> SEQUENCE: 22

Val Pro Gly Gly Gly Val Pro Gly Lys Gly Val Pro Gly Gly Gly Val
1               5                   10                  15
Pro Gly Gly Gly Val Pro Gly Ile Gly Val Pro Gly Gly Gly
            20                  25                  30
```

```
<210> SEQ ID NO 23
<211> LENGTH: 30
<212> TYPE: PRT
<213> ORGANISM: Artificial Sequence
<220> FEATURE:
<223> OTHER INFORMATION: EBP

<400> SEQUENCE: 23

Val Pro Ala Gly Gly Val Pro Ala Lys Gly Val Pro Ala Gly Gly Val
1               5                   10                  15
Pro Ala Gly Gly Val Pro Ala Ile Gly Val Pro Ala Gly Gly
            20                  25                  30
```

```
<210> SEQ ID NO 24
<211> LENGTH: 30
<212> TYPE: PRT
<213> ORGANISM: Artificial Sequence
<220> FEATURE:
<223> OTHER INFORMATION: EBP

<400> SEQUENCE: 24
```

```
Val Pro Gly Gly Gly Val Pro Gly Asp Gly Val Pro Gly Gly Gly Val
1               5                   10                  15

Pro Gly Gly Gly Val Pro Gly Ile Gly Val Pro Gly Gly Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: EBP

<400> SEQUENCE: 25

Val Pro Ala Gly Gly Val Pro Ala Asp Gly Val Pro Ala Gly Gly Val
1               5                   10                  15

Pro Ala Gly Gly Val Pro Ala Ile Gly Val Pro Ala Gly Gly
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: EBP

<400> SEQUENCE: 26

Val Pro Gly Gly Gly Val Pro Gly Glu Gly Val Pro Gly Gly Gly Val
1               5                   10                  15

Pro Gly Gly Gly Val Pro Gly Ile Gly Val Pro Gly Gly Gly
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: EBP

<400> SEQUENCE: 27

Val Pro Ala Gly Gly Val Pro Ala Glu Gly Val Pro Ala Gly Gly Val
1               5                   10                  15

Pro Ala Gly Gly Val Pro Ala Ile Gly Val Pro Ala Gly Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: EBP

<400> SEQUENCE: 28

Val Pro Gly Ala Gly Val Pro Gly Phe Gly Val Pro Gly Ala Gly Val
1               5                   10                  15

Pro Gly Gly Gly Val Pro Gly Ala Gly Val Pro Gly Phe Gly
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: EBP
```

-continued

```
<400> SEQUENCE: 29

Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: EBP

<400> SEQUENCE: 30

Val Pro Ala Ala Gly Val Pro Ala Phe Gly Val Pro Ala Ala Gly Val
1               5                   10                  15

Pro Ala Lys Gly Val Pro Ala Ala Gly Val Pro Ala Phe Gly
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: EBP

<400> SEQUENCE: 31

Val Pro Ala Ala Gly Val Pro Ala Phe Gly Val Pro Ala Ala Gly Val
1               5                   10                  15

Pro Ala Asp Gly Val Pro Ala Ala Gly Val Pro Ala Phe Gly
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: EBP

<400> SEQUENCE: 32

Val Pro Ala Phe Gly Val Pro Ala Lys Gly Val Pro Ala Phe Gly Val
1               5                   10                  15

Pro Ala Lys Gly Val Pro Ala Phe Gly Val Pro Ala Lys Gly
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: EBP

<400> SEQUENCE: 33

Val Pro Ala Phe Gly Val Pro Ala Asp Gly Val Pro Ala Phe Gly Val
1               5                   10                  15

Pro Ala Asp Gly Val Pro Ala Phe Gly Val Pro Ala Asp Gly
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: EBP
```

<400> SEQUENCE: 34

Val Pro Ala His Gly Val Pro Ala Ala Gly Val Pro Ala His Gly Val
1               5                   10                  15

Pro Ala Ile Gly Val Pro Ala His Gly Val Pro Ala Ala Gly
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: EBP

<400> SEQUENCE: 35

Val Pro Ala Gly Gly Val Pro Ala His Gly Val Pro Ala His Gly Val
1               5                   10                  15

Pro Ala His Gly Val Pro Ala His Gly Val Pro Ala His Gly
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: EBP

<400> SEQUENCE: 36

Val Pro Ala Cys Gly Val Pro Ala Phe Gly Val Pro Ala Cys Gly Val
1               5                   10                  15

Pro Ala Gly Gly Val Pro Ala Cys Gly Val Pro Ala Phe Gly
            20                  25                  30

<210> SEQ ID NO 37
<211> LENGTH: 18
<212> TYPE: DNA
<213> ORGANISM: Artificial Sequence
<220> FEATURE:
<223> OTHER INFORMATION: anti-Flt1

<400> SEQUENCE: 37
ggcaatcagt ggtttatt                                                 18

<210> SEQ ID NO 38
<211> LENGTH: 6
<212> TYPE: PRT
<213> ORGANISM: Artificial Sequence
<220> FEATURE:
<223> OTHER INFORMATION: anti-Flt1

<400> SEQUENCE: 38

Gly Asn Gln Trp Phe Ile
1               5

<210> SEQ ID NO 39
<211> LENGTH: 66
<212> TYPE: DNA
<213> ORGANISM: Artificial Sequence
<220> FEATURE:
<223> OTHER INFORMATION: Synthetic oligonucleotides

<400> SEQUENCE: 39
ctagaaataa ttttgtttaa ctttaagaag gaggagtaca tatgggctac tgataatgat   60
cttcag                                                              66

<210> SEQ ID NO 40
<211> LENGTH: 66
<212> TYPE: DNA
<213> ORGANISM: Artificial Sequence
<220> FEATURE:
<223> OTHER INFORMATION: Synthetic oligonucleotides

<400> SEQUENCE: 40
gatcctgaag atcattatca gtagcccata tgtactcctc cttcttaaag ttaaacaaaa    60
ttattt    66

<210> SEQ ID NO 41
<211> LENGTH: 90
<212> TYPE: PRT
<213> ORGANISM: Artificial Sequence
<220> FEATURE:
<223> OTHER INFORMATION: hydrophilic EBPP[A1G4I1]3

<400> SEQUENCE: 41

Val Pro Ala Gly Gly Val Pro Ala Ala Gly Val Pro Ala Gly Gly Val
1               5                   10                  15

Pro Ala Gly Gly Val Pro Ala Ile Gly Val Pro Ala Gly Gly Val Pro
            20                  25                  30

Ala Gly Gly Val Pro Ala Ala Gly Val Pro Ala Gly Gly Val Pro Ala
        35                  40                  45

Gly Gly Val Pro Ala Ile Gly Val Pro Ala Gly Gly Val Pro Ala Gly
    50                  55                  60

Gly Val Pro Ala Ala Gly Val Pro Ala Gly Gly Val Pro Ala Gly Gly
65                  70                  75                  80

Val Pro Ala Ile Gly Val Pro Ala Gly Gly
            85                  90

<210> SEQ ID NO 42
<211> LENGTH: 180
<212> TYPE: PRT
<213> ORGANISM: Artificial Sequence
<220> FEATURE:
<223> OTHER INFORMATION: hydrophilic EBPP[A1G4I1]6

<400> SEQUENCE: 42

Val Pro Ala Gly Gly Val Pro Ala Ala Gly Val Pro Ala Gly Gly Val
1               5                   10                  15

Pro Ala Gly Gly Val Pro Ala Ile Gly Val Pro Ala Gly Gly Val Pro
            20                  25                  30

Ala Gly Gly Val Pro Ala Ala Gly Val Pro Ala Gly Gly Val Pro Ala
        35                  40                  45

Gly Gly Val Pro Ala Ile Gly Val Pro Ala Gly Gly Val Pro Ala Gly
    50                  55                  60

Gly Val Pro Ala Ala Gly Val Pro Ala Gly Gly Val Pro Ala Gly Gly
65                  70                  75                  80

Val Pro Ala Ile Gly Val Pro Ala Gly Gly Val Pro Ala Gly Gly Val
            85                  90                  95

Pro Ala Ala Gly Val Pro Ala Gly Gly Val Pro Ala Gly Gly Val Pro
            100                 105                 110

Ala Ile Gly Val Pro Ala Gly Gly Val Pro Ala Gly Gly Val Pro Ala
        115                 120                 125

Ala Gly Val Pro Ala Gly Gly Val Pro Ala Gly Gly Val Pro Ala Ile
    130                 135                 140

Gly Val Pro Ala Gly Gly Val Pro Ala Gly Gly Val Pro Ala Ala Gly
145                 150                 155                 160

Val Pro Ala Gly Gly Val Pro Ala Gly Gly Val Pro Ala Ile Gly Val
                165                 170                 175

Pro Ala Gly Gly
            180

<210> SEQ ID NO 43
<211> LENGTH: 360
<212> TYPE: PRT
<213> ORGANISM: Artificial Sequence
<220> FEATURE:
<223> OTHER INFORMATION: hydrophilic EBPP[A1G4I1]12

<400> SEQUENCE: 43

Val Pro Ala Gly Gly Val Pro Ala Ala Gly Val Pro Ala Gly Gly Val
1               5                   10                  15

Pro Ala Gly Gly Val Pro Ala Ile Gly Val Pro Ala Gly Gly Val Pro
                20                  25                  30

Ala Gly Gly Val Pro Ala Ala Gly Val Pro Ala Gly Gly Val Pro Ala
            35                  40                  45

Gly Gly Val Pro Ala Ile Gly Val Pro Ala Gly Gly Val Pro Ala Gly
        50                  55                  60

Gly Val Pro Ala Ala Gly Val Pro Ala Gly Gly Val Pro Ala Gly Gly
65                  70                  75                  80

Val Pro Ala Ile Gly Val Pro Ala Gly Gly Val Pro Ala Gly Gly Val
                85                  90                  95

Pro Ala Ala Gly Val Pro Ala Gly Gly Val Pro Ala Gly Gly Val Pro
                100                 105                 110

Ala Ile Gly Val Pro Ala Gly Gly Val Pro Ala Gly Gly Val Pro Ala
            115                 120                 125

Ala Gly Val Pro Ala Gly Gly Val Pro Ala Gly Gly Val Pro Ala Ile
        130                 135                 140

Gly Val Pro Ala Gly Gly Val Pro Ala Gly Gly Val Pro Ala Ala Gly
145                 150                 155                 160

Val Pro Ala Gly Gly Val Pro Ala Gly Gly Val Pro Ala Ile Gly Val
                165                 170                 175

Pro Ala Gly Gly Val Pro Ala Gly Gly Val Pro Ala Ala Gly Val Pro
            180                 185                 190

Ala Gly Gly Val Pro Ala Gly Gly Val Pro Ala Ile Gly Val Pro Ala
        195                 200                 205

Gly Gly Val Pro Ala Gly Gly Val Pro Ala Ala Gly Val Pro Ala Gly
    210                 215                 220

Gly Val Pro Ala Gly Gly Val Pro Ala Ile Gly Val Pro Ala Gly Gly
225                 230                 235                 240

Val Pro Ala Gly Gly Val Pro Ala Ala Gly Val Pro Ala Gly Gly Val
                245                 250                 255

Pro Ala Gly Gly Val Pro Ala Ile Gly Val Pro Ala Gly Gly Val Pro
            260                 265                 270

Ala Gly Gly Val Pro Ala Ala Gly Val Pro Ala Gly Gly Val Pro Ala
        275                 280                 285

Gly Gly Val Pro Ala Ile Gly Val Pro Ala Gly Gly Val Pro Ala Gly
    290                 295                 300

Gly Val Pro Ala Ala Gly Val Pro Ala Gly Gly Val Pro Ala Gly Gly
305                 310                 315                 320

Val Pro Ala Ile Gly Val Pro Ala Gly Gly Val Pro Ala Gly Gly Val
                325                 330                 335

Pro Ala Ala Gly Val Pro Ala Gly Gly Val Pro Ala Gly Gly Val Pro
            340                 345                 350

Ala Ile Gly Val Pro Ala Gly Gly
        355                 360

<210> SEQ ID NO 44
<211> LENGTH: 720
<212> TYPE: PRT
<213> ORGANISM: Artificial Sequence
<220> FEATURE:
<223> OTHER INFORMATION: hydrophilic EBPP[A1G4I1]24

<400> SEQUENCE: 44

Val Pro Ala Gly Gly Val Pro Ala Ala Gly Val Pro Ala Gly Gly Val
1               5                   10                  15

Pro Ala Gly Gly Val Pro Ala Ile Gly Val Pro Ala Gly Gly Val Pro
            20                  25                  30

Ala Gly Gly Val Pro Ala Ala Gly Val Pro Ala Gly Gly Val Pro Ala
        35                  40                  45

Gly Gly Val Pro Ala Ile Gly Val Pro Ala Gly Gly Val Pro Ala Gly
    50                  55                  60

Gly Val Pro Ala Ala Gly Val Pro Ala Gly Gly Val Pro Ala Gly Gly
65                  70                  75                  80

Val Pro Ala Ile Gly Val Pro Ala Gly Gly Val Pro Ala Gly Gly Val
                85                  90                  95

Pro Ala Ala Gly Val Pro Ala Gly Gly Val Pro Ala Gly Gly Val Pro
            100                 105                 110

Ala Ile Gly Val Pro Ala Gly Gly Val Pro Ala Gly Gly Val Pro Ala
        115                 120                 125

Ala Gly Val Pro Ala Gly Gly Val Pro Ala Gly Gly Val Pro Ala Ile
    130                 135                 140

Gly Val Pro Ala Gly Gly Val Pro Ala Gly Gly Val Pro Ala Ala Gly
145                 150                 155                 160

Val Pro Ala Gly Gly Val Pro Ala Gly Gly Val Pro Ala Ile Gly Val
                165                 170                 175

Pro Ala Gly Gly Val Pro Ala Gly Gly Val Pro Ala Ala Gly Val Pro
            180                 185                 190

Ala Gly Gly Val Pro Ala Gly Gly Val Pro Ala Ile Gly Val Pro Ala
        195                 200                 205

Gly Gly Val Pro Ala Gly Gly Val Pro Ala Ala Gly Val Pro Ala Gly
    210                 215                 220

Gly Val Pro Ala Gly Gly Val Pro Ala Ile Gly Val Pro Ala Gly Gly
225                 230                 235                 240

Val Pro Ala Gly Gly Val Pro Ala Ala Gly Val Pro Ala Gly Gly Val
                245                 250                 255

Pro Ala Gly Gly Val Pro Ala Ile Gly Val Pro Ala Gly Gly Val Pro
            260                 265                 270

Ala Gly Gly Val Pro Ala Ala Gly Val Pro Ala Gly Gly Val Pro Ala
        275                 280                 285

Gly Gly Val Pro Ala Ile Gly Val Pro Ala Gly Gly Val Pro Ala Gly
    290                 295                 300

Gly Val Pro Ala Ala Gly Val Pro Ala Gly Gly Val Pro Ala Gly Gly
305                 310                 315                 320

-continued

```
Val Pro Ala Ile Gly Val Pro Ala Gly Gly Val
            325                 330             335

Pro Ala Ala Gly Val Pro Ala Gly Gly Val Pro Ala Gly Gly Val Pro
            340                 345             350

Ala Ile Gly Val Pro Ala Gly Gly Val Pro Ala Gly Gly Val Pro Ala
            355                 360             365

Ala Gly Val Pro Ala Gly Gly Val Pro Ala Gly Gly Val Pro Ala Ile
            370                 375             380

Gly Val Pro Ala Gly Gly Val Pro Ala Gly Gly Val Pro Ala Ala Gly
385                 390             395                 400

Val Pro Ala Gly Gly Val Pro Ala Gly Gly Val Pro Ala Ile Gly Val
            405                 410             415

Pro Ala Gly Gly Val Pro Ala Gly Gly Val Pro Ala Ala Gly Val Pro
            420                 425             430

Ala Gly Gly Val Pro Ala Gly Gly Val Pro Ala Ile Gly Val Pro Ala
            435                 440             445

Gly Gly Val Pro Ala Gly Gly Val Pro Ala Ala Gly Val Pro Ala Gly
            450                 455             460

Gly Val Pro Ala Gly Gly Val Pro Ala Ile Gly Val Pro Ala Gly Gly
465                 470             475                 480

Val Pro Ala Gly Gly Val Pro Ala Ala Gly Val Pro Ala Gly Gly Val
            485                 490             495

Pro Ala Gly Gly Val Pro Ala Ile Gly Val Pro Ala Gly Gly Val Pro
            500                 505             510

Ala Gly Gly Val Pro Ala Ala Gly Val Pro Ala Gly Gly Val Pro Ala
            515                 520             525

Gly Gly Val Pro Ala Ile Gly Val Pro Ala Gly Gly Val Pro Ala Gly
            530                 535             540

Gly Val Pro Ala Ala Gly Val Pro Ala Gly Gly Val Pro Ala Gly Gly
545                 550             555                 560

Val Pro Ala Ile Gly Val Pro Ala Gly Gly Val Pro Ala Gly Gly Val
            565                 570             575

Pro Ala Ala Gly Val Pro Ala Gly Gly Val Pro Ala Gly Gly Val Pro
            580                 585             590

Ala Ile Gly Val Pro Ala Gly Gly Val Pro Ala Gly Gly Val Pro Ala
            595                 600             605

Ala Gly Val Pro Ala Gly Gly Val Pro Ala Gly Gly Val Pro Ala Ile
            610                 615             620

Gly Val Pro Ala Gly Gly Val Pro Ala Gly Gly Val Pro Ala Ala Gly
625                 630             635                 640

Val Pro Ala Gly Gly Val Pro Ala Gly Gly Val Pro Ala Ile Gly Val
            645                 650             655

Pro Ala Gly Gly Val Pro Ala Gly Gly Val Pro Ala Ala Gly Val Pro
            660                 665             670

Ala Gly Gly Val Pro Ala Gly Gly Val Pro Ala Ile Gly Val Pro Ala
            675                 680             685

Gly Gly Val Pro Ala Gly Gly Val Pro Ala Ala Gly Val Pro Ala Gly
            690                 695             700

Gly Val Pro Ala Gly Gly Val Pro Ala Ile Gly Val Pro Ala Gly Gly
705                 710             715                 720
```

<210> SEQ ID NO 45
<211> LENGTH: 360

```
<212> TYPE: PRT
<213> ORGANISM: Artificial Sequence
<220> FEATURE:
<223> OTHER INFORMATION: hydrophilic EBPP[E1G4I1]12

<400> SEQUENCE: 45

Val Pro Ala Gly Gly Val Pro Ala Glu Gly Val Pro Ala Gly Gly Val
1               5                   10                  15

Pro Ala Gly Gly Val Pro Ala Ile Gly Val Pro Ala Gly Gly Val Pro
            20                  25                  30

Ala Gly Gly Val Pro Ala Glu Gly Val Pro Ala Gly Gly Val Pro Ala
        35                  40                  45

Gly Gly Val Pro Ala Ile Gly Val Pro Ala Gly Gly Val Pro Ala Gly
    50                  55                  60

Gly Val Pro Ala Glu Gly Val Pro Ala Gly Gly Val Pro Ala Gly Gly
65                  70                  75                  80

Val Pro Ala Ile Gly Val Pro Ala Gly Gly Val Pro Ala Gly Gly Val
            85                  90                  95

Pro Ala Glu Gly Val Pro Ala Gly Gly Val Pro Ala Gly Gly Val Pro
            100                 105                 110

Ala Ile Gly Val Pro Ala Gly Gly Val Pro Ala Gly Gly Val Pro Ala
        115                 120                 125

Glu Gly Val Pro Ala Gly Gly Val Pro Ala Gly Gly Val Pro Ala Ile
    130                 135                 140

Gly Val Pro Ala Gly Gly Val Pro Ala Gly Gly Val Pro Ala Glu Gly
145                 150                 155                 160

Val Pro Ala Gly Gly Val Pro Ala Gly Gly Val Pro Ala Ile Gly Val
                165                 170                 175

Pro Ala Gly Gly Val Pro Ala Gly Gly Val Pro Ala Glu Gly Val Pro
            180                 185                 190

Ala Gly Gly Val Pro Ala Gly Gly Val Pro Ala Ile Gly Val Pro Ala
        195                 200                 205

Gly Gly Val Pro Ala Gly Gly Val Pro Ala Glu Gly Val Pro Ala Gly
    210                 215                 220

Gly Val Pro Ala Gly Gly Val Pro Ala Ile Gly Val Pro Ala Gly Gly
225                 230                 235                 240

Val Pro Ala Gly Gly Val Pro Ala Glu Gly Val Pro Ala Gly Gly Val
                245                 250                 255

Pro Ala Gly Gly Val Pro Ala Ile Gly Val Pro Ala Gly Gly Val Pro
            260                 265                 270

Ala Gly Gly Val Pro Ala Glu Gly Val Pro Ala Gly Gly Val Pro Ala
        275                 280                 285

Gly Gly Val Pro Ala Ile Gly Val Pro Ala Gly Gly Val Pro Ala Gly
    290                 295                 300

Gly Val Pro Ala Glu Gly Val Pro Ala Gly Gly Val Pro Ala Gly Gly
305                 310                 315                 320

Val Pro Ala Ile Gly Val Pro Ala Gly Gly Val Pro Ala Gly Gly Val
                325                 330                 335

Pro Ala Glu Gly Val Pro Ala Gly Gly Val Pro Ala Gly Gly Val Pro
            340                 345                 350

Ala Ile Gly Val Pro Ala Gly Gly
        355                 360

<210> SEQ ID NO 46
<211> LENGTH: 360
```

<212> TYPE: PRT
<213> ORGANISM: Artificial Sequence
<220> FEATURE:
<223> OTHER INFORMATION: hydrophobic EBPP[G1A3F2]12

<400> SEQUENCE: 46

```
Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly Val Pro
                20                  25                  30

Ala Ala Gly Val Pro Ala Phe Gly Val Pro Ala Ala Gly Val Pro Ala
            35                  40                  45

Gly Gly Val Pro Ala Ala Gly Val Pro Ala Phe Gly Val Pro Ala Ala
        50                  55                  60

Gly Val Pro Ala Phe Gly Val Pro Ala Ala Gly Val Pro Ala Gly Gly
65                  70                  75                  80

Val Pro Ala Ala Gly Val Pro Ala Phe Gly Val Pro Ala Ala Gly Val
                85                  90                  95

Pro Ala Phe Gly Val Pro Ala Ala Gly Val Pro Ala Gly Gly Val Pro
            100                 105                 110

Ala Ala Gly Val Pro Ala Phe Gly Val Pro Ala Ala Gly Val Pro Ala
        115                 120                 125

Phe Gly Val Pro Ala Ala Gly Val Pro Ala Gly Gly Val Pro Ala Ala
130                 135                 140

Gly Val Pro Ala Phe Gly Val Pro Ala Ala Gly Val Pro Ala Phe Gly
145                 150                 155                 160

Val Pro Ala Ala Gly Val Pro Ala Gly Gly Val Pro Ala Ala Gly Val
                165                 170                 175

Pro Ala Phe Gly Val Pro Ala Ala Gly Val Pro Ala Phe Gly Val Pro
            180                 185                 190

Ala Ala Gly Val Pro Ala Gly Gly Val Pro Ala Ala Gly Val Pro Ala
        195                 200                 205

Phe Gly Val Pro Ala Ala Gly Val Pro Ala Phe Gly Val Pro Ala Ala
210                 215                 220

Gly Val Pro Ala Gly Gly Val Pro Ala Ala Gly Val Pro Ala Phe Gly
225                 230                 235                 240

Val Pro Ala Ala Gly Val Pro Ala Phe Gly Val Pro Ala Ala Gly Val
                245                 250                 255

Pro Ala Gly Gly Val Pro Ala Ala Gly Val Pro Ala Phe Gly Val Pro
            260                 265                 270

Ala Ala Gly Val Pro Ala Phe Gly Val Pro Ala Ala Gly Val Pro Ala
        275                 280                 285

Gly Gly Val Pro Ala Ala Gly Val Pro Ala Phe Gly Val Pro Ala Ala
290                 295                 300

Gly Val Pro Ala Phe Gly Val Pro Ala Ala Gly Val Pro Ala Gly Gly
305                 310                 315                 320

Val Pro Ala Ala Gly Val Pro Ala Phe Gly Val Pro Ala Ala Gly Val
                325                 330                 335

Pro Ala Phe Gly Val Pro Ala Ala Gly Val Pro Ala Gly Gly Val Pro
            340                 345                 350

Ala Ala Gly Val Pro Ala Phe Gly
        355                 360
```

<210> SEQ ID NO 47
<211> LENGTH: 720

<210> TYPE: PRT
<213> ORGANISM: Artificial Sequence
<220> FEATURE:
<223> OTHER INFORMATION: hydrophobic EBPP[G1A3F2]24

<400> SEQUENCE: 47

```
Val Pro Ala Ala Gly Val Pro Ala Phe Gly Val Pro Ala Ala Gly Val
1               5                   10                  15

Pro Ala Gly Gly Val Pro Ala Ala Gly Val Pro Ala Phe Gly Val Pro
            20                  25                  30

Ala Ala Gly Val Pro Ala Phe Gly Val Pro Ala Ala Gly Val Pro Ala
        35                  40                  45

Gly Gly Val Pro Ala Ala Gly Val Pro Ala Phe Gly Val Pro Ala Ala
    50                  55                  60

Gly Val Pro Ala Phe Gly Val Pro Ala Ala Gly Val Pro Ala Gly Gly
65                  70                  75                  80

Val Pro Ala Ala Gly Val Pro Ala Phe Gly Val Pro Ala Ala Gly Val
            85                  90                  95

Pro Ala Phe Gly Val Pro Ala Ala Gly Val Pro Ala Gly Gly Val Pro
            100                 105                 110

Ala Ala Gly Val Pro Ala Phe Gly Val Pro Ala Ala Gly Val Pro Ala
        115                 120                 125

Phe Gly Val Pro Ala Ala Gly Val Pro Ala Gly Gly Val Pro Ala Ala
    130                 135                 140

Gly Val Pro Ala Phe Gly Val Pro Ala Ala Gly Val Pro Ala Phe Gly
145                 150                 155                 160

Val Pro Ala Ala Gly Val Pro Ala Gly Gly Val Pro Ala Ala Gly Val
            165                 170                 175

Pro Ala Phe Gly Val Pro Ala Ala Gly Val Pro Ala Phe Gly Val Pro
            180                 185                 190

Ala Ala Gly Val Pro Ala Gly Gly Val Pro Ala Ala Gly Val Pro Ala
        195                 200                 205

Phe Gly Val Pro Ala Ala Gly Val Pro Ala Phe Gly Val Pro Ala Ala
    210                 215                 220

Gly Val Pro Ala Gly Gly Val Pro Ala Ala Gly Val Pro Ala Phe Gly
225                 230                 235                 240

Val Pro Ala Ala Gly Val Pro Ala Phe Gly Val Pro Ala Ala Gly Val
            245                 250                 255

Pro Ala Gly Gly Val Pro Ala Ala Gly Val Pro Ala Phe Gly Val Pro
            260                 265                 270

Ala Ala Gly Val Pro Ala Phe Gly Val Pro Ala Ala Gly Val Pro Ala
        275                 280                 285

Gly Gly Val Pro Ala Ala Gly Val Pro Ala Phe Gly Val Pro Ala Ala
    290                 295                 300

Gly Val Pro Ala Phe Gly Val Pro Ala Ala Gly Val Pro Ala Gly Gly
305                 310                 315                 320

Val Pro Ala Ala Gly Val Pro Ala Phe Gly Val Pro Ala Ala Gly Val
            325                 330                 335

Pro Ala Phe Gly Val Pro Ala Ala Gly Val Pro Ala Gly Gly Val Pro
            340                 345                 350

Ala Ala Gly Val Pro Ala Phe Gly Val Pro Ala Ala Gly Val Pro Ala
        355                 360                 365

Phe Gly Val Pro Ala Ala Gly Val Pro Ala Gly Gly Val Pro Ala Ala
    370                 375                 380
```

-continued

Gly Val Pro Ala Phe Gly Val Pro Ala Gly Pro Ala Phe Gly
385                 390                 395                 400

Val Pro Ala Ala Gly Val Pro Ala Gly Gly Val Pro Ala Ala Gly Val
            405                 410                 415

Pro Ala Phe Gly Val Pro Ala Gly Gly Val Pro Ala Phe Gly Val Pro
        420                 425                 430

Ala Ala Gly Val Pro Ala Gly Gly Val Pro Ala Ala Gly Val Pro Ala
        435                 440                 445

Phe Gly Val Pro Ala Ala Gly Val Pro Ala Phe Gly Val Pro Ala Ala
    450                 455                 460

Gly Val Pro Ala Gly Gly Val Pro Ala Ala Gly Val Pro Ala Phe Gly
465                 470                 475                 480

Val Pro Ala Ala Gly Val Pro Ala Phe Gly Val Pro Ala Ala Gly Val
            485                 490                 495

Pro Ala Gly Gly Val Pro Ala Ala Gly Val Pro Ala Phe Gly Val Pro
        500                 505                 510

Ala Ala Gly Val Pro Ala Phe Gly Val Pro Ala Ala Gly Val Pro Ala
        515                 520                 525

Gly Gly Val Pro Ala Ala Gly Val Pro Ala Phe Gly Val Pro Ala Ala
530                 535                 540

Gly Val Pro Ala Phe Gly Val Pro Ala Ala Gly Val Pro Ala Gly Gly
545                 550                 555                 560

Val Pro Ala Ala Gly Val Pro Ala Phe Gly Val Pro Ala Ala Gly Val
            565                 570                 575

Pro Ala Phe Gly Val Pro Ala Ala Gly Val Pro Ala Gly Gly Val Pro
        580                 585                 590

Ala Ala Gly Val Pro Ala Phe Gly Val Pro Ala Ala Gly Val Pro Ala
        595                 600                 605

Phe Gly Val Pro Ala Ala Gly Val Pro Ala Gly Gly Val Pro Ala Ala
    610                 615                 620

Gly Val Pro Ala Phe Gly Val Pro Ala Ala Gly Val Pro Ala Phe Gly
625                 630                 635                 640

Val Pro Ala Ala Gly Val Pro Ala Gly Gly Val Pro Ala Ala Gly Val
            645                 650                 655

Pro Ala Phe Gly Val Pro Ala Ala Gly Val Pro Ala Phe Gly Val Pro
        660                 665                 670

Ala Ala Gly Val Pro Ala Gly Gly Val Pro Ala Ala Gly Val Pro Ala
        675                 680                 685

Phe Gly Val Pro Ala Ala Gly Val Pro Ala Phe Gly Val Pro Ala Ala
    690                 695                 700

Gly Val Pro Ala Gly Gly Val Pro Ala Ala Gly Val Pro Ala Phe Gly
705                 710                 715                 720

<210> SEQ ID NO 48
<211> LENGTH: 96
<212> TYPE: PRT
<213> ORGANISM: Artificial Sequence
<220> FEATURE:
<223> OTHER INFORMATION: anti-Flt1-EBPP[A1G4I1]3

<400> SEQUENCE: 48

Gly Asn Gln Trp Phe Ile Val Pro Ala Gly Gly Val Pro Ala Ala Gly
1               5                   10                  15

Val Pro Ala Gly Gly Val Pro Ala Gly Gly Val Pro Ala Ile Gly Val
            20                  25                  30

```
Pro Ala Gly Gly Val Pro Ala Gly Gly Val Pro Ala Ala Gly Val Pro
            35                  40                  45

Ala Gly Gly Val Pro Ala Gly Gly Val Pro Ala Ile Gly Val Pro Ala
 50                  55                  60

Gly Gly Val Pro Ala Gly Gly Val Pro Ala Ala Gly Val Pro Ala Gly
 65                  70                  75                  80

Gly Val Pro Ala Gly Gly Val Pro Ala Ile Gly Val Pro Ala Gly Gly
                85                  90                  95

<210> SEQ ID NO 49
<211> LENGTH: 186
<212> TYPE: PRT
<213> ORGANISM: Artificial Sequence
<220> FEATURE:
<223> OTHER INFORMATION: anti-Flt1-EBPP [A1G4I1]6

<400> SEQUENCE: 49

Gly Asn Gln Trp Phe Ile Val Pro Ala Gly Gly Val Pro Ala Ala Gly
 1               5                  10                  15

Val Pro Ala Gly Gly Val Pro Ala Gly Gly Val Pro Ala Ile Gly Val
                20                  25                  30

Pro Ala Gly Gly Val Pro Ala Gly Gly Val Pro Ala Ala Gly Val Pro
            35                  40                  45

Ala Gly Gly Val Pro Ala Gly Gly Val Pro Ala Ile Gly Val Pro Ala
 50                  55                  60

Gly Gly Val Pro Ala Gly Gly Val Pro Ala Ala Gly Val Pro Ala Gly
 65                  70                  75                  80

Gly Val Pro Ala Gly Gly Val Pro Ala Ile Gly Val Pro Ala Gly Gly
                85                  90                  95

Val Pro Ala Gly Gly Val Pro Ala Ala Gly Val Pro Ala Gly Gly Val
               100                 105                 110

Pro Ala Gly Gly Val Pro Ala Ile Gly Val Pro Ala Gly Gly Val Pro
           115                 120                 125

Ala Gly Gly Val Pro Ala Ala Gly Val Pro Ala Gly Gly Val Pro Ala
130                 135                 140

Gly Gly Val Pro Ala Ile Gly Val Pro Ala Gly Gly Val Pro Ala Gly
145                 150                 155                 160

Gly Val Pro Ala Ala Gly Val Pro Ala Gly Gly Val Pro Ala Gly Gly
                165                 170                 175

Val Pro Ala Ile Gly Val Pro Ala Gly Gly
            180                 185

<210> SEQ ID NO 50
<211> LENGTH: 366
<212> TYPE: PRT
<213> ORGANISM: Artificial Sequence
<220> FEATURE:
<223> OTHER INFORMATION: anti-Flt1-EBPP[A1G4I1]12

<400> SEQUENCE: 50

Gly Asn Gln Trp Phe Ile Val Pro Ala Gly Gly Val Pro Ala Ala Gly
 1               5                  10                  15

Val Pro Ala Gly Gly Val Pro Ala Gly Gly Val Pro Ala Ile Gly Val
                20                  25                  30

Pro Ala Gly Gly Val Pro Ala Gly Gly Val Pro Ala Ala Gly Val Pro
            35                  40                  45

Ala Gly Gly Val Pro Ala Gly Gly Val Pro Ala Ile Gly Val Pro Ala
 50                  55                  60
```

Gly Gly Val Pro Ala Gly Val Pro Ala Gly Val Pro Ala Gly
65                  70                  75                  80

Gly Val Pro Ala Gly Val Pro Ala Ile Gly Val Pro Ala Gly Gly
                85                  90                  95

Val Pro Ala Gly Gly Val Pro Ala Ala Gly Val Pro Ala Gly Gly Val
            100                 105                 110

Pro Ala Gly Gly Val Pro Ala Ile Gly Val Pro Ala Gly Gly Val Pro
        115                 120                 125

Ala Gly Gly Val Pro Ala Ala Gly Val Pro Ala Gly Gly Val Pro Ala
130                 135                 140

Gly Gly Val Pro Ala Ile Gly Val Pro Ala Gly Gly Val Pro Ala Gly
145                 150                 155                 160

Gly Val Pro Ala Ala Gly Val Pro Ala Gly Gly Val Pro Ala Gly Gly
                165                 170                 175

Val Pro Ala Ile Gly Val Pro Ala Gly Gly Val Pro Ala Gly Gly Val
            180                 185                 190

Pro Ala Ala Gly Val Pro Ala Gly Gly Val Pro Ala Gly Gly Val Pro
        195                 200                 205

Ala Ile Gly Val Pro Ala Gly Gly Val Pro Ala Gly Gly Val Pro Ala
    210                 215                 220

Ala Gly Val Pro Ala Gly Gly Val Pro Ala Gly Gly Val Pro Ala Ile
225                 230                 235                 240

Gly Val Pro Ala Gly Gly Val Pro Ala Gly Gly Val Pro Ala Ala Gly
                245                 250                 255

Val Pro Ala Gly Gly Val Pro Ala Gly Gly Val Pro Ala Ile Gly Val
            260                 265                 270

Pro Ala Gly Gly Val Pro Ala Gly Gly Val Pro Ala Ala Gly Val Pro
        275                 280                 285

Ala Gly Gly Val Pro Ala Gly Gly Val Pro Ala Ile Gly Val Pro Ala
    290                 295                 300

Gly Gly Val Pro Ala Gly Gly Val Pro Ala Ala Gly Val Pro Ala Gly
305                 310                 315                 320

Gly Val Pro Ala Gly Gly Val Pro Ala Ile Gly Val Pro Ala Gly Gly
                325                 330                 335

Val Pro Ala Gly Gly Val Pro Ala Ala Gly Val Pro Ala Gly Gly Val
            340                 345                 350

Pro Ala Gly Gly Val Pro Ala Ile Gly Val Pro Ala Gly Gly
        355                 360                 365

<210> SEQ ID NO 51
<211> LENGTH: 726
<212> TYPE: PRT
<213> ORGANISM: Artificial Sequence
<220> FEATURE:
<223> OTHER INFORMATION: anti-Flt1-EBPP[A1G4I1]24

<400> SEQUENCE: 51

Gly Asn Gln Trp Phe Ile Val Pro Ala Gly Gly Val Pro Ala Ala Gly
1               5                   10                  15

Val Pro Ala Gly Gly Val Pro Ala Gly Gly Val Pro Ala Ile Gly Val
            20                  25                  30

Pro Ala Gly Gly Val Pro Ala Gly Gly Val Pro Ala Ala Gly Val Pro
        35                  40                  45

Ala Gly Gly Val Pro Ala Gly Gly Val Pro Ala Ile Gly Val Pro Ala
    50                  55                  60

-continued

Gly Gly Val Pro Ala Gly Val Pro Ala Ala Gly Val Pro Ala Gly
65                  70                  75                  80

Gly Val Pro Ala Gly Val Pro Ala Ile Gly Val Pro Ala Gly Gly
                85                  90                  95

Val Pro Ala Gly Gly Val Pro Ala Ala Gly Val Pro Ala Gly Gly Val
            100                 105                 110

Pro Ala Gly Gly Val Pro Ala Ile Gly Val Pro Ala Gly Gly Val Pro
            115                 120                 125

Ala Gly Gly Val Pro Ala Ala Gly Val Pro Ala Gly Gly Val Pro Ala
        130                 135                 140

Gly Gly Val Pro Ala Ile Gly Val Pro Ala Gly Gly Val Pro Ala Gly
145                 150                 155                 160

Gly Val Pro Ala Ala Gly Val Pro Ala Gly Gly Val Pro Ala Gly Gly
                165                 170                 175

Val Pro Ala Ile Gly Val Pro Ala Gly Gly Val Pro Ala Gly Gly Val
            180                 185                 190

Pro Ala Ala Gly Val Pro Ala Gly Gly Val Pro Ala Gly Gly Val Pro
            195                 200                 205

Ala Ile Gly Val Pro Ala Gly Gly Val Pro Ala Gly Gly Val Pro Ala
        210                 215                 220

Ala Gly Val Pro Ala Gly Gly Val Pro Ala Gly Gly Val Pro Ala Ile
225                 230                 235                 240

Gly Val Pro Ala Gly Gly Val Pro Ala Gly Gly Val Pro Ala Ala Gly
                245                 250                 255

Val Pro Ala Gly Gly Val Pro Ala Gly Gly Val Pro Ala Ile Gly Val
            260                 265                 270

Pro Ala Gly Gly Val Pro Ala Gly Gly Val Pro Ala Ala Gly Val Pro
            275                 280                 285

Ala Gly Gly Val Pro Ala Gly Gly Val Pro Ala Ile Gly Val Pro Ala
        290                 295                 300

Gly Gly Val Pro Ala Gly Gly Val Pro Ala Ala Gly Val Pro Ala Gly
305                 310                 315                 320

Gly Val Pro Ala Gly Gly Val Pro Ala Ile Gly Val Pro Ala Gly Gly
                325                 330                 335

Val Pro Ala Gly Gly Val Pro Ala Ala Gly Val Pro Ala Gly Gly Val
            340                 345                 350

Pro Ala Gly Gly Val Pro Ala Ile Gly Val Pro Ala Gly Gly Val Pro
            355                 360                 365

Ala Gly Gly Val Pro Ala Ala Gly Val Pro Ala Gly Gly Val Pro Ala
        370                 375                 380

Gly Gly Val Pro Ala Ile Gly Val Pro Ala Gly Gly Val Pro Ala Gly
385                 390                 395                 400

Gly Val Pro Ala Ala Gly Val Pro Ala Gly Gly Val Pro Ala Gly Gly
                405                 410                 415

Val Pro Ala Ile Gly Val Pro Ala Gly Gly Val Pro Ala Gly Gly Val
            420                 425                 430

Pro Ala Ala Gly Val Pro Ala Gly Gly Val Pro Ala Gly Gly Val Pro
            435                 440                 445

Ala Ile Gly Val Pro Ala Gly Gly Val Pro Ala Gly Gly Val Pro Ala
        450                 455                 460

Ala Gly Val Pro Ala Gly Gly Val Pro Ala Gly Gly Val Pro Ala Ile
465                 470                 475                 480

Gly Val Pro Ala Gly Gly Val Pro Ala Gly Gly Val Pro Ala Ala Gly
            485                 490                 495

Val Pro Ala Gly Gly Val Pro Ala Gly Gly Val Pro Ala Ile Gly Val
        500                 505                 510

Pro Ala Gly Gly Val Pro Ala Gly Gly Val Pro Ala Ala Gly Val Pro
        515                 520                 525

Ala Gly Gly Val Pro Ala Gly Gly Val Pro Ala Ile Gly Val Pro Ala
        530                 535                 540

Gly Gly Val Pro Ala Gly Gly Val Pro Ala Ala Gly Val Pro Ala Gly
545                 550                 555                 560

Gly Val Pro Ala Gly Gly Val Pro Ala Ile Gly Val Pro Ala Gly Gly
            565                 570                 575

Val Pro Ala Gly Gly Val Pro Ala Ala Gly Val Pro Ala Gly Gly Val
        580                 585                 590

Pro Ala Gly Gly Val Pro Ala Ile Gly Val Pro Ala Gly Gly Val Pro
        595                 600                 605

Ala Gly Gly Val Pro Ala Ala Gly Val Pro Ala Gly Gly Val Pro Ala
        610                 615                 620

Gly Gly Val Pro Ala Ile Gly Val Pro Ala Gly Gly Val Pro Ala Gly
625                 630                 635                 640

Gly Val Pro Ala Ala Gly Val Pro Ala Gly Gly Val Pro Ala Gly Gly
            645                 650                 655

Val Pro Ala Ile Gly Val Pro Ala Gly Gly Val Pro Ala Gly Gly Val
        660                 665                 670

Pro Ala Ala Gly Val Pro Ala Gly Gly Val Pro Ala Gly Gly Val Pro
        675                 680                 685

Ala Ile Gly Val Pro Ala Gly Gly Val Pro Ala Gly Gly Val Pro Ala
        690                 695                 700

Ala Gly Val Pro Ala Gly Gly Val Pro Ala Gly Gly Val Pro Ala Ile
705                 710                 715                 720

Gly Val Pro Ala Gly Gly
            725

<210> SEQ ID NO 52
<211> LENGTH: 726
<212> TYPE: PRT
<213> ORGANISM: Artificial Sequence
<220> FEATURE:
<223> OTHER INFORMATION: anti-Flt1-EBPP[E1G4I1]12-EBPP[G1A3F2]12

<400> SEQUENCE: 52

Gly Asn Gln Trp Phe Ile Val Pro Ala Gly Gly Val Pro Ala Glu Gly
1               5                   10                  15

Val Pro Ala Gly Gly Val Pro Ala Gly Gly Val Pro Ala Ile Gly Val
            20                  25                  30

Pro Ala Gly Gly Val Pro Ala Gly Gly Val Pro Ala Glu Gly Val Pro
        35                  40                  45

Ala Gly Gly Val Pro Ala Gly Gly Val Pro Ala Ile Gly Val Pro Ala
        50                  55                  60

Gly Gly Val Pro Ala Gly Gly Val Pro Ala Glu Gly Val Pro Ala Gly
65                  70                  75                  80

Gly Val Pro Ala Gly Gly Val Pro Ala Ile Gly Val Pro Ala Gly Gly
                85                  90                  95

Val Pro Ala Gly Gly Val Pro Ala Glu Gly Val Pro Ala Gly Gly Val
            100                 105                 110

```
Pro Ala Gly Gly Val Pro Ala Ile Gly Val Pro Ala Gly Gly Val Pro
            115                 120                 125

Ala Gly Gly Val Pro Ala Glu Gly Val Pro Ala Gly Gly Val Pro Ala
        130                 135                 140

Gly Gly Val Pro Ala Ile Gly Val Pro Ala Gly Gly Val Pro Ala Gly
145                 150                 155                 160

Gly Val Pro Ala Glu Gly Val Pro Ala Gly Gly Val Pro Ala Gly Gly
            165                 170                 175

Val Pro Ala Ile Gly Val Pro Ala Gly Gly Val Pro Ala Gly Gly Val
            180                 185                 190

Pro Ala Glu Gly Val Pro Ala Gly Gly Val Pro Ala Gly Gly Val Pro
        195                 200                 205

Ala Ile Gly Val Pro Ala Gly Gly Val Pro Ala Gly Gly Val Pro Ala
210                 215                 220

Glu Gly Val Pro Ala Gly Gly Val Pro Ala Gly Gly Val Pro Ala Ile
225                 230                 235                 240

Gly Val Pro Ala Gly Gly Val Pro Ala Gly Gly Val Pro Ala Glu Gly
            245                 250                 255

Val Pro Ala Gly Gly Val Pro Ala Gly Gly Val Pro Ala Ile Gly Val
        260                 265                 270

Pro Ala Gly Gly Val Pro Ala Gly Gly Val Pro Ala Glu Gly Val Pro
        275                 280                 285

Ala Gly Gly Val Pro Ala Gly Gly Val Pro Ala Ile Gly Val Pro Ala
290                 295                 300

Gly Gly Val Pro Ala Gly Gly Val Pro Ala Glu Gly Val Pro Ala Gly
305                 310                 315                 320

Gly Val Pro Ala Gly Gly Val Pro Ala Ile Gly Val Pro Ala Gly Gly
            325                 330                 335

Val Pro Ala Gly Gly Val Pro Ala Glu Gly Val Pro Ala Gly Gly Val
        340                 345                 350

Pro Ala Gly Gly Val Pro Ala Ile Gly Val Pro Ala Gly Gly Val Pro
        355                 360                 365

Ala Ala Gly Val Pro Ala Phe Gly Val Pro Ala Ala Gly Val Pro Ala
370                 375                 380

Gly Gly Val Pro Ala Ala Gly Val Pro Ala Phe Gly Val Pro Ala Ala
385                 390                 395                 400

Gly Val Pro Ala Phe Gly Val Pro Ala Ala Gly Val Pro Ala Gly Gly
            405                 410                 415

Val Pro Ala Ala Gly Val Pro Ala Phe Gly Val Pro Ala Ala Gly Val
        420                 425                 430

Pro Ala Phe Gly Val Pro Ala Ala Gly Val Pro Ala Gly Gly Val Pro
        435                 440                 445

Ala Ala Gly Val Pro Ala Phe Gly Val Pro Ala Ala Gly Val Pro Ala
450                 455                 460

Phe Gly Val Pro Ala Ala Gly Val Pro Ala Gly Gly Val Pro Ala Ala
465                 470                 475                 480

Gly Val Pro Ala Phe Gly Val Pro Ala Ala Gly Val Pro Ala Phe Gly
            485                 490                 495

Val Pro Ala Ala Gly Val Pro Ala Gly Gly Val Pro Ala Ala Gly Val
        500                 505                 510

Pro Ala Phe Gly Val Pro Ala Ala Gly Val Pro Ala Phe Gly Val Pro
        515                 520                 525

Ala Ala Gly Val Pro Ala Gly Gly Val Pro Ala Ala Gly Val Pro Ala
```

530                 535                 540
Phe Gly Val Pro Ala Ala Gly Val Pro Ala Phe Gly Val Pro Ala Ala
545                 550                 555                 560

Gly Val Pro Ala Gly Gly Val Pro Ala Ala Gly Val Pro Ala Phe Gly
                565                 570                 575

Val Pro Ala Ala Gly Val Pro Ala Phe Gly Val Pro Ala Ala Gly Val
            580                 585                 590

Pro Ala Gly Gly Val Pro Ala Ala Gly Val Pro Ala Phe Gly Val Pro
        595                 600                 605

Ala Ala Gly Val Pro Ala Phe Gly Val Pro Ala Ala Gly Val Pro Ala
    610                 615                 620

Gly Gly Val Pro Ala Ala Gly Val Pro Ala Phe Gly Val Pro Ala Ala
625                 630                 635                 640

Gly Val Pro Ala Phe Gly Val Pro Ala Ala Gly Val Pro Ala Gly Gly
                645                 650                 655

Val Pro Ala Ala Gly Val Pro Ala Phe Gly Val Pro Ala Ala Gly Val
            660                 665                 670

Pro Ala Phe Gly Val Pro Ala Ala Gly Val Pro Ala Gly Gly Val Pro
        675                 680                 685

Ala Ala Gly Val Pro Ala Phe Gly Val Pro Ala Ala Gly Val Pro Ala
    690                 695                 700

Phe Gly Val Pro Ala Ala Gly Val Pro Ala Gly Gly Val Pro Ala Ala
705                 710                 715                 720

Gly Val Pro Ala Phe Gly
                725

<210> SEQ ID NO 53
<211> LENGTH: 1086
<212> TYPE: PRT
<213> ORGANISM: Artificial Sequence
<220> FEATURE:
<223> OTHER INFORMATION: anti-Flt1-EBPP[E1G4I1]12-EBPP[G1A3F2]24

<400> SEQUENCE: 53

Gly Asn Gln Trp Phe Ile Val Pro Ala Gly Gly Val Pro Ala Glu Gly
1               5                   10                  15

Val Pro Ala Gly Gly Val Pro Ala Gly Gly Val Pro Ala Ile Gly Val
            20                  25                  30

Pro Ala Gly Gly Val Pro Ala Gly Gly Val Pro Ala Glu Gly Val Pro
        35                  40                  45

Ala Gly Gly Val Pro Ala Gly Gly Val Pro Ala Ile Gly Val Pro Ala
    50                  55                  60

Gly Gly Val Pro Ala Gly Gly Val Pro Ala Glu Gly Val Pro Ala Gly
65                  70                  75                  80

Gly

```
            165                 170                 175
Val Pro Ala Ile Gly Val Pro Ala Gly Gly Val Pro Ala Gly Gly Val
            180                 185                 190

Pro Ala Glu Gly Val Pro Ala Gly Gly Val Pro Ala Gly Gly Val Pro
            195                 200                 205

Ala Ile Gly Val Pro Ala Gly Gly Val Pro Ala Gly Gly Val Pro Ala
            210                 215                 220

Glu Gly Val Pro Ala Gly Gly Val Pro Ala Gly Gly Val Pro Ala Ile
225                 230                 235                 240

Gly Val Pro Ala Gly Gly Val Pro Ala Gly Gly Val Pro Ala Glu Gly
            245                 250                 255

Val Pro Ala Gly Gly Val Pro Ala Gly Gly Val Pro Ala Ile Gly Val
            260                 265                 270

Pro Ala Gly Gly Val Pro Ala Gly Gly Val Pro Ala Glu Gly Val Pro
            275                 280                 285

Ala Gly Gly Val Pro Ala Gly Gly Val Pro Ala Ile Gly Val Pro Ala
            290                 295                 300

Gly Gly Val Pro Ala Gly Gly Val Pro Ala Glu Gly Val Pro Ala Gly
305                 310                 315                 320

Gly Val Pro Ala Gly Gly Val Pro Ala Ile Gly Val Pro Ala Gly Gly
            325                 330                 335

Val Pro Ala Gly Gly Val Pro Ala Glu Gly Val Pro Ala Gly Gly Val
            340                 345                 350

Pro Ala Gly Gly Val Pro Ala Ile Gly Val Pro Ala Gly Gly Val Pro
            355                 360                 365

Ala Ala Gly Val Pro Ala Phe Gly Val Pro Ala Ala Gly Val Pro Ala
            370                 375                 380

Gly Gly Val Pro Ala Ala Gly Val Pro Ala Phe Gly Val Pro Ala Ala
385                 390                 395                 400

Gly Val Pro Ala Phe Gly Val Pro Ala Ala Gly Val Pro Ala Gly Gly
            405                 410                 415

Val Pro Ala Ala Gly Val Pro Ala Phe Gly Val Pro Ala Ala Gly Val
            420                 425                 430

Pro Ala Phe Gly Val Pro Ala Ala Gly Val Pro Ala Gly Gly Val Pro
            435                 440                 445

Ala Ala Gly Val Pro Ala Phe Gly Val Pro Ala Ala Gly Val Pro Ala
            450                 455                 460

Phe Gly Val Pro Ala Ala Gly Val Pro Ala Gly Gly Val Pro Ala Ala
465                 470                 475                 480

Gly Val Pro Ala Phe Gly Val Pro Ala Ala Gly Val Pro Ala Phe Gly
            485                 490                 495

Val Pro Ala Ala Gly Val Pro Ala Gly Gly Val Pro Ala Ala Gly Val
            500                 505                 510

Pro Ala Phe Gly Val Pro Ala Ala Gly Val Pro Ala Phe Gly Val Pro
            515                 520                 525

Ala Ala Gly Val Pro Ala Gly Gly Val Pro Ala Ala Gly Val Pro Ala
            530                 535                 540

Phe Gly Val Pro Ala Ala Gly Val Pro Ala Phe Gly Val Pro Ala Ala
545                 550                 555                 560

Gly Val Pro Ala Gly Gly Val Pro Ala Ala Gly Val Pro Ala Phe Gly
            565                 570                 575

Val Pro Ala Ala Gly Val Pro Ala Phe Gly Val Pro Ala Ala Gly Val
            580                 585                 590
```

-continued

Pro Ala Gly Gly Val Pro Ala Ala Gly Val Pro Ala Phe Gly Val Pro
            595                 600                 605
Ala Ala Gly Val Pro Ala Phe Gly Val Pro Ala Ala Gly Val Pro Ala
            610                 615                 620
Gly Gly Val Pro Ala Ala Gly Val Pro Ala Phe Gly Val Pro Ala Ala
625                 630                 635                 640
Gly Val Pro Ala Phe Gly Val Pro Ala Ala Gly Val Pro Ala Gly Gly
            645                 650                 655
Val Pro Ala Ala Gly Val Pro Ala Phe Gly Val Pro Ala Ala Gly Val
            660                 665                 670
Pro Ala Phe Gly Val Pro Ala Ala Gly Val Pro Ala Gly Gly Val Pro
            675                 680                 685
Ala Ala Gly Val Pro Ala Phe Gly Val Pro Ala Ala Gly Val Pro Ala
            690                 695                 700
Phe Gly Val Pro Ala Ala Gly Val Pro Ala Gly Gly Val Pro Ala Ala
705                 710                 715                 720
Gly Val Pro Ala Phe Gly Val Pro Ala Ala Gly Val Pro Ala Phe Gly
            725                 730                 735
Val Pro Ala Ala Gly Val Pro Ala Gly Gly Val Pro Ala Ala Gly Val
            740                 745                 750
Pro Ala Phe Gly Val Pro Ala Ala Gly Val Pro Ala Phe Gly Val Pro
            755                 760                 765
Ala Ala Gly Val Pro Ala Gly Gly Val Pro Ala Ala Gly Val Pro Ala
            770                 775                 780
Phe Gly Val Pro Ala Ala Gly Val Pro Ala Phe Gly Val Pro Ala Ala
785                 790                 795                 800
Gly Val Pro Ala Gly Gly Val Pro Ala Ala Gly Val Pro Ala Phe Gly
            805                 810                 815
Val Pro Ala Ala Gly Val Pro Ala Phe Gly Val Pro Ala Ala Gly Val
            820                 825                 830
Pro Ala Gly Gly Val Pro Ala Ala Gly Val Pro Ala Phe Gly Val Pro
            835                 840                 845
Ala Ala Gly Val Pro Ala Phe Gly Val Pro Ala Ala Gly Val Pro Ala
            850                 855                 860
Gly Gly Val Pro Ala Ala Gly Val Pro Ala Phe Gly Val Pro Ala Ala
865                 870                 875                 880
Gly Val Pro Ala Phe Gly Val Pro Ala Ala Gly Val Pro Ala Gly Gly
            885                 890                 895
Val Pro Ala Ala Gly Val Pro Ala Phe Gly Val Pro Ala Ala Gly Val
            900                 905                 910
Pro Ala Phe Gly Val Pro Ala Ala Gly Val Pro Ala Gly Gly Val Pro
            915                 920                 925
Ala Ala Gly Val Pro Ala Phe Gly Val Pro Ala Ala Gly Val Pro Ala
            930                 935                 940
Phe Gly Val Pro Ala Ala Gly Val Pro Ala Gly Gly Val Pro Ala Ala
945                 950                 955                 960
Gly Val Pro Ala Phe Gly Val Pro Ala Ala Gly Val Pro Ala Phe Gly
            965                 970                 975
Val Pro Ala Ala Gly Val Pro Ala Gly Gly Val Pro Ala Ala Gly Val
            980                 985                 990
Pro Ala Phe Gly Val Pro Ala Ala  Gly Val Pro Ala Phe  Gly Val Pro
            995                 1000                1005

```
Ala Ala Gly Val Pro Ala Gly Gly Val Pro Ala Ala Gly Val Pro
    1010             1015             1020

Ala Phe Gly Val Pro Ala Ala Gly Val Pro Ala Phe Gly Val Pro
    1025             1030             1035

Ala Ala Gly Val Pro Ala Gly Gly Val Pro Ala Ala Gly Val Pro
    1040             1045             1050

Ala Phe Gly Val Pro Ala Ala Gly Val Pro Ala Phe Gly Val Pro
    1055             1060             1065

Ala Ala Gly Val Pro Ala Gly Gly Val Pro Ala Ala Gly Val Pro
    1070             1075             1080

Ala Phe Gly
    1085
```